US009539256B2

United States Patent
Cheng et al.

(10) Patent No.: US 9,539,256 B2
(45) Date of Patent: *Jan. 10, 2017

(54) MODULATORS OF EXCHANGE PROTEINS DIRECTLY ACTIVATED BY CAMP (EPACS)

(71) Applicant: THE BOARD OF REGENTS OF THE UNIVERSITY OF TEXAS SYSTEM, Austin, TX (US)

(72) Inventors: Xiaodong Cheng, League City, TX (US); Jia Zhou, League City, TX (US); Tamara Tsalkova, Galveston, TX (US); Fang Mei, League City, TX (US); Haijun Chen, Gelveston, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/377,574

(22) PCT Filed: Feb. 8, 2013

(86) PCT No.: PCT/US2013/025319
§ 371 (c)(1),
(2) Date: Aug. 8, 2014

(87) PCT Pub. No.: WO2013/119931
PCT Pub. Date: Aug. 15, 2013

(65) Prior Publication Data
US 2015/0110809 A1    Apr. 23, 2015

Related U.S. Application Data

(60) Provisional application No. 61/597,369, filed on Feb. 10, 2012.

(51) Int. Cl.
| | | |
|---|---|---|
| *A61K 31/513* | (2006.01) |
| *A61K 31/42* | (2006.01) |
| *A61K 31/4709* | (2006.01) |
| *A61K 45/06* | (2006.01) |
| *A61K 31/136* | (2006.01) |
| *A61K 31/10* | (2006.01) |
| *A61K 31/277* | (2006.01) |
| *A61K 31/505* | (2006.01) |

(52) U.S. Cl.
CPC ............ *A61K 31/513* (2013.01); *A61K 31/10* (2013.01); *A61K 31/136* (2013.01); *A61K 31/277* (2013.01); *A61K 31/42* (2013.01); *A61K 31/4709* (2013.01); *A61K 31/505* (2013.01); *A61K 45/06* (2013.01)

(58) Field of Classification Search
None
See application file for complete search history.

(56) References Cited

U.S. PATENT DOCUMENTS

| 5,760,063 A * | 6/1998 | Lam et al. ................... 514/355 |
| 2006/0100166 A1 | 5/2006 | De Kong et al. .............. 514/45 |
| 2009/0049622 A1 | 2/2009 | Matsunaga et al. .............. 8/426 |
| 2009/0169540 A1 | 7/2009 | Lezoualc'h et al. ........ 424/130.1 |
| 2010/0113379 A1 | 5/2010 | Rubinsztein et al. .......... 514/46 |
| 2011/0060029 A1 | 3/2011 | Iwatsubo et al. ........... 514/44 A |
| 2011/0251182 A1 | 10/2011 | Sun et al. .................... 514/218 |

FOREIGN PATENT DOCUMENTS

WO    WO/2009/033284    3/2009

OTHER PUBLICATIONS

Horig, H., Pullman, W. From bench to clinic and back: Perspective on the 1st IQPC Translational Research conference. Journal of Translational Medicine. Dec. 2004, 2, 44.*
Shafer, S., Kolkhof, P. Failure is an option: learning from unsuccessful proof-of-concept trials. Drug Discovery Today. Nov. 2008, 13, 913-916.*
Almahariq et al., A Novel EPAC-Specific Inhibitor Suppresses Pancreatic Cancer Cell Migration and Invasion. Molecular Pharmacology, 2013, 83, 122-128.*
Chemical Abstract Registry No. 263707-15-9, indexed in the Registry File on STN CAS Online May 3, 2000.*
Chemical Abstract Registry No. 263707-14-8, indexed in the Registry File on STN CAS Online May 3, 2000.*
Chemical Abstract Registry No. 263707-17-1, indexed in the Registry File on STN CAS Online May 3, 2000.*
Chan et al. (2009) *Cell Microbiol* 11(4):629-644.
Chan et al. (2010) *Front Microbiol* 1:139.
Cheung et al. (2012) *Am J Physiol Heart Circ Physiol* 303(11):H1374-H1383.
Cullere et al. (2005) *Blood* 105(5):1950-1955.
de Rooij et al. (1998) *Nature* 396: 474-477.
Fukuhara et al. (2005) *Mol Cell Biol* 25(1):136-146.
Gong et al. (2012) *PLoS Negl Trop Dis* 6(6):e1699.
Huston et al. (2008) *Proc Natl Acad Sci USA* 105(35):12791-1279647.
International Preliminary Report on Patentability in International Application No. PCT/US2013/025319 dated Aug. 12, 2014.
International Search Report and Written Opinion in International Application No. PCT/US2013/025319 dated Apr. 15, 2013.
Kawasaki et al. (1998) *Science* 282: 2275-2279.
Kooistra et al. (2005) *FEBS Lett* 579(22):4966-4972.
Martinez and Cossart (2004) *J Cell Sci* 117(Pt 21):5097-5106.
Martinez et al. (2005) *Cell* 123(6):1013-1023.
McDonough & Rodriguez (2012) *Nature Rev Microbiol* 10:27-38.
Pannekoek et al. (2011) *Cell Signal* 23(12):2056-2064.

(Continued)

*Primary Examiner* — Rebecca Anderson
*Assistant Examiner* — Po-Chih Chen
(74) *Attorney, Agent, or Firm* — Norton Rose Fulbright US LLP

(57) ABSTRACT

Embodiments of the invention are directed to compounds that inhibit an activity of EP AC proteins and methods of using the same. The inventors have developed a sensitive and robust high throughput screening (HTS) assay for the purpose of identifying EPAC specific inhibitors (Tsalkova et al. (2012) PLOS ONE 7(1):e30441).

21 Claims, 21 Drawing Sheets

(56) References Cited

OTHER PUBLICATIONS

Rampersad et al. (2010) *J Biol Chem* 285(44):33614-33622.
Schmidt (2013) *Pharmacol Rev* 65(2):670-709.
Schnoor et al. (2011) *J Exp Med* 208(8):1721-1735.
Shirshev (2011) *Biochemistry (Mosc)* 76:981-998.
Spindler et al. (2011) *Am J Pathol* 179(4):1905-1916.
Tsalkova, et al., "Isoform-specific antagonists of exchange proteins directly activated by cAMP" PNAS. 109(45):18613-8, 2012.
Walker and Ismail (2008) *Nat Rev Microbiol* 6(5):375-386.
Yeager et al (2009) *Infect Immun* 77:2530-2543.

* cited by examiner

| Chemical structure | IC$_{50}$ (μM) |
|---|---|
| HJC-2-71 | 0.7 |
| HJC-2-85 | 1.0 |
| HJC-2-82 | 1.9 |
| HJC-2-93 | 4-10*[a] |
| HJC-2-97 | 3-10*[a] |
| HJC-2-98 | 9-30*[a] |
| HJC-2-87 | 14 |

FIG. 2

| Chemical structure | IC$_{50}$ (μM) |
|---|---|
|  HJC-3-38 | 0.4 |
|  HJC-2-83 | 0.9 |
|  HJC-2-89 | 3.8-10*[a] |

| Chemical structure | IC$_{50}$ (μM) |
|---|---|
| HJC-3-50 | 0.4*[a] |
| HJC-3-26 | 0.4*[a] |
| HJC-2-79 | 0.5 |
| HJC-2-77 | 1.2 |
| HJC-3-55 | 1.3*[a] |
| HJC-2-81 | 2.4 |

| | |
|---|---|
| HJC-3-23 | 3.8*[a] |
| HJC-3-54 | 4.7*[a] |
| HJC-3-53 | 5.3*[a] |
| HJC-3-22 | 8.9*[a] |
| HJC-3-21 | 13*[a] |
| HJC-3-62 | 11*[a] |

FIG. 4

| NO | Structure | HPLC | HRMS | IC$_{50}$ (μM) |
|---|---|---|---|---|
| ESI-09 | 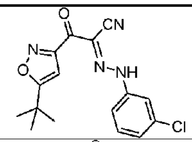 | $t_R$ = 21.72 min 99.6% | 331.0969 | 4.4 |
| HJC0683 | 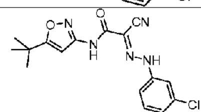 | $t_R$ = 20.97 min 96.7% | 346.1074 | >300 |
| HJC0692 | 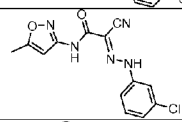 | $t_R$ = 18.55 min 98.5% | 304.0606 | >300 |
| HJC0693 | 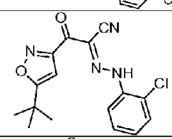 | $t_R$ = 22.77 min 96.6% | 331.0969 | 34 |
| HJC0694 | 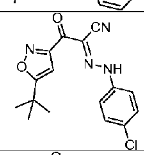 | $t_R$ = 21.74 min 98.1% | 331.0963 | 20 |
| HJC0695 | 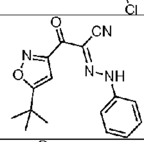 | $t_R$ = 20.50 min 99.4% | 297.1355 | 73 |
| HJC0696 | 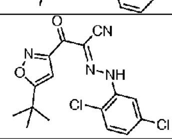 | $t_R$ = 23.69 min 97.1% | 365.0576 | 7.7 |
| HJC0712 | 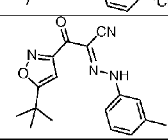 | $t_R$ = 21.29 min 99.0% | 311.1514 | 22.7 |
| HJC0720 | 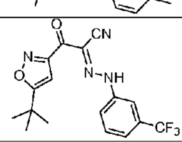 | $t_R$ = 21.80 min 96.0% | 365.1230 | 15.6 |
| HJC0721 | 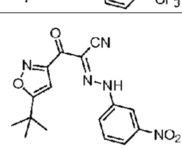 | $t_R$ = 20.33 min 96.4% | 342.1207 | 30 |

| | | | | |
|---|---|---|---|---|
| HJC0724 |  | $t_R$ = 21.36 min 98.6% | 311.1515 | 57 |
| HJC0726 |  | $t_R$ = 23.20 min 99.0% | 365.0563 | 1.0 |
| HJC0742 |  | $t_R$ = 22.01 min 98.9% | 375.0455 | 16 |
| HJC0743 |  | $t_R$ = 21.93 min 98.3% | 375.0456 | 11 |
| HJC0744 |  | $t_R$ = 23.01 min 98.6% | 325.1664 | >300 |
| HJC0745 |  | $t_R$ = 16.09 min 97.8% | 348.1458 | 77 |
| HJC0750 |  | $t_R$ = 23.74 min 97.5% | 365.0568 | 25 |
| HJC0751 |  | $t_R$ = 20.83 min 96.2% | 321.1350 | 72 |
| HJC0752 |  | $t_R$ = 21.53 min 98.8% | 369.1558 | 85 |
| HJC0753 |  | $t_R$ = 19.87 min 99.3% | 322.1303 | 72 |

| HJC0754 | | $t_R$ = 19.80 min 98.2% | 339.1459 | >300 |
|---|---|---|---|---|
| HJC0755 | | $t_R$ = 22.69 min 95.7% | 325.1666 | 270 |
| HJC0756 | | $t_R$ = 17.86 min 99.6% | 327.1457 | >300 |
| HJC0757 | | $t_R$ = 22.47 min 99.6% | 337.1664 | 27 |
| HJC0758 | | $t_R$ = 22.96 min 96.4% | 433.1098 | 6.8 |
| HJC0759 | | $t_R$ = 20.02 min 96.5% | 375.0858 | >300 |
| HJC0760 | | $t_R$ = 18.89 min 99.0% | 347.0909 | >300 |
| HJC0768 | | $t_R$ = 19.18 min 98.4% | 289.0492 | 106 |
| HJC0770 | | $t_R$ = 20.79 min 98.4% | 323.0103 | 18 |

FIG. 6 cont.

A
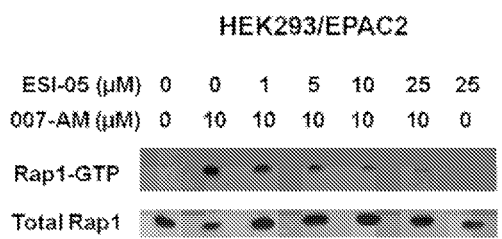 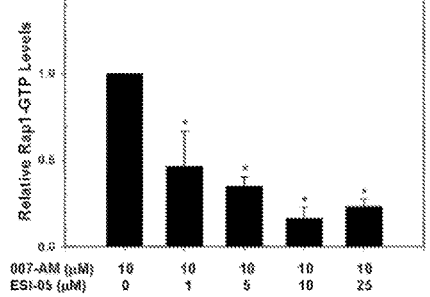
B
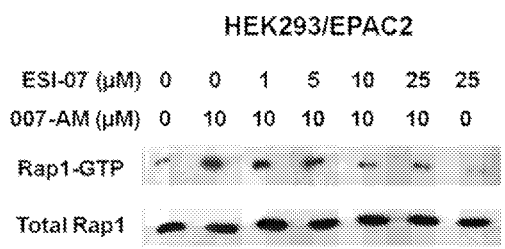 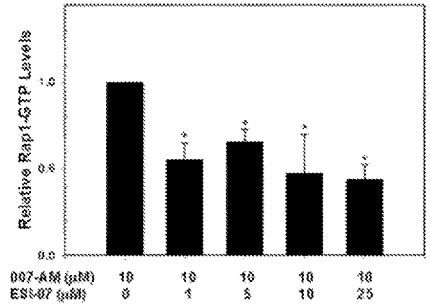
C
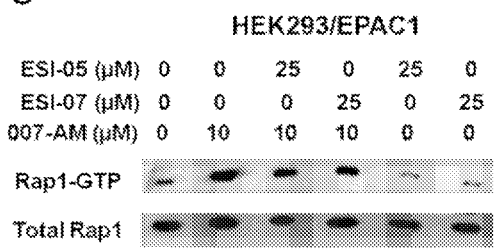 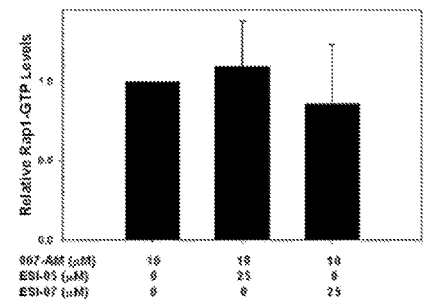
FIGs. 9A-9B

FIG. 21

MODULATORS OF EXCHANGE PROTEINS DIRECTLY ACTIVATED BY CAMP (EPACS)

This application is a national stage filing of international application PCT/US13/25319 filed Feb. 8, 2013, which claims priority to U.S. provisional application Ser. No. 61/597,369 filed Feb. 10, 2012. Priority is claim to each above referenced application and each application is incorporated herein by reference in its entirety.

TECHNICAL FIELD

Embodiments of the invention are directed to pharmacology, medicine, and medicinal chemistry. Certain embodiments are directed to compounds the modulate EPAC1 and/or EPAC2. Additional embodiments are directed to methods or medicaments using such compounds.

BACKGROUND

Identification and development of compounds capable of selectively targeting components of complex cell-signaling networks in a cell is a major effort of modern pharmacology. Cyclic adenosine monophosphate (cAMP), a prototypic second messenger, is an important component of cell-signaling networks that control numerous biological processes. In addition to its regulatory functions under physiological conditions, cAMP has been implicated in playing a major role in multiple human diseases, including cancer, diabetes, heart failure, and neurological disorders, such as Alzheimer's disease (AD). Therefore, it is not surprising that current pharmacological therapeutics target the cAMP signaling pathway more than any other pathway.

The major physiological effects of cAMP in mammalian cells are transduced by two ubiquitously expressed intracellular cAMP receptor families: the classic protein kinase A/cAMP-dependent protein kinases (PKAs/cAPKs) and the more recently discovered exchange proteins directly activated by cAMP/cAMP regulated guanine nucleotide exchange factors (EPACs/cAMP-GEFs). While a number of pharmacological inhibitors of PKA are available, only a few EPAC specific antagonists/inhibitors have been described. Thus, there remains a need for additional compositions and methods for selectively modulating EPAC1 and/or EPAC2.

SUMMARY

The inventors have developed a sensitive and robust high throughput screening (HTS) assay for the purpose of identifying EPAC specific inhibitors (Tsalkova et al. (2012) *PLOS ONE* 7 (1):e30441). Using this EPAC HTS assay, the inventors have successfully identified several isoform-specific EPAC inhibitors that are capable of blocking biochemical and cellular cAMP-induced EPAC activation (Tsalkova et al. (2012) *Proc. Acad. Natl. Sci. USA.* 109:18613-18618). In addition, the inventors have synthesized and characterized a number of chemical analogs of these EPAC specific inhibitors (ESI) (Chen et al. (2012) *Bioorganic & Medicinal Chemistry Letters.* 22:4038-4043; Chen et al. (2013) *J. Med. Chem.* In press; Chen et al. (2013) *Tetrahedron Lett.* In press). Some of these chemical analogs displayed more potent EPAC inhibition activity and better pharmacological properties than the parental compound. These EPAC specific inhibitors will not only provide a powerful pharmacological tool for dissecting the physiological functions of EPAC and for further elucidating the molecular mechanism of cAMP signaling, but also have important impacts on designing potential therapeutics targeting EPAC in diseases where cAMP signaling and EPAC proteins have been implicated. Studies using EPAC1 knockout mouse and ESIs suggest that EPAC1 plays important roles in obesity/diabetes (Yan et al. (2013) *Molecular Cellular Biology* 33:918-926), cancer (Almahariq et al. (2013) *Molecular Pharmacology.* 83:122-128), immune response, infection etc.

Certain embodiments are directed to an isolated Exchange Protein Activated by cAMP (EPAC) modulating compound having a general formula of Formula I:

Formula I where L' is —$SO_2$—, —NH—, or —C(O)—C(CN)=N—NH—; and W' and W" are independently substituted or unsubstituted aryl, or substituted or unsubstituted heteroaryl.

Further embodiments are directed to an isolated Exchange Protein Activated by cAMP (EPAC) modulating compound having a general formula of Formula II:

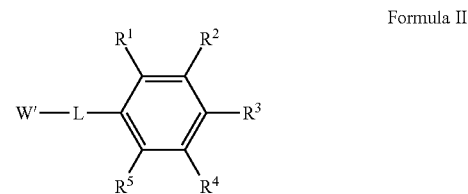

Formula II where $R^1$, $R^2$, $R^3$, $R^4$, and $R^5$ are independently hydrogen, hydroxyl, halogen, $C_1$-$C_4$ alkoxy; substituted or unsubstituted $C_1$-$C_{10}$ alkyl, substituted or unsubstituted $C_1$-$C_{10}$ heteroalkyl, substituted or unsubstituted $C_5$-$C_7$ cycloakyl, substituted or unsubstituted $C_5$-$C_7$ heterocyclyl, substituted or unsubstituted aryl, substituted or unsubstituted heteroaryl, or $C_1$-$C_5$ alkylamine; L is —$SO_2$— or —NH—; and W' is as described above for Formula I. In a further aspect, L is —$SO_2$—. In certain aspects W' is substituted phenyl or N-containing heteroaryl. In yet another aspect, a nitrogen in the N-containing heteroaryl is attached to L.

An isolated Exchange Protein Activated by cAMP (EPAC) modulating compound having a general formula of Formula III:

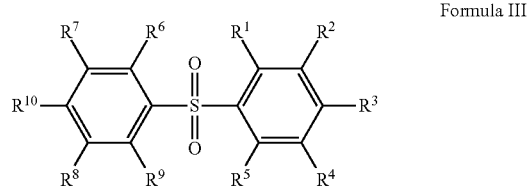

Formula III where $R^1$, $R^2$, $R^3$, $R^4$, $R^5$, $R^6$, $R^7$, $R^8$, $R^9$, and $R^{10}$ are independently hydrogen, hydroxyl, halogen, $C_1$-$C_4$ alkoxy, substituted or unsubstituted $C_1$-$C_{10}$ alkyl, substituted or unsubstituted $C_1$-$C_{10}$ heteroalkyl, substituted or unsubstituted $C_5$-$C_7$ cycloakyl, substituted or unsubstituted $C_5$-$C_7$ heterocyclyl, substituted or unsubstituted aryl, substituted or unsubstituted heteroaryl, or $C_1$-$C_5$ alkylamine. In certain aspects $R^1$, $R^2$, $R^3$, $R^4$, $R^5$, $R^6$, $R^7$, $R^8$, $R^9$, and $R^{10}$ are independently hydrogen or $C_1$-$C_{10}$ alkyl. In a further aspect, $R^1$, $R^3$, and $R^5$ are $C_1$-$C_{10}$ alkyl; and $R^2$ and $R^4$ are hydrogen. In still further aspects, one or more of $R^7$, $R^9$, and $R^{10}$ are $C_1$-$C_{10}$ alkyl. In yet further aspects $R^7$, $R^9$, and $R^{10}$ are $C_1$-$C_{10}$ alkyl. In certain aspects $R^{10}$ is substituted or unsubstituted $C_1$-$C_4$ alkyl or $C_1$-$C_4$ alkoxy. In yet other aspects, $R^{10}$ is halide or halo-substituted heteroaryl.

Certain embodiments are directed to a compound of Formula III where $R^1$, $R^3$, and $R^5$ are methyl; $R^2$ and $R^4$ are hydrogen; and (a) $R^7$, $R^9$, and $R^{10}$ are $C_1$-$C_{10}$ alkyl, and $R^6$ and $R^8$ are hydrogen; (b) $R^{10}$ is $C_1$-$C_{10}$ alkyl, and $R^6$, $R^7$, $R^8$, $R^9$ are hydrogen; (c) $R^{10}$ is $C_1$-$C_4$ alkoxy, and $R^6$, $R^7$, $R^8$, $R^9$ are hydrogen; (d) $R^{10}$ is halogen, and $R^6$, $R^7$, $R^8$, $R^9$ are hydrogen; (e) $R^{10}$ is hydroxyl, and $R^6$, $R^7$, $R^8$, $R^9$ are hydrogen; or (f) $R^{10}$ is a halogen or $C_{1-4}$ alkyl substituted pyridine, or a 2-, 4-, 5-, or 6-halo-pyridine, and $R^6$, $R^7$, $R^8$, $R^9$ are hydrogen.

Certain embodiments are directed to a compound of Formula III where $R^1$, $R^3$, and $R^5$ are methyl; $R^2$ and $R^4$ are hydrogen; and (a) $R^7$, $R^9$, and $R^{10}$ are methyl, and $R^6$ and $R^8$ are hydrogen; (b) $R^{10}$ is methyl, and $R^6$, $R^7$, $R^8$, $R^9$ are hydrogen; (c) $R^{10}$ is methoxy, and $R^6$, $R^7$, $R^8$, $R^9$ are hydrogen; (d) $R^{10}$ is iodo, and $R^6$, $R^7$, $R^8$, $R^9$ are hydrogen; (e) $R^{10}$ is hydroxyl, and $R^6$, $R^7$, $R^8$, $R^9$ are hydrogen; or (f) $R^{10}$ is 5-fluoro-pyridine and $R^6$, $R^7$, $R^8$, $R^9$ are hydrogen.

Certain embodiments are directed to a compound of Formula III where $R^3$ is methyl; $R^1$, $R^2$, $R^4$, and $R^5$, are hydrogen; and (a) $R^7$, $R^9$, and $R^{10}$ are $C_1$-$C_{10}$ alkyl, and $R^6$ and $R^8$ are hydrogen; (b) $R^{10}$ is $C_1$-$C_{10}$ alkyl, and $R^6$, $R^7$, $R^8$, $R^9$ are hydrogen; (c) $R^{10}$ is $C_1$-$C_4$ alkoxy, and $R^6$, $R^7$, $R^8$, $R^9$ are hydrogen; (d) $R^{10}$ is halogen, and $R^6$, $R^7$, $R^8$, $R^9$ are hydrogen; (e) $R^{10}$ is hydroxyl, and $R^6$, $R^7$, $R^8$, $R^9$ are hydrogen; or (f) $R^{10}$ is a halogen, $C_{1-4}$ alkyl substituted pyridine, or a 2-, 4-, 5-, or 6-halo-pyridine, and $R^6$, $R^7$, $R^8$, $R^9$ are hydrogen.

Certain embodiments are directed to a compound of Formula III where $R^3$ is methyl; $R^1$, $R^2$, $R^4$, and $R^5$, are hydrogen; and (a) $R^7$, $R^9$, and $R^{10}$ are methyl, and $R^6$ and $R^8$ are hydrogen; (b) $R^{10}$ is methyl, and $R^6$, $R^7$, $R^8$, $R^9$ are hydrogen; (c) $R^{10}$ is methoxy, and $R^6$, $R^7$, $R^8$, $R^9$ are hydrogen; (d) $R^{10}$ is iodo, and $R^6$, $R^7$, $R^8$, $R^9$ are hydrogen; (e) $R^{10}$ is hydroxyl, and $R^6$, $R^7$, $R^8$, $R^9$ are hydrogen; or (f) $R^{10}$ is 5-fluoro-pyridine, and $R^6$, $R^7$, $R^8$, $R^9$ are hydrogen.

In certain embodiments the compound of formula III is 1,3,5-trimethyl-2-(2,4,5-trimethyl-benzenesulfonyl)-benzene (HJC-2-71); 2-(4-methoxy-benzenesulfonyl)-1,3,5-trimethyl-benzene (HJC-2-82); 1,3,5-Trimethyl-2-(toluene-4-sulfonyl)-benzene (HJC-2-85); 4-(2,4,6-Trimethyl-benzenesulfonyl)-phenol (HJC-2-87); 2-(4-Iodo-benzenesulfonyl)-1,3,5-trimethyl-benzene (HJC-2-93); 2-Fluoro-5-[4-(2,4,6-trimethyl-benzenesulfonyl)-phenyl]-pyridine (HJC-2-97); or 1,2,4-Trimethyl-5-(toluene-4-sulfonyl)-benzene (HJC-2-98).

Still a further embodiment is directed to an isolated Exchange Protein Activated by cAMP (EPAC) modulating compound having a general formula of Formula IV:

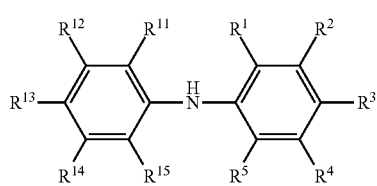

Formula IV where $R^1$, $R^2$, $R^3$, $R^4$, and $R^5$ are as described for Formula III above; and $R^{11}$, $R^{12}$, $R^{13}$, $R^{14}$, and $R^{15}$ are independently hydrogen, halogen, $C_1$-$C_{10}$ alkyl, or $C_1$-$C_{10}$ heteroalkyl. In certain aspects, $R^1$, $R^3$, and $R^5$ are $C_1$-$C_{10}$ alkyl; and $R^2$ and $R^4$ are hydrogen. In a further aspect, $R^{11}$, $R^{12}$, $R^{13}$, $R^{14}$, and $R^{15}$ are independently hydrogen, halogen, or $C_1$-$C_{10}$ alkyl.

Certain embodiments are directed to compounds of Formula IV where $R^1$, $R^3$, and $R^5$ are $C_1$-$C_{10}$ alkyl; $R^2$ and $R^4$ are hydrogen; and (a) $R^{11}$ and $R^{14}$ are halogen, and $R^{12}$, $R^{13}$, and $R^{15}$ are hydrogen; (b) $R^{12}$ and $R^{14}$ are halogen, and $R^{11}$, $R^{13}$, and $R^{15}$ are hydrogen; or (c) $R^{13}$ is $C_1$-$C_{10}$ alkyl, and $R^{11}$, $R^{12}$, $R^{14}$, and $R^{15}$ are hydrogen.

Certain embodiments are directed to compounds of Formula IV where $R^1$, $R^3$, and $R^5$ are methyl; $R^2$ and $R^4$ are hydrogen; and (a) $R^{11}$ and $R^{14}$ are chloro, and $R^{12}$, $R^{13}$, and $R^{15}$ are hydrogen; (b) $R^{12}$ and $R^{14}$ are chloro, and $R^{11}$, $R^{13}$, and $R^{15}$ are hydrogen; or (c) $R^{13}$ is methyl, and $R^{11}$, $R^{12}$, $R^{14}$, and $R^{15}$ are hydrogen.

In certain aspect the compound of formula IV is (3,5-Dichloro-phenyl)-(2,4,6-trimethyl-phenyl)-amine (HJC-2-83); p-Tolyl-(2,4,6-trimethyl-phenyl)-amine (HJC-2-89); or (2,5-Dichloro-phenyl)-(2,4,6-trimethyl-phenyl)-amine (HJC-3-38).

Certain embodiments are directed to an isolated Exchange Protein Activated by cAMP (EPAC) modulating compound having a general formula of Formula V:

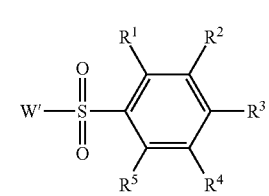

Formula V where $R^1$, $R^2$, $R^3$, $R^4$, and $R^5$ are as described in Formula III above; and W' is as described in Formula I above. In certain aspects, $R^1$, $R^2$, $R^3$, $R^4$, and $R^5$ are independently hydrogen, halogen, $C_1$-$C_{10}$ alkyl, or $C_1$-$C_{10}$ heteroalkyl. In certain aspects, W' is substituted or unsubstituted indole, substituted or unsubstituted azaindole, or substituted or unsubstituted pyrrole. In certain aspects, W' is unsubstituted indole or unsubstituted azaindole. In a further aspect, W' is pyrrole substituted with one or more $C_1$-$C_{10}$ alkyl groups. In certain aspects, W' is 1-ethylpyrrole or 2,4-dimethylpyrrole.

Certain embodiments are directed to compounds of Formula V where $R^1$, $R^3$, and $R^5$ are $C_1$-$C_{10}$ alkyl; $R^2$ and $R^4$ are hydrogen; and W' is substituted or unsubstituted indole, substituted or unsubstituted azaindole, or substituted or unsubstituted pyrrole. In certain aspects, W' is unsubstituted indole or unsubstituted azaindole. In a further aspect, W' is pyrrole substituted with one or more $C_1$-$C_{10}$ alkyl groups. In certain aspects, W' is 1-ethylpyrrole or 2,4-dimethylpyrrole.

Certain embodiments are directed to compounds of Formula V where $R^1$, $R^3$, and $R^5$ are methyl; $R^2$ and $R^4$ are hydrogen; and W' is substituted or unsubstituted indole, substituted or unsubstituted azaindole, or substituted or unsubstituted pyrrole. In certain aspects, W' is unsubstituted indole or unsubstituted 4-, 5-, 6-, or 7-azaindole. In a further aspect, W' is pyrrole substituted with one or more methyl or ethyl. In certain aspects, W' is 1-ethylpyrrole or 2,4-dimethylpyrrole.

Certain embodiments are directed to compounds of Formula V where $R^1$ and $R^3$ are $C_1$-$C_{10}$ alkyl; $R^2$, $R^4$, and $R^5$ are hydrogen; and W' is substituted or unsubstituted indole, substituted or unsubstituted azaindole, or substituted or unsubstituted pyrrole. In certain aspects, W' is unsubstituted indole or unsubstituted azaindole. In a further aspect, W' is pyrrole substituted with one or more $C_1$-$C_{10}$ alkyl groups. In certain aspects, W' is 1-ethylpyrrole or 2,4-dimethylpyrrole.

Certain embodiments are directed to compounds of Formula V where $R^1$ and $R^3$ are methyl; $R^2$, $R^4$, and $R^5$ are hydrogen; and W' is substituted or unsubstituted indole, substituted or unsubstituted azaindole, or substituted or unsubstituted pyrrole. In certain aspects, W' is unsubstituted indole or unsubstituted 4-, 5-, 6-, or 7-azaindole. In a further aspect, W' is pyrrole substituted with one or more methyl or ethyl. In certain aspects, W' is 1-ethylpyrrole or 2,4-dimethylpyrrole.

Certain embodiments are directed to compounds of Formula V where $R^2$ and $R^4$ are $C_1$-$C_{10}$ alkyl; $R^1$, $R^3$, and $R^5$ are hydrogen; and W' is substituted or unsubstituted indole, substituted or unsubstituted azaindole, or substituted or unsubstituted pyrrole. In certain aspects, W' is unsubstituted indole or unsubstituted azaindole. In a further aspect, W' is pyrrole substituted with one or more $C_1$-$C_4$ alkyl groups. In certain aspects, W' is 1-ethylpyrrole or 2,4-dimethylpyrrole.

Certain embodiments are directed to compounds of Formula V where $R^2$ and $R^4$ are methyl; $R^1$, $R^3$, and $R^5$ are hydrogen; and W' is substituted or unsubstituted indole, substituted or unsubstituted azaindole, or substituted or unsubstituted pyrrole. In certain aspects, W' is unsubstituted indole or unsubstituted 4-, 5-, 6-, or 7-azaindole. In a further aspect, W' is pyrrole substituted with one or more methyl or ethyl. In certain aspects, W' is 1-ethylpyrrole or 2,4-dimethylpyrrole.

Certain embodiments are directed to compounds of Formula V where $R^3$ is $C_1$-$C_{10}$ alkyl; $R^1$, $R^2$, $R^4$, and $R^5$ are hydrogen; and W' is substituted or unsubstituted indole, substituted or unsubstituted azaindole, or substituted or unsubstituted pyrrole. In certain aspects, W' is unsubstituted indole or unsubstituted azaindole. In a further aspect, W' is pyrrole substituted with one or more $C_1$-$C_{10}$ alkyl groups. In certain aspects, W' is 1-ethylpyrrole or 2,4-dimethylpyrrole.

Certain embodiments are directed to compounds of Formula V where $R^3$ is methyl; $R^1$, $R^2$, $R^4$, and $R^5$ are hydrogen; and W' is substituted or unsubstituted indole, substituted or unsubstituted azaindole, or substituted or unsubstituted pyrrole. In certain aspects, W' is unsubstituted indole or unsubstituted 4-, 5-, 6-, or 7-azaindole. In a further aspect, W' is pyrrole substituted with one or more methyl or ethyl. In certain aspects, W' is 1-ethylpyrrole or 2,4-dimethylpyrrole.

Certain embodiments are directed to compounds of Formula V where $R^1$ is $C_1$-$C_{10}$ alkyl; $R^2$, $R^3$, $R^4$, and $R^5$ are hydrogen; and W' is substituted or unsubstituted indole, substituted or unsubstituted azaindole, or substituted or unsubstituted pyrrole. In certain aspects, W' is unsubstituted indole or unsubstituted azaindole. In a further aspect, W' is pyrrole substituted with one or more $C_1$-$C_{10}$ alkyl groups. In certain aspects, W' is 1-ethylpyrrole or 2,4-dimethylpyrrole.

Certain embodiments are directed to compounds of Formula V where $R^1$ is methyl; $R^2$, $R^3$, $R^4$, and $R^5$ are hydrogen; and W' is substituted or unsubstituted indole, substituted or unsubstituted azaindole, or substituted or unsubstituted pyrrole. In certain aspects, W' is unsubstituted indole or unsubstituted 4-, 5-, 6-, or 7-azaindole. In a further aspect, W' is pyrrole substituted with one or more methyl or ethyl. In certain aspects, W' is 1-ethylpyrrole or 2,4-dimethylpyrrole.

In certain embodiments the compound of Formula V is 1-(2,4,6-Trimethyl-benzenesulfonyl)-1H-indole (HJC-2-77); 2-Ethyl-1-(2,4,6-trimethyl-benzenesulfonyl)-1H-pyrrole (HJC-2-79); 1-(2,4,6-Trimethyl-benzenesulfonyl)-1H-pyrrolo[2,3-b]pyridine (HJC-2-81); 1-(2,4,6-Trimethyl-benzenesulfonyl)-1H-pyrrolo[2,3-c]pyridine (HJC-3-21); 1-(2,4,6-Trimethyl-benzenesulfonyl)-1H-pyrrolo[3,2-c]pyridine (HJC-3-22); 1-(2,4,6-Trimethyl-benzenesulfonyl)-1H-pyrrolo[3,2-b]pyridine (HJC-3-23); 2-Ethyl-1-(toluene-4-sulfonyl)-1H-pyrrole (HJC-3-26); 2,4-Dimethyl-1-(2,4,6-trimethyl-benzenesulfonyl)-1H-pyrrole (HJC-3-50); 2-Ethyl-1-(toluene-2-sulfonyl)-1H-pyrrole (HJC-3-53); 1-(3,5-Dimethyl-benzenesulfonyl)-2-ethyl-1H-pyrrole (HJC-3-54); 1-(2,4-Dimethyl-benzenesulfonyl)-2-ethyl-1H-pyrrole (HJC-3-55); or 1-(2,4,6-Trimethyl-benzenesulfonyl)-1H-indole-5-carboxylic acid (HJC-3-62).

Certain embodiments are directed to an isolated Exchange Protein Activated by cAMP (EPAC) modulating compound having a formula of:

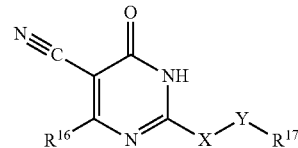

Formula VI where $R^{16}$ is substituted or unsubstituted $C_1$-$C_{10}$ alkyl, substituted or unsubstituted $C_3$-$C_6$ heteroalkyl, substituted or unsubstituted $C_3$-$C_6$ cycloalkyl, substituted or unsubstituted $C_3$-$C_6$ heterocyclyl, substituted or unsubstituted aryl, or substituted or unsubstituted heteroaryl; $R^{17}$ is hydrogen, substituted or unsubstituted aryl, or substituted or unsubstituted heteroaryl; X is sulfur or nitrogen; and Y is a direct bond, —$CH_2$—, —$CH_2C(O)O$—, or —$CH_2C(O)N$—. Formula VI represents an alternative embodiment of Formula I, where W' is a substituted pyrimidine, and L is a particular linker designated by —X—Y—.

Certain embodiments are directed to compounds of Formula VI where X is sulfur; Y is —$CH_2$—; $R^{16}$ is as described above for Formula VI; and $R^{17}$ is as described above for Formula VI. In certain aspects $R^{17}$ is as described above for Formula VI; and $R^{16}$ is (a) $C_3$-$C_6$ cycloalkyl, (b) $C_6$ cycloakyl, (c) $C_5$ cycloalkyl, (d) $C_4$ cycloalkyl, (e) $C_3$ cycloalkyl, (f) branched or linear $C_1$-$C_{10}$ alkyl, or (g) branched $C_3$ alkyl. In certain aspects, $R^{17}$ is substituted phenyl. In certain aspects, $R^{17}$ is a $C_1$-$C_{10}$ alkyl substituted phenyl. In further aspects, the substituted phenyl has 1, 2, or 3 $C_1$-$C_{10}$ alkyl substituents. In certain aspects the $C_1$-$C_{10}$ alkyl substituents are at positions 1, 3, and 5; 2 and 5; 2 and 4; 1 and 3; or 3 of the phenyl group. In a further aspect, $R^{17}$ is 3,6-dimethylphenyl; 3,5-dimethylphenyl; or 2,4-dimethylphenyl. In yet a further aspect, $R^{17}$ is 2,4,6-trimethylphenyl.

Certain embodiments are directed to compounds of Formula VI where X is sulfur; Y is —$CH_2C(O)N$—; $R^{16}$ is as described above for Formula VI; and $R^{17}$ is as described above for Formula VI. In certain aspects $R^{17}$ is as described above for Formula VI; and $R^{16}$ is (a) $C_3$-$C_6$ cycloalkyl, (b) $C_6$ cycloakyl, (c) $C_5$ cycloalkyl, (d) $C_4$ cycloalkyl, (e) $C_3$ cycloalkyl, (f) branched or linear $C_1$-$C_{10}$ alkyl, or (g) branched $C_3$ alkyl. In certain aspects, $R^{17}$ is substituted phenyl. In certain aspects, $R^{17}$ is a $C_1$-$C_{10}$ alkyl substituted phenyl. In further aspects, the substituted phenyl has 1, 2, or 3 $C_1$-$C_{10}$ alkyl substituents. In certain aspects the $C_1$-$C_{10}$ alkyl substituents are at positions 1, 3, and 5; 2 and 5; 2 and 4; 1 and 3; or 3 of the phenyl group. In a further aspect, $R^{17}$ is 3,6-dimethylphenyl; 3,5-dimethylphenyl; or 2,4-dimethylphenyl. In yet a further aspect, $R^{17}$ is 2,4,6-trimethylphenyl.

Certain embodiments are directed to compounds of Formula VI where X is nitrogen; Y is —CH$_2$—; $R^{16}$ is as described above for Formula VI; and $R^{17}$ is as described above for Formula VI. In certain aspects $R^{17}$ is as described above for Formula VI; and $R^{16}$ is (a) $C_3$-$C_6$ cycloakyl, (b) $C_6$ cycloakyl, (c) $C_5$ cycloalkyl, (d) $C_4$ cycloalkyl, (e) $C_3$ cycloalkyl, (f) branched or linear $C_1$-$C_{10}$ alkyl, or (g) branched $C_3$ alkyl. In certain aspects, $R^{17}$ is substituted phenyl. In certain aspects, $R^{17}$ is a $C_1$-$C_{10}$ alkyl substituted phenyl. In further aspects, the substituted phenyl has 1, 2, or 3 $C_1$-$C_{10}$ alkyl substituents. In certain aspects the $C_1$-$C_{10}$ alkyl substituents are at positions 1, 3, and 5; 2 and 5; 2 and 4; 1 and 3; or 3 of the phenyl group. In a further aspect, $R^{17}$ is 3,6-dimethylphenyl; 3,5-dimethylphenyl; or 2,4-dimethylphenyl. In yet a further aspect, $R^{17}$ is 2,4,6-trimethylphenyl.

Certain embodiments are directed to compounds of Formula VI where X is nitrogen; Y is a direct bond; $R^{16}$ is as described above for Formula VI; and $R^{17}$ is as described above for Formula VI. In certain aspects $R^{17}$ is as described above for Formula VI; and $R^{16}$ is (a) $C_3$-$C_6$ cycloakyl, (b) $C_6$ cycloakyl, (c) $C_5$ cycloalkyl, (d) $C_4$ cycloalkyl, (e) $C_3$ cycloalkyl, (f) branched or linear $C_1$-$C_{10}$ alkyl, or (g) branched $C_3$ alkyl. In certain aspects, $R^{17}$ is substituted phenyl. In certain aspects, $R^{17}$ is a $C_1$-$C_{10}$ alkyl substituted phenyl. In further aspects, the substituted phenyl has 1, 2, or 3 $C_1$-$C_{10}$ alkyl substituents. In certain aspects the $C_1$-$C_{10}$ alkyl substituents are at positions 1, 3, and 5; 2 and 5; 2 and 4; 1 and 3; or 3 of the phenyl group. In a further aspect, $R^{17}$ is 3,6-dimethylphenyl; 3,5-dimethylphenyl; or 2,4-dimethylphenyl. In yet a further aspect, $R^{17}$ is 2,4,6-trimethylphenyl.

In certain embodiments a compound of Formula VI is 4-Cyclohexyl-2-(2,5-dimethyl-benzylsulfanyl)-6-oxo-1,6-dihydro-pyrimidine-5-carbonitrile (HJC-1-65); 4-Cyclohexyl-2-(4-methyl-benzylsulfanyl)-6-oxo-1,6-dihydro-pyrimidine-5-carbonitrile (HJC-1-67); 4-Cyclohexyl-2-(3,5-dimethyl-benzylsulfanyl)-6-oxo-1,6-dihydro-pyrimidine-5-carbonitrile (HJC-1-72); 4-Cyclohexyl-2-(2,4-dimethyl-benzylsulfanyl)-6-oxo-1,6-dihydro-pyrimidine-5-carbonitrile (HJC-1-74); 2-Benzylsulfanyl-4-cyclohexyl-6-oxo-1,6-dihydro-pyrimidine-5-carbonitrile (HJC-1-76); 4-Cyclohexyl-6-oxo-2-(2,4,6-trimethyl-benzylsulfanyl)-1,6-dihydro-pyrimidine-5-carbonitrile (HJC-1-87); 2-(2,5-Dimethyl-benzylsulfanyl)-4-isopropyl-6-oxo-1,6-dihydro-pyrimidine-5-carbonitrile (HJC-1-95); 4-Cyclopentyl-2-(2,5-dimethyl-benzylsulfanyl)-6-oxo-1,6-dihydro-pyrimidine-5-carbonitrile (HJC-1-97); 4-Cyclopropyl-2-(2,5-dimethylbenzylsulfanyl)-6-oxo-1,6-dihydro-pyrimidine-5-carbonitrile (HJC-1-98); 4-Cyclohexyl-6-oxo-2-phenylamino-1,6-dihydro-pyrimidine-5-carbonitrile (HJC-1-99); 4-[5-Cyano-2-(2,5-dimethylbenzylsulfanyl)-6-oxo-1,6-dihydro-pyrimidin-4-yl]-piperidine-1-carboxylic acid tert-butyl ester (HJC-1-93); (5-Cyano-4-cyclohexyl-6-oxo-1,6-dihydro-pyrimidin-2-ylsulfanyl)-acetic acid (HJC-2-4); 2-(5-Cyano-4-cyclohexyl-6-oxo-1,6-dihydro-pyrimidin-2-ylsulfanyl)-N-(2,4,6-trimethyl-phenyl)-acetamide (HJC-3-33); or 2-(5-Cyano-4-cyclohexyl-6-oxo-1,6-dihydro-pyrimidin-2-ylsulfanyl)-N-p-tolyl-acetamide (HJC-3-35).

Certain embodiments are directed to an isolated Exchange Protein Activated by cAMP (EPAC) modulating compound having a formula of:

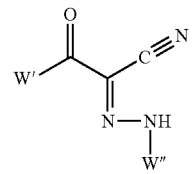

Formula VII in certain aspects W' and W" are as described for Formula I above.

In certain embodiments W' is an unsubstituted or substituted isoxazole. In certain aspects the isoxazole is attached via the 3 position. In certain aspects the substituted isoxazole is a 4-substituted isoxazole, a 5-substituted isoxazole, or a 4,5-substituted isoxazole. In a particular aspect the substituted isoxazole is a 5-substituted isoxazole. In certain aspects the substituent is independently a branched or unbranched $C_1$ to $C_{10}$ alkyl. In certain aspect the alkyl is a methyl, ethyl, n-propyl, iso-propyl, n-butyl, sec-butyl, iso-butyl, tert-butyl, neo-pentyl, n-pentyl, or isopenyl. In certain embodiments the isoxazole is a 5-methyl or 5 tert-butyl isoxazole. In a further aspect W' can be a substituted to unsubstituted phenyl.

In certain embodiments W" is a monocyclic or polycyclic, substituted or unsubstituted aryl or heteroaryl. In certain aspects W" is a substituted phenyl or N-containing heteroaryl. In a further aspect the substituted phenyl is a 2; 3; 4; 5; 6; 2,3; 2,4; 2,5; 2,6; 3,4; 3,5; 3,6; 4,5; 4,6; or 5,6 substituted phenyl. In still further aspects the phenyl comprises one or more substituent selected from bromo, fluoro, chloro, iodo, $C_1$-$C_4$ alkyl, hydroxy, nitro, fluoromethyl, difluoromethyl, trifluoromethyl, nitrile, $C_1$-$C_4$ alkynyl, acetyl, $C_1$-$C_4$ hydroxyalkyl, $C_1$-$C_4$ alkoxy, or carboxyl group. In certain aspects W" is a substituted or unsubstituted benzopyridine or a substituted or unsubstituted indane. In certain aspects W" is a 3-chlorophenyl; 2-chlorophenyl; 4-chlorophenyl; phenyl; 3,6-dichlorophenyl; 3-methylphenyl, 3-trifluoromethylphenyl; 3-nitrophenyl; 4-methylphenyl, 3,5-dichlorophenyl; 4-bromophenyl; 3-bromophenyl; 3,6-dimethylphenyl; benzopyridine; 2,3-dichlorophenyl; 3-ethynyl; benzoic acid ethyl ester; 3-benzonitrile; 3-acetylphenyl; 2,3-methylphenyl; 3-ethoxyphenyl; indane; 3,5-ditrifluoromethylphenyl; 6-chloro-benzoic acid; or 3-chloro, 4-hydroxyphenyl.

In certain aspects a compound of Formula VII is selected from N-(5-tert-Butyl-isoxazol-3-yl)-2-[(3-chlorophenyl)-hydrazono]-2-cyanoacetamide (HJC0683); 2-[(3-Chlorophenyl)-hydrazono]-2-cyano-N-(5-methyl-isoxazol-3-yl)acetamide (HJC0692); 3-(5-tert-Butyl-isoxazol-3-yl)-2-[(3-chlorophenyl)-hydrazono]-3-oxo-propionitrile (HJC0680, ESI-09); 3-(5-tert-Butyl-isoxazol-3-yl)-2-[(2-chlorophenyl)-hydrazono]-3-oxo-propionitrile (HJC0693); 3-(5-tert-Butyl-isoxazol-3-yl)-2-[(4-chlorophenyl)-hydrazono]-3-oxo-propionitrile (HJC0694); 3-(5-tert-Butyl-isoxazol-3-yl)-3-oxo-2-(phenyl-hydrazono)-propionitrile (HJC0695); 3-(5-tert-Butyl-isoxazol-3-yl)-2-[(2,5-dichlorophenyl)-hydrazono]-3-oxo-propionitrile (HJC0696); 3-(5-tert-Butyl-isoxazol-3-yl)-3-oxo-2-(m-tolyl-hydrazono)propionitrile (HJC0712); 3-(5-tert-Butyl-isoxazol-3-yl)-3-oxo-2-[(3-trifluoromethyl-phenyl)-hydrazono]propionitrile (HJC0720); 3-(5-tert-Butyl-isoxazol-3-yl)-2-[(3-nitrophenyl)-hydrazono]-3-oxo-propionitrile (HJC0721); 3-(5-tert-Butyl-isoxazol-3-yl)-3-oxo-2-(p-tolyl-hydrazono)propionitrile (HJC0724); 3-(5-tert-Butyl-isoxazol-3-yl)-2-[(3,5-dichlorophenyl)-hydrazono]-3-oxo-propionitrile (HJC0726); 2-[(4-

Bromophenyl)-hydrazono]-3-(5-tert-butyl-isoxazol-3-yl)-3-oxo-propionitrile (HJC0742); 2-[(3-Bromophenyl)-hydrazono]-3-(5-tert-butyl-isoxazol-3-yl)-3-oxo-propionitrile (HJC0743); 3-(5-tert-Butyl-isoxazol-3-yl)-2-[(2,5-dimethylphenyl)-hydrazono]-3-oxo-propionitrile (HJC0744); 3-(5-tert-Butyl-isoxazol-3-yl)-3-oxo-2-(quinolin-6-yl-hydrazono)propionitrile (HJC0745); 3-(5-tert-Butyl-isoxazol-3-yl)-2-[(2,3-dichlorophenyl)-hydrazono]-3-oxo-propionitrile (HJC0750); 3-(5-tert-Butyl-isoxazol-3-yl)-2-[(3-ethynyl-phenyl)-hydrazono]-3-oxo-propionitrile (HJC0751); 3-{N-[2-(5-tert-Butyl-isoxazol-3-yl)-1-cyano-2-oxo-ethylidene]-hydrazino}benzoic acid ethyl ester (HJC0752); 3-{N-[2-(5-tert-Butyl-isoxazol-3-yl)-1-cyano-2-oxo-ethylidene]-hydrazino}benzonitrile (HJC0753); 2-[(3-Acetyl-phenyl)-hydrazono]-3-(5-tert-butyl-isoxazol-3-yl)-3-oxo-propionitrile (HJC0754); 3-(5-tert-Butyl-isoxazol-3-yl)-2-[(2,3-dimethylphenyl)-hydrazono]-3-oxo-propionitrile (HJC0755); 3-(5-tert-Butyl-isoxazol-3-yl)-2-[(3-hydroxymethylphenyl)-hydrazono]-3-oxo-propionitrile (HJC0756); 3-(5-tert-Butyl-isoxazol-3-yl)-2-(indan-5-yl-hydrazono)-3-oxo-propionitrile (HJC0757); 2-[(3,5-Bis-trifluoromethyl-phenyl)-hydrazono]-3-(5-tert-butyl-isoxazol-3-yl)-3-oxo-propionitrile (HJC0758); 2-{N-[2-(5-tert-Butyl-isoxazol-3-yl)-1-cyano-2-oxo-ethylidene]-hydrazino}-6-chloro-benzoic acid (HJC0759); 3-(5-tert-Butyl-isoxazol-3-yl)-2-[(3-chloro-4-hydroxy-phenyl)-hydrazono]-3-oxo-propionitrile (HJC0760); 2-[(3-Chloro-phenyl)-hydrazono]-3-(5-methyl-isoxazol-3-yl)-3-oxo-propionitrile (HJC0768); or 2-[(3,5-Dichlorophenyl)-hydrazono]-3-(5-methyl-isoxazol-3-yl)-3-oxo-propionitrile (HJC0770).

Certain embodiments are directed to using one or more EPAC modulators to treat or enhance a therapy for a disease or condition associated with EPAC activity.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention.

As used herein, the term "$IC_{50}$" refers to an inhibitory dose that results in 50% of the maximum response obtained.

The term half maximal effective concentration ($EC_{50}$) refers to the concentration of a drug that presents a response halfway between the baseline and maximum after some specified exposure time.

The terms "inhibiting," "reducing," or "prevention," or any variation of these terms, when used in the claims and/or the specification includes any measurable decrease or complete inhibition to achieve a desired result.

As used herein, an "inhibitor" as described herein, for example, can inhibit directly or indirectly the activity of a protein. The term "EPAC inhibitor" refers to a compound that decreases the activity of EPAC in a cell. In certain aspects an EPAC inhibitor decreases cancer cell or carcinoma migration by any measurable amount, as compared to such a cell in the absence of such an inhibitor. EPAC inhibitors include EPAC1 inhibitors and/or EPAC2 inhibitors.

As used herein, an "activator" as described herein, for example, can increase the activity of a protein. The term "EPAC activator" refers to a compound that increases the activity of EPAC in a cell. EPAC activators include EPAC1 activators and/or EPAC2 activators.

An "effective amount" of an agent in reference to treating a disease or condition means an amount capable of decreasing, to some extent, a pathological condition or symptom resulting from a pathological condition. The term includes an amount capable of invoking a growth inhibitory, cytostatic and/or cytotoxic effect and/or apoptosis of the cancer or tumor cells.

The phrases "treating cancer" and "treatment of cancer" mean to decrease, reduce, or inhibit the replication of cancer cells; decrease, reduce or inhibit the spread (formation of metastases) of cancer; decrease tumor size; decrease the number of tumors (i.e. reduce tumor burden); lessen or reduce the number of cancerous cells in the body; prevent recurrence of cancer after surgical removal or other anti-cancer therapies; or ameliorate or alleviate the symptoms of the disease caused by the cancer.

As used herein, the term "patient" or "subject" refers to a living mammalian organism, such as a human, monkey, cow, sheep, goat, dogs, cat, mouse, rat, guinea pig, or species thereof. In certain embodiments, the patient or subject is a primate. Non-limiting examples of human subjects are adults, juveniles, infants and fetuses.

The terms "comprise," "have," and "include" are open-ended linking verbs. Any forms or tenses of one or more of these verbs, such as "comprises," "comprising," "has," "having," "includes," and "including," are also open-ended. For example, any method that "comprises," "has," or "includes" one or more steps is not limited to possessing only those one or more steps and also covers other unlisted steps.

The use of the term "or" in the claims is used to mean "and/or" unless explicitly indicated to refer to alternatives only or the alternatives are mutually exclusive, although the disclosure supports a definition that refers to only alternatives and "and/or."

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

FIG. 2. Examples of compounds having a general formula of Formula III.

FIG. 4. Examples of compounds having a general formula of Formula V.

FIGS. 9A-9B. Effects of EPAC2-specific antagonists on 007-AM-mediated cellular activation of Rap1. Serum-starved HEK293/EPAC2 cells or HEK293/EPAC1 cells with or without pretreatment of ESI-05 or ESI-07 for 5 min were stimulated with 10 µM 007-AM for 10 min. GTP-bound Rap1 (Rap1GTP) obtained by a Ral-GDSRBD-GST pull-down assay and total cellular Rap1 were detected by immunoblotting with Rap1-specific antibody. (A) HEK293/EPAC2 cells treated with ESI-05. (B) HEK293/EPAC2 cells treated with ESI-07. (C) HEK293/EPAC1 cells treated with ESI-05 or ESI-07. Similar results were obtained with three independent experiments for each panel. At test was used to determine statistical significance (*P<0.05).

Figure 21:
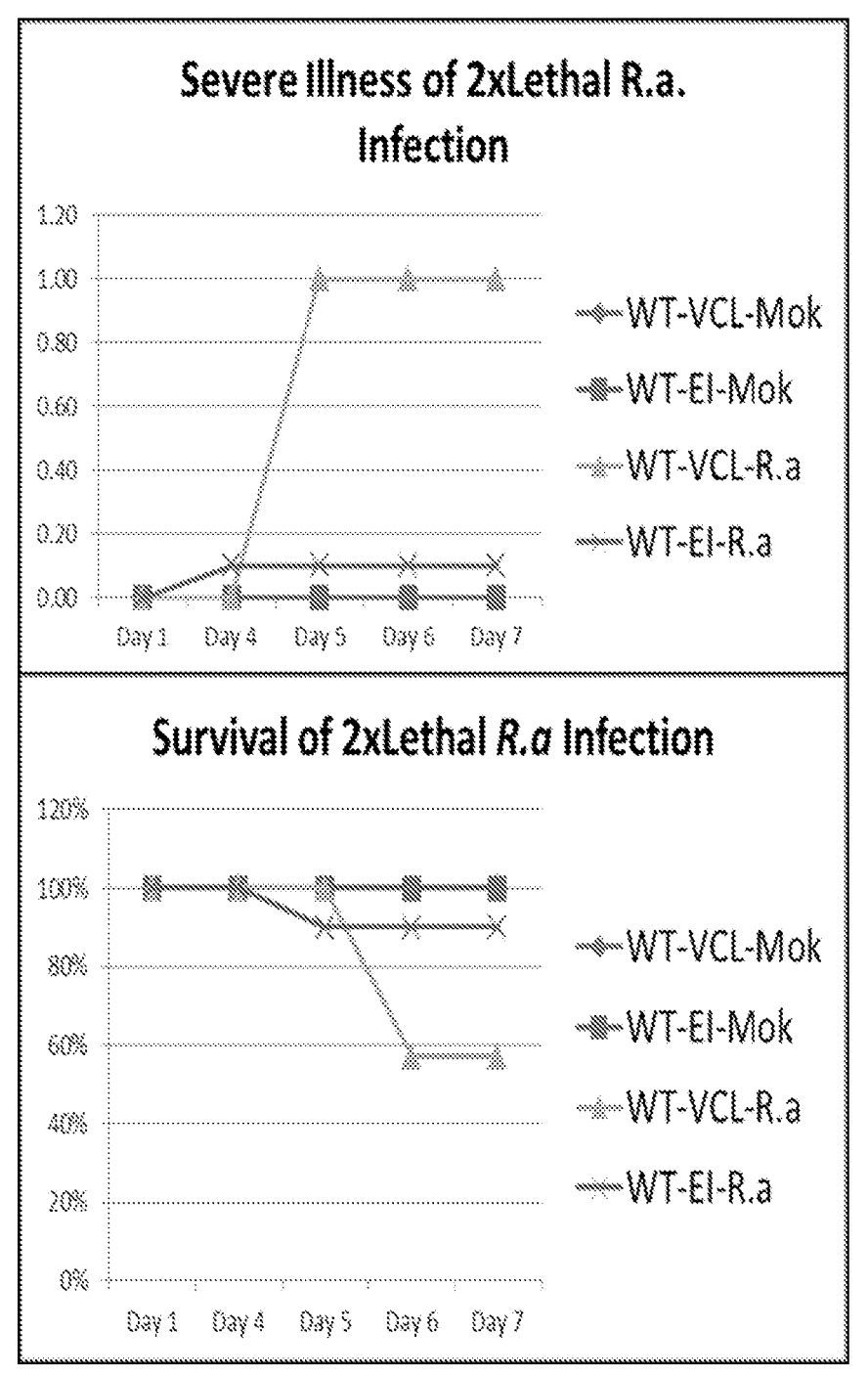

FIG. 21. ESI-09 treatment protects mice from lethal-dose infection of R. australia. WT C57BL/6 mice were treated with vehicle or ESI-09 (10 mg/kg, IP) daily. Five days after the treatment, mice were challenged with lethal dose of R. australia and continued ESI-09 daily treatment. Severity of illness and survival rate were monitored.

Figure 1:
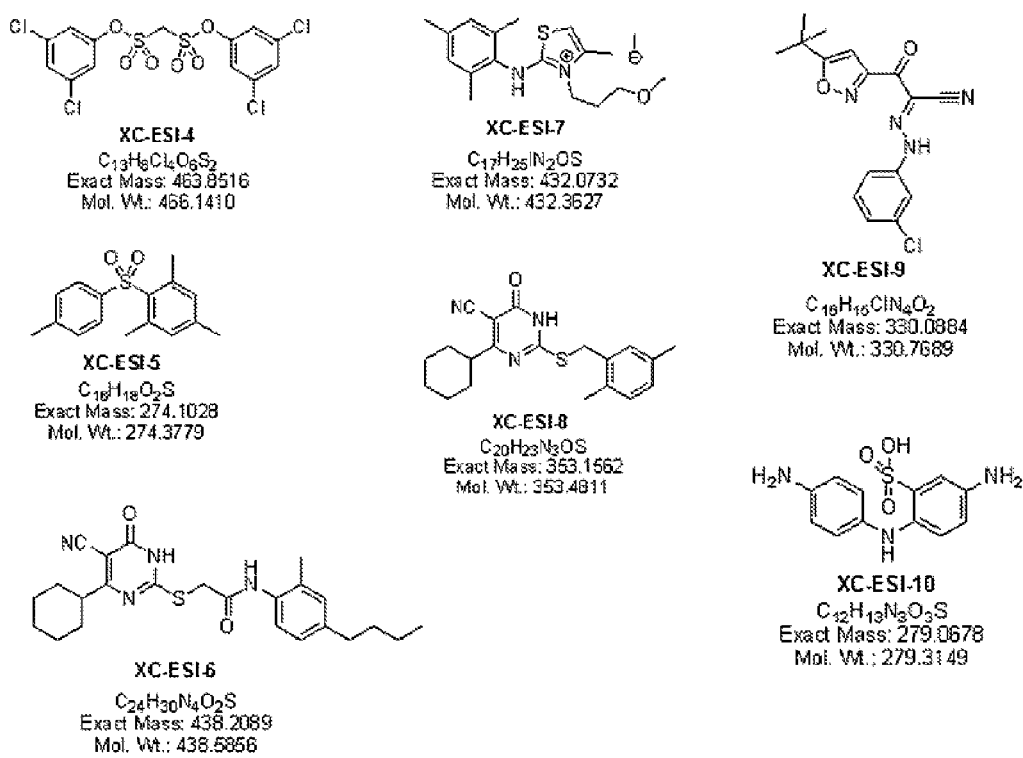
FIG. 1. Chemical Structures of Hits and General Strategy to Create New Epac2 Probes.
Figure 3:
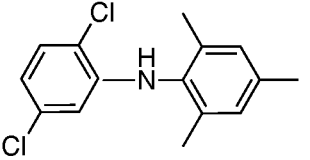
FIG. 3. Examples of compounds having a general formula of Formula IV.
Figure 3:
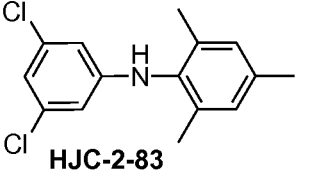
Figure 3:
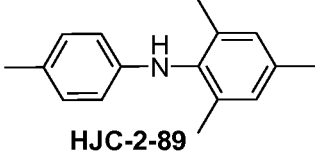
Figure 5:
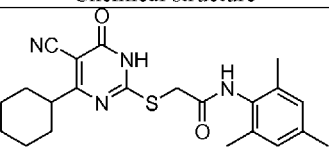
FIG. 5. Examples of compounds having a general formula of Formula VI.
Figure 6:
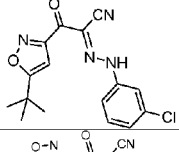
FIG. 6. Examples of compounds having a general formula of Formula VII.
Figure 6:
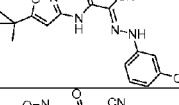
Figure 6:
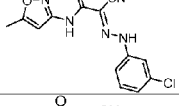
Figure 6:
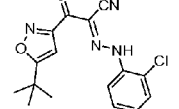
Figure 6:
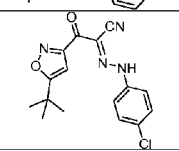
Figure 6:
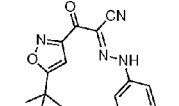
Figure 6:
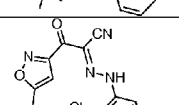
Figure 6:
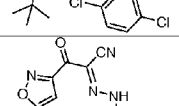
Figure 6:
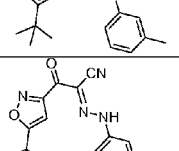
Figure 6:
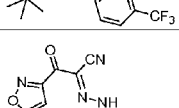
Figure 6:
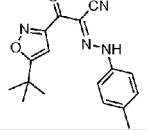
Figure 6:
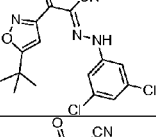
Figure 6:
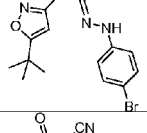
Figure 6:
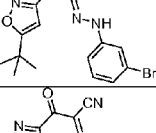
Figure 6:
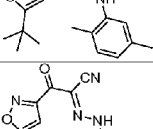
Figure 6:
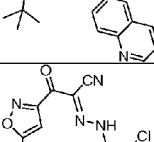
Figure 6:
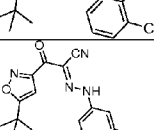
Figure 6:
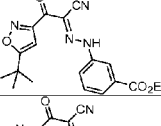
Figure 6:
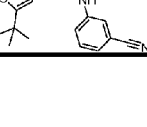
Figure 6:

DESCRIPTION cAMP-mediated signaling regulates a myriad of important biological processes under both physiological and pathological conditions. In multi-cellular eukaryotic organisms, the effects of cAMP are transduced by the protein kinase A/cAMP-dependent protein kinase (PKA/cAPK) and the exchange protein directly activated by cAMP/cAMP-regulated guanine nucleotide exchange factor (EPAC/cAMP-GEF) (de Rooij et al. (1998) *Nature* 396: 474-477; Kawasaki et al. (1998) *Science* 282: 2275-2279). Since both PKA and EPAC are ubiquitously expressed in all tissues, an increase in intracellular cAMP levels will lead to the activation of both PKA and EPAC. Net physiological effects of cAMP entail the integration of EPAC- and PKA-dependent pathways in a spatial and temporal manner. Depending upon their relative abundance, distribution and localization, as well as the precise cellular environment, the two intracellular cAMP receptors may act independently, converge synergistically, or oppose each other in regulating a specific cellular function (Cheng et al. (2008) *Acta Biochim Biophys Sin* (Shanghai) 40: 651-662). Therefore, careful dissections of the individual role and relative contribution of EPAC and PKA within the overall cAMP signaling in various model systems are critical for further elucidating the mechanism of cAMP signaling, as well as essential for developing novel mechanism-based therapeutic strategies targeting specific cAMP-signaling components.

Cyclic AMP is a second messenger that induces physiological responses ranging from growth and differentiation to hormonal, neuronal, and immunological regulation (Tasken and Aandahl (2004) *Physiol Rev* 84:137-167; Holz (2004) *Diabetes* 53:5-13). In the brain, it is involved in memory (Huang et al. (1995) *Cell* 83:1211-1222) and cognitive functions (Sur and Rubenstein (2005) *Science* 310: 805-810). There are two forms of EPAC, EPAC1 and EPAC2, which are encoded by separate genes, EPAC1 and EPAC2, respectively. EPAC1 is expressed ubiquitously with predominant expression in the thyroid, kidney, ovary, skeletal muscle, and specific brain regions. EPAC2 is predominantly expressed in the brain and adrenal gland (de Rooij et al. (1998) *Nature* 396:474-477; Kawasaki et al. (1998) *Science* 282:2275 2279).

Embodiments described herein are directed to compounds that modulate EPAC1 and/or EPAC2. Certain embodiments are directed to compounds that specifically modulate EPAC2 or EPAC1. Further embodiments are directed to methods and medicaments for treating EPAC associated diseases or conditions.

I. High Throughput EPAC Assay

The inventors developed a fluorescence-based high throughput assay for screening EPAC specific antagonists (Tsalkova et al. (2012) *PLoS. ONE.* 7: e30441). The assay is highly reproducible and simple to perform using the "mix and measure" format. A pilot screening led to the identification of small chemical compounds capable of specifically inhibiting cAMP-induced EPAC activation while not affecting PKA activity, i.e., EPAC specific inhibitors (ESI).

Primary Screen Assay—

Fluorescence intensity of 8-NBD-cAMP in complex with EPAC2 is used as the readout in the primary screen assay. Primary screen is performed in black 96-well or 384-well microplates. As an example, 50 nM EPAC2 solution is prepared in 20 mM Tris buffer, pH 7.5, containing 150 mM NaCl, 1 mM EDTA, and 1 mM DTT. 8-NBD-cAMP is added to EPAC2 solution up to 60 nM from a stock solution in water. Sample is dispensed into plate and test compounds added from 96-well mother plates. Samples with cAMP addition and no additions are used as a positive and a negative control. Fluorescence intensity signal from 8-NBD was recorded at room temperature (rt) before and after tested compounds are added using SpectaMaxM2 microplate reader (Molecular Devices, Silicon Valley, Calif., USA) with excitation/emission wavelengths set at 470/540 nm.

Secondary Confirmation Assay—

Measurement of in vitro guanine nucleotide exchange factor (GEF) activity of EPAC was adapted from a well known fluorescence-based assay using a fluorescent guanine nucleotide analog (van den Berghe et al. (1997) *Oncogene* 15: 845-850), and used as a functional confirmation assay for the compounds identified from primary screen. Briefly, 0.2 µM of Rap1B(1-167) loaded with the fluorescent GDP analog (Mant-GDP), was incubated with EPAC in 50 mM Tris buffer pH 7.5, containing 50 mM NaCl, 5 mM $MgCl_2$, 1 mM DTT, and a 100-fold molar excess of unlabeled GDP (20 µM) in the presence of various concentrations of test compound and 25 µM cAMP. Exchange of Mant-GDP by GDP was measured as a decrease in fluorescence intensity over time using a FluoroMax-3 spectrofluorometer with excitation/emission wavelengths set at 366/450 nm. Typically, decay in the fluorescence intensity was recorded over a time course of 6000 s with data points taken every 60 s.

Counter Screening Assay—

Kinase activity of the type I and II PKA holoenzyme are measured spectrophotometrically in a 96-well plate with a coupled enzyme assay as described previously (Cook et al. (1982) *Biochemistry* 21: 5794-5799). In this assay, the formation of ADP is coupled to the oxidation of NADH by the pyruvate kinase/lactate dehydrogenase reactions so the reaction rate can be determined by following the oxidation of NADH, reflected by a decrease in absorbance at 340 nm. The kinase reaction mixture (100 µl) contains 50 mM Mops (pH 7.0), 10 mM $MgCl_2$, 1 mM ATP, 1 mM PEP, 0.1 mM NADH, 8 U of pyruvate kinase, 15 U of lactate dehydrogenase, fixed amount of type I or type II PKA holoenzyme, and 0.1 mM cAMP, with or without 25 µM of test compound. Reactions are pre-equilibrated at room temperature and initiated by adding the Kemptide substrate (final concentration 0.26 mM). PKA activity measured in the presence of 25 µM H89, a selective PKA inhibitor, are used as a positive control of PKA inhibition.

Once a compound is identified as having an EPAC modulating activity, a number of analogs and variations are designed to produce an EPAC inhibitor with appropriate pharmacologic characteristics.

II. Chemical Definitions

Various chemical definitions related to EPAC modulating compounds are provided as follows.

As used herein, "predominantly one enantiomer" means that the compound contains at least 85% of one enantiomer, or more preferably at least 90% of one enantiomer, or even more preferably at least 95% of one enantiomer, or most preferably at least 99% of one enantiomer. Similarly, the phrase "substantially free from other optical isomers" means that the composition contains at most 5% of another enantiomer or diastereomer, more preferably 2% of another enantiomer or diastereomer, and most preferably 1% of another enantiomer or diastereomer. In certain aspects, one, both, or the predominant enantiomer forms or isomers are all covered.

As used herein, the term "nitro" means —$NO_2$; the term "halo" or "halogen" designates —F, —Cl, —Br or —I; the term "mercapto" means —SH; the term "cyano" means —CN; the term "azido" means —$N_3$; the term "silyl" means —$SiH_3$, and the term "hydroxy" means —OH.

The term "alkyl," by itself or as part of another substituent, means, unless otherwise stated, a linear (i.e. unbranched) or branched carbon chain of 1, 2, 3, 4, 5, 6, 7, 8, 9, or 10 carbons, which may be fully saturated, mono-unsaturated, or polyunsaturated. An unsaturated alkyl group includes those having one or more carbon-carbon double bonds (alkenyl) and those having one or more carbon-carbon triple bonds (alkynyl). The groups, —$CH_3$ (Me, methyl), —$CH_2CH_3$ (Et, ethyl), —$CH_2CH_2CH_3$ (n-Pr, n-propyl), —$CH(CH_3)_2$ (iso-Pr, iso-propyl), —$CH_2CH_2CH_2CH_3$ (n-Bu, n-butyl), —$CH(CH_3)CH_2CH_3$ (sec-butyl), —$CH_2CH$ (CH₃)₂ (iso-butyl), —C(CH₃)₃ (tert-butyl), —CH₂C(CH₃)₃ (neo-pentyl), are all non-limiting examples of alkyl groups.

The term "heteroalkyl," by itself or in combination with another term, means, unless otherwise stated, a linear or branched chain having at least one carbon atom and at least one heteroatom selected from the group consisting of O, N, S, P, and Si. In certain embodiments, the heteroatoms are selected from the group consisting of O, S, and N. The heteroatom(s) may be placed at any interior position of the heteroalkyl group or at the position at which the alkyl group is attached to the remainder of the molecule. Up to two heteroatoms may be consecutive. The following groups are all non-limiting examples of heteroalkyl groups: trifluoromethyl, —CH₂F, —CH₂Cl, —CH₂Br, —CH₂OH, —CH₂OCH₃, —CH₂OCH₂CF₃, —CH₂OC(O)CH₃, —CH₂NH₂, —CH₂NHCH₃, —CH₂N(CH₃)₂, —CH₂CH₂Cl, —CH₂CH₂OH, CH₂CH₂OC(O)CH₃, —CH₂CH₂NHCO₂C(CH₃)₃, and —CH₂Si(CH₃)₃.

The terms "cycloalkyl" and "heterocyclyl," by themselves or in combination with other terms, means cyclic versions of "alkyl" and "heteroalkyl", respectively. Additionally, for heterocyclyl, a heteroatom can occupy the position at which the heterocycle is attached to the remainder of the molecule. Examples of cycloalkyl groups include cyclopropyl, cyclobutyl, cyclopentyl, cyclohexyl, and cycloheptyl groups. Examples of heterocyclic groups include indole, azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, hexahydrodiazepinyl, 4-piperidonyl, pyridyl, pyrazinyl, pyrimidinyl, pyridazinyl, triazinyl, triazolyl, tetrazolyl, tetrahydropyranyl, morpholinyl, thiamorpholinyl, thiamorpholinyl sulfoxide, thiamorpholinyl sulfone, 1,3-dioxolane, tetrahydro-1,1-dioxothienyl, and the like.

The term "aryl" means a polyunsaturated, aromatic, hydrocarbon substituent. Aryl groups can be monocyclic or polycyclic (e.g., 2 to 3 rings that are fused together or linked covalently). The term "heteroaryl" refers to an aryl group that contains one to four heteroatoms selected from N, O, and S. A heteroaryl group can be attached to the remainder of the molecule through a carbon or heteroatom. Non-limiting examples of aryl and heteroaryl groups include phenyl, 4-azaindole, 5-azaindole, 6-azaindole, 7-azaindole, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

Various groups are described herein as substituted or unsubstituted (i.e., optionally substituted). Optionally substituted groups may include one or more substituents independently selected from: halogen, nitro, cyano, hydroxy, amino, mercapto, formyl, carboxy, oxo, carbamoyl, substituted or unsubstituted alkyl, substituted or unsubstituted heteroalkyl, alkoxy, alkylthio, alkylamino, (alkyl)₂amino, alkylsulfinyl, alkylsulfonyl, arylsulfonyl, substituted or unsubstituted cycloalkyl, substituted or unsubstituted heterocyclyl, substituted or unsubstituted aryl, and substituted or unsubstituted heteroaryl. In certain aspects the optional substituents may be further substituted with one or more substituents independently selected from: halogen, nitro, cyano, hydroxy, amino, mercapto, formyl, carboxy, carbamoyl, unsubstituted alkyl, unsubstituted heteroalkyl, alkoxy, alkylthio, alkylamino, (alkyl)₂amino, alkylsulfinyl, alkylsulfonyl, arylsulfonyl, unsubstituted cycloalkyl, unsubstituted heterocyclyl, unsubstituted aryl, or unsubstituted heteroaryl. Examples of optional substituents include, but are not limited to: —OH, oxo (=O), —Cl, —F, —Br, $C_{1-4}$alkyl, phenyl, benzyl, —NH₂, —NH($C_{1-4}$alkyl), —N($C_{1-4}$alkyl)₂, —NO₂, —S($C_{1-4}$alkyl), —SO₂($C_{1-4}$alkyl), —CO₂($C_{1-4}$alkyl), and —O($C_{1-4}$alkyl).

The term "alkoxy" means a group having the structure —OR', where R' is an optionally substituted alkyl or cycloalkyl group. The term "heteroalkoxy" similarly means a group having the structure —OR, where R is a heteroalkyl or heterocyclyl.

The term "amino" means a group having the structure —NR'R", where R' and R" are independently hydrogen or an optionally substituted alkyl, heteroalkyl, cycloalkyl, or heterocyclyl group. The term "amino" includes primary, secondary, and tertiary amines.

The term "oxo" as used herein means oxygen that is double bonded to a carbon atom.

The term "pharmaceutically acceptable salts," as used herein, refers to salts of compounds of this invention that are substantially non-toxic to living organisms. Typical pharmaceutically acceptable salts include those salts prepared by reaction of a compound of this invention with an inorganic or organic acid, or an organic base, depending on the substituents present on the compounds of the invention.

Non-limiting examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydro fluoride, acetate, propionate, formate, oxalate, citrate, lactate, p-toluenesulfonate, methanesulfonate, maleate, and the like.

Suitable pharmaceutically acceptable salts may also be formed by reacting the agents of the invention with an organic base, such as methylamine, ethylamine, ethanolamine, lysine, ornithine and the like. Pharmaceutically acceptable salts include the salts formed between carboxylate or sulfonate groups found on some of the compounds of this invention and inorganic cations, such as sodium, potassium, ammonium, or calcium, or such organic cations as isopropylammonium, trimethylammonium, tetramethylammonium, and imidazolium.

It should be recognized that the particular anion or cation forming a part of any salt of this invention is not critical, so long as the salt, as a whole, is pharmacologically acceptable.

Additional examples of pharmaceutically acceptable salts and their methods of preparation and use are presented in Handbook of Pharmaceutical Salts: Properties, Selection and Use (2002), which is incorporated herein by reference.

An "isomer" of a first compound is a separate compound in which each molecule contains the same constituent atoms as the first compound, but where the three dimensional configuration of those atoms differs. Unless otherwise specified, the compounds described herein are meant to encompass their isomers as well. A "stereoisomer" is an isomer in which the same atoms are bonded to the same other atoms, but where the configuration of those atoms in three dimensions differs. "Enantiomers" are stereoisomers that are mirror images of each other, like left and right hands. "Diastereomers" are stereoisomers that are not enantiomers.

It is contemplated that any embodiment discussed in this specification can be implemented with respect to any method or composition of the invention, and vice versa. Furthermore, compositions of the invention can be used to achieve methods of the invention.

III. Methods of Using EPAC Modulators

Cyclic adenosine monophosphate (cAMP) is an important component of cell-signaling networks that control numerous biological processes. More than a decade of extensive studies have now firmly established that many cAMP-related cellular processes, previously thought to be controlled by PKA alone, are also mediated by EPAC (Gloerich and Bos, (2010) *Annu Rev Pharmacol Toxicol* 50:355-375). For example, EPAC proteins have been implicated in regulating exocytosis and secretion (Ozaki et al. (2000) *Nat Cell Biol* 2:805-811; Seino and Shibasaki (2005) *Physiol Rev* 85:1303-1342; Maillet et al. (2003) *Nat Cell Biol* 5:633-639; Li et al. (2007) *Mol Endocrinol* 21:159-171), cell adhesion (Enserink et al. (2004) *J Biol Chem* 279:44889-44896; Rangarajan et al. (2003) *J Cell Biol* 160:487-493), endothelial barrier junctions (Cullere et al. (2005) *Blood* 105:1950-1955; Kooistra et al. (2005) *FEBS Lett* 579:4966-4972), leptin signaling, and cardiac functions (Metrich et al. (2010) *Pflugers Arch* 459:535-546). In addition to its regulatory functions under physiological conditions, cAMP has been implicated in playing a major role in multiple human diseases, including cancer, diabetes, heart failure, and neurological disorders, such as Alzheimer's disease (AD). The EPAC1 and/or EPAC2 modulating compounds described herein can be used to provide treatment for a variety of diseases or conditions associated with EPAC activation or inhibition.

A. Cancer Therapy

Certain aspects are directed to treating cancer or cancer metastasis in a subject by administering an EPAC inhibitor.

Like PKA, EPAC contains an evolutionarily conserved cAMP-binding domain that acts as a molecular switch for sensing intracellular levels of the second messenger cAMP, and activates the down-stream signaling molecules small GTPases Rap1 and Rap2 (de Rooij et al. (1998) *Nature* 396:474-477; Kawasaki et al. (1998) *Science* 282:2275-2279). In addition, EPAC proteins exert their functions through interactions with other cellular partners at specific cellular locations. For example, EPAC1 is known to associated with mitotic spindle, plasma membrane and nuclear membrane by interacting with tubulin (Qiao et al. (2002) *J Biol Chem* 277:26581-26586; Mei and Cheng (2005) *J Biol Chem* 277:11497-11504), ezrin-radixin-moesin (ERM) proteins (Gloerich et al. (2010) *Mol Cell Biol* 30:5421-5431; Ross et al. (2011) *J Cell Sci* 124:1808-1818) and nucleoporin RanBP2 (Liu et al. (2010) *Mol Cell Biol* 30:3956-3969; Gloerich et al. (2011) *J Cell Biol* 193:1009-1020), respectively. On the other hand, EPAC2 can interact with Rim (Rab3 interacting molecule) and Rim2 (Kashima et al. (2001) *J Biol Chem* 276:46046-46053; Ozaki et al. (2000) *Nat Cell Biol* 2:805-811), as well as a structurally related calcium sensor Piccolo (Fujimoto et al. (2002) *J Biol Chem* 277:50497-50502). In pancreatic beta cells, interactions among EPAC2, Rim2 and Piccolo are critical for cAMP-mediated insulin secretion (Ozaki et al. (2000) *Nat Cell Biol* 2:805-811; Kashima et al. (2001) *J Biol Chem* 276:46046-46053; Fujimoto et al. (2002) *J Biol Chem* 277:50497-50502).

Pancreatic ductal adenocarcinoma (PDAC) is one of the most lethal human diseases, largely due to the fact that pancreatic cancer is resistant to treatments that are usually effective for other types of cancer. A better understanding of the molecular mechanism of PDAC development and metastasis and effective therapeutics are desperately needed. Recently, it has been shown that EPAC1 is markedly elevated in human PDAC cells as compared with normal pancreas or surrounding tissue (Lorenz et al. (2008) *Pancreas* 37:102-103). EPAC1 has been implicated in promoting cellular proliferation in prostate cancer (Misra and Pizzo (2009) *J Cell Biochem* 108:998-1011; Misra and Pizzo (2011) *J Cell Biochem* 112(6):1685-95) and migration and metastasis in melanoma (Baljinnyam et al. (2011) *Pigment Cell Melanoma Res* 24:680-687; Baljinnyam et al. (2009) *Am J Physiol Cell Physiol* 297:C802-C813; Baljinnyam et al. (2010) *Cancer Res* 70:5607-5617).

EPAC inhibitor ESI-09 is used to demonstrate a functional role for EPAC1 overexpression in pancreatic cancer cell migration and invasion. These findings are consistent with similar results based on RNAi silencing techniques, suggesting that EPAC 1 is a target for therapeutic strategies in PDAC and other cancers.

In certain embodiments an EPAC inhibitor can be administered for the treatment of cancer. In certain aspects the cancer is pancreatic cancer, prostate cancer, melanoma, bladder cancer, blood cancer, bone cancer, brain cancer, breast cancer, colorectal cancer, esophageal cancer, gastrointestinal cancer, liver cancer, lung cancer, nasopharynx cancer, ovarian cancer, stomach cancer, testicular cancer, or uterine cancer. In still a further aspect the cancer is pancreatic cancer, particularly pancreatic ductal adenocarcinoma (PDAC). In certain aspects the EPAC inhibitor is selected from the EPAC inhibitors described herein. In a further aspect the EPAC inhibitor is an EPAC 1 inhibitor.

B. Immune Modulator

Certain methods are directed to modulating the innate or adaptive immune system of a subject by administering an EPAC modulator. In a further aspect, methods include enhancing an immune response in a subject by administering an EPAC inhibitor. The immune response can be directed to microbes (fungi, virus, bacteria, and the like); abnormal or aberrantly functioning cells, such as cancer cells or hypersensitive immune effectors; or other pathological conditions that would benefit from an enhanced immune response. Immune modulation is a critical aspect for the treatment of a number of diseases and disorders. T cells in particular play a vital role in fighting infections and have the capability to recognize and destroy cancer cells. Enhancing T cell mediated responses is a key component to enhancing responses to a number of therapeutic agents.

Cyclic AMP is a potent negative regulator of T-cell mediated immunity as it inhibits T-cell proliferation, activation, cytotoxic function, and production of Th1 pro-inflammatory cytokines (Mosenden and Taskén (2011) *Cell Signal* 23, 1009-16; Vang et al. (2001) *J Exp Med* 193, 497-507; Skalhegg et al. (1992) *J Biol Chem* 267, 15707-14; Henney et al. (1972) *J Immunol* 108, 1526-34; Kammer (1988) *Immunol Today* 9, 222-9; Hermann-Kleiter et al. (2006) *Blood* 107, 4841-8). EPAC1 and EPAC2 mediates several of the cAMP immunoregulatory effects that were originally ascribed to protein kinase A (Shirshev (2011) *Biochemistry* (Mosc) 76, 981-98; Bryce et al. (1999) *Immunopharmacology* 41, 139-46; Staples et al, (2003) *Immunology* 109, 527-35; Grandoch et al. (2010) *Br J Pharmacol* 159, 265-84). The EPAC1 effector Rap1 is activated in human CD4+CD25+ upon stimulation (Li et al. (2005) *Blood* 106, 3068-73), suggesting EPAC1 exerts broad control over the immune response in addition to regulating specific effector functions of T-cell mediated immunity.

Figure 15:
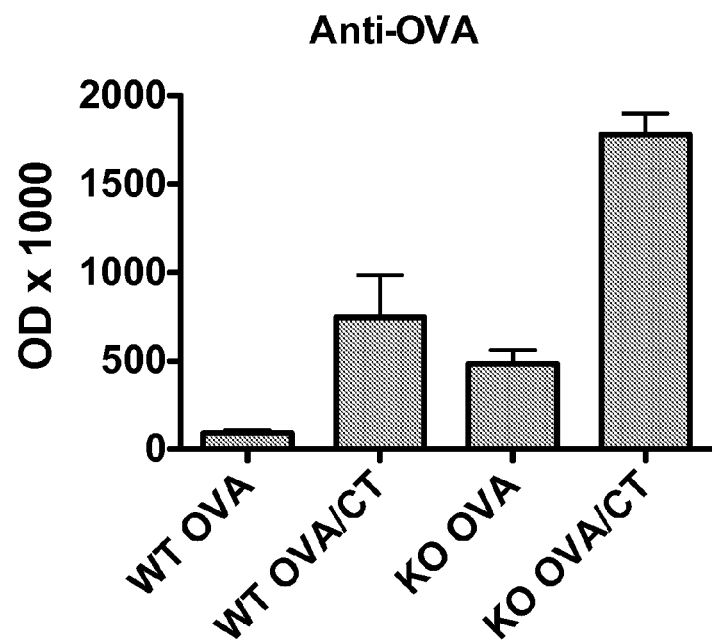
FIG. 15. EPAC1 null mice produce more Ova-IgG antibodies in response to immunization. WT and EPAC1$^{-/-}$ C57BL/6 mice were immunized with ovalbumin (OVA) orally in the presence or absence of cholera toxin (CT). Serum ovalbumin (OVA)-IgG1 level was determined post immunization.
Figure 16:
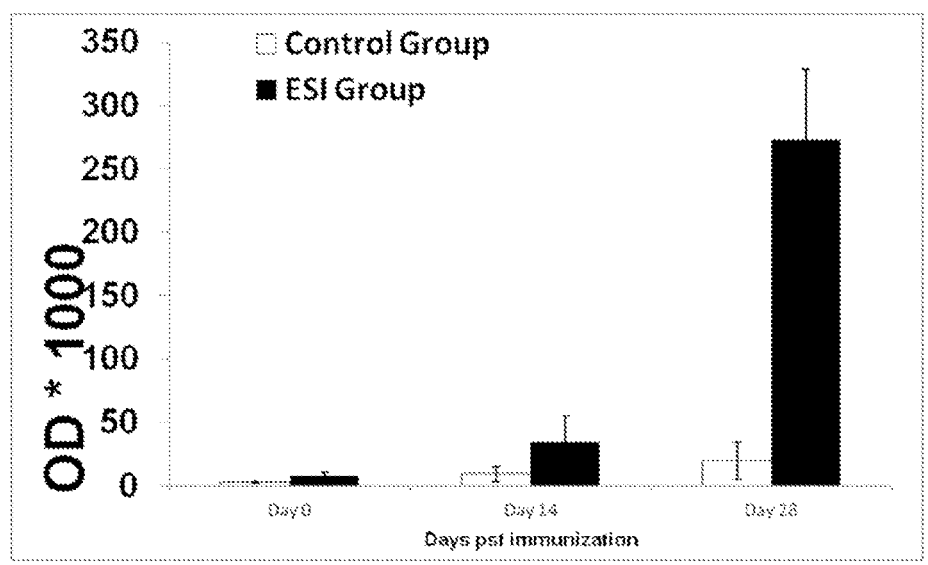
FIG. 16. ESI-09 administration increases serum OVA-IgG1 levels. WT C57BL/6 mice were treated with vehicle or ESI-09 (50 mg/kg, oral gavage) daily. Five days after the treatment, mice were immunized with ovalbumin (OVA) orally and continued ESI-09 daily treatment. Serum ovalbumin (OVA)-IgG1 level was determined 14 and 28 days post immunization.

Several findings support this notion. Transgenic mice expressing a constitutively active Rap1 had lower levels of pro-inflammatory cytokines and an increased fraction of the CD4+CD103+ Tregs subset (including CD4+CD103+ CD25+), which suppressed CD4+CD25− (Tconv) cells more potently than their WT counterparts (Li et al. (2005) *J Immunol* 175, 3133-9). More recently, it was shown that Tregs suppress effector T-cells by direct transfer of cAMP through gap junctions (Fassbender et al. (2010) *Cell Immunol* 265, 91-6; Vignali et al. (2008) *Nat Rev Immunol* 8, 523-32; Somekawa et al. (2005) *Circ Res* 97, 655-62), whose formation in cardiac cells is enhanced by EPAC1 as it facilitates the accumulation of connexons at the site of gap junction formation (Collison and Vignali (2011) *Methods Mol Biol* 707, 21-37). These findings suggest that EPAC1 might play a direct role in contact dependent Treg suppression. To study the in vivo functions of EPAC1, the inventors generated Epac1 knockout (KO) mice. Epac1$^{-/-}$ mice were orally immunized with ovalbumin (OVA) alone or with cholera toxin (CT). In each case Epac1 KO mice had a significantly higher level of serum OVA-specific IgG1 antibodies than that of wild-type (WT) mice as determined by ELISA (FIG. 15). Furthermore, when WT mice were orally immunized with OVA alone or with an EPAC specific antagonist (ESI-09) the mice receiving ESI-09 (oral gavage 50 mg/kg) had a significantly higher level of serum OVA-specific IgG1 antibodies than that of the control group treated with vehicle (FIG. 16).

Based on the amplified immune response in Epac1 KO mice, both antigen-challenged and naïve, it was suggested that a role for Epac1 in mediating the function of CD4+ CD25+ regulatory T-cells (Tregs), which are known suppressors of the adaptive and humoral immune responses. The suppressive potency of WT and Epac1 KO Tregs was examined using an in vitro assay that examines CD4+ CD25− (Tconv) proliferation in the presence Tregs. Epac1 KO Tconv and WT Tconv proliferated at the same rate when cultured alone. The addition of WT Tregs suppressed the proliferation of both cell populations to the same extent, while the addition of Epac1 KO Tregs suppressed the proliferation of Epac1 KO Tconv to a much lesser degree than it did WT Tconv's. To confirm the specificity of Epac1's impact on Tregs mediated suppression of Tconv, the suppression assay was repeated in the presence of ESI-09 and the outcome was similar. Taken together, these results suggest that presence of Epac1 in Tregs and Tconv sensitizes the latter to suppression by the former.

These findings show that EPAC1 antagonists are effective adjuvants and can be used in conjunction with vaccines and immune-modulators for immunotherapies. Such immunotherapies include those for cancer or other diseases. EPAC1 is a viable target for immune-modulation. In particular EPAC1 inhibitors, can be used as adjuvants for vaccines and/or modulators of immunotherapies.

Certain aspects are directed to administering to a subject an EPAC1 inhibitor in conjunction with an antigen. In certain aspects the EPAC1 inhibitor is administered before, during, or after administration of an antigen. In one embodiment, the antigen is a viral protein. In another embodiment, the antigen is a bacterial protein or a portion thereof. In yet another embodiment, the antigen is a mammalian protein or a portion thereof, e.g., a cancer antigen. The antigen can be administered 1, 2, 3, 4, 5, 6, 7, 8, 9, 10, 11, 12, 13, 14, 15, 16, 17, 18, 19, 20, 21, 22, 23, or 24 hours or days before or after EPAC inhibitor administration. The antigen and/or inhibitor can be administered 1, 2, 3, 4, 5, 6, 7, 8 or more times over various time periods. In certain aspects more than one antigen can be administered. In certain aspects the subject is a human subject. In a further embodiment additional immune modulators can be administered.

In certain aspects an EPAC inhibitor is administered in combination with an antibody therapy, which can enhance the efficacy of antibody therapy for treatment of cancer or infectious diseases. The EPAC inhibitor can be administered in combination with antibodies such as rituximab, herceptin or erbitux. In some embodiments, the antibody is an anti-cancer antibody. Monoclonal antibodies, including human and humanized monoclonal antibodies work by targeting tumor specific antigens, thus enhancing the host's immune response to tumor cells. Other antibody therapies include use of polyclonal antibodies and use of antibody fragments or regions. Examples of such therapies are trastuzumab (Herceptin), cetuximab, and rituximab (Rituxan or Mabthera).

Tumor-associated antigens that can be used in the methods of immune modulation include, but are not limited to, 707-AP, Annexin II, AFP, ART-4, BAGE, β-catenin/m, BCL-2, bcr-abl, bcr-abl p190, bcr-abl p210, BRCA-1, BRCA-2, CAMEL, CAP-1, CASP-8, CDC27/m, CDK-4/m, CEA (Huang et al. (2002) *Exper Rev. Vaccines* 1:49-63), CT9, CT10, Cyp-B, Dek-cain, DAM-6 (MAGE-B2), DAM-10 (MAGE-B1), EphA2 (Zantek et al. (1999) *Cell Growth Differ.* 10:629-38; Carles-Kinch et al. (2002) *Cancer Res.* 62:2840-7), ELF2M, ETV6-AML1, G250, GAGE-1, GAGE-2, GAGE-3, GAGE-4, GAGE-5, GAGE-6, GAGE-7B, GAGE-8, GnT-V, gp100, HAGE, HER2/neu, HLA-A*0201-R170I, HPV-E7, HSP70-2M, HST-2, hTERT, hTRT, iCE, inhibitors of apoptosis (e.g. survivin), KIAA0205, K-ras, LAGE, LAGE-1, LDLR/FUT, MAGE-1, MAGE-2, MAGE-3, MAGE-6, MAGE-A1, MAGE-A2, MAGE-A3, MAGE-A4, MAGE-A6, MAGE-A10, MAGE-A12, MAGE-B5, MAGE-B6, MAGE-C2, MAGE-C3, MAGE-D, MART-1, MART-1/Melan-A, MC1R, MDM-2, mesothelin, Myosin/m, MUC1, MUC2, MUM-1, MUM-2, MUM-3, neo-polyA polymerase, NA88-A, NY-ESO-1, NY-ESO-1a (CAG-3), PAGE-4, PAP, Proteinase 3 (Molldrem et al. (1996) *Blood* 88:2450-7; Molldrem et al. (1997) *Blood* 90:2529-34), P15, p190, Pm1/RARα, PRAME, PSA, PSM, PSMA, RAGE, RAS, RCAS1, RU1, RU2, SAGE, SART-1, SART-2, SART-3, SP 17, SPAS-1, TEL/AML 1, TPI/m, Tyrosinase, TARP, TRP-1 (gp75), TRP-2, TRP-2/INT2, WT-1, and alternatively translated NY-ESO-ORF2 and CAMEL proteins.

C. Anti-Infective

In certain aspects EPAC specific inhibitors can be used for attenuating or preventing uptake of a microbe by a vascular endothelial cell. Endothelial and epithelial cell-cell junctions and barriers play a critical role in the dissemination of microbe infection. EPAC and its down-stream effector Rap1 have been shown to play an important role in cellular functions related to endothelial cell junctions and barrier (Kooistra et al. (2005) *FEBS Lett* 579:4966-4972; Baumer et al. (2009) *J Cell Physiol.* 220:716-726; Noda et al. (2010) *Mol Biol Cell* 21:584-596; Rampersad et al. *J. Biol. Chem.* 285:33614-33622; Spindler et al (2011) *Am J Pathol* 178: 2424-2436). In addition, EPAC is known to be involved in phagocytosis (Yeager et al (2009) *Infect Immun* 77:2530-2543; Shirshev (2011) *Biochemistry* (Mosc) 76:981-998).

Cyclic AMP is a universal second messenger that is evolutionarily conserved in diverse form of lives, including human and pathogens such as bacterial, fungi and protozoa. It has been well recognized that cAMP play major roles in microbial virulence, ranging from a potent toxin to a master regulator of virulence gene expression. (MaDonough & Rodriguez (2012) *Nature Rev Microbiol* 10:27-38). As a major intracellular cAMP receptor, it is likely that EPAC proteins are important cellular targets for microbe infection.

Figure 20:
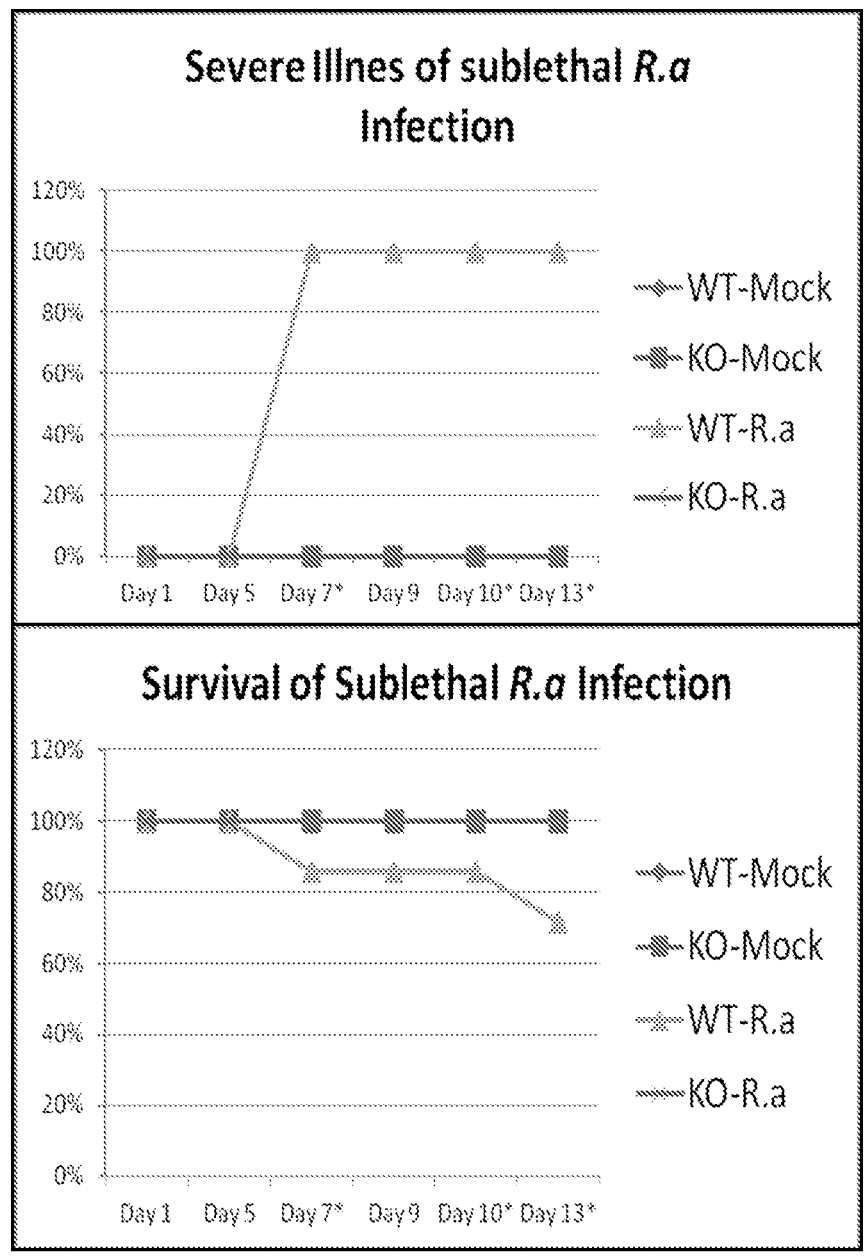
FIG. 20. Deletion of EPAC1 protects mice from sublethal infection of R. australia. WT and EPAC1$^{-/-}$ C57BL/6 mice were challenged with sublethal dose of R. australia. Severity of illness and survival rate were monitored.
Figure 22:
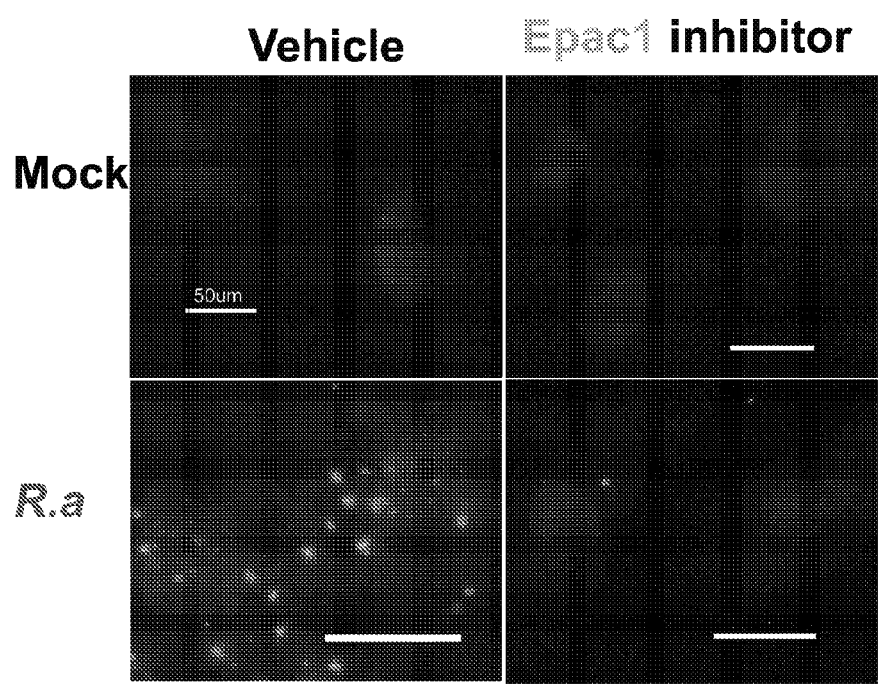
FIG. 22. ESI-09 treatment suppresses cellular entry of R. australia. HUVEC cells treated with vehicle or ESI-09 were infected with R. australia. The levels of R. australia (Red) and EPAC1 (Green) were monitored with immunofluorescence staining 24 hours post infection.

To determine if EPAC 1 plays a role in rickettsia infection, WT and EPAC $1^{-/-}$ C57BL/6 mice were challenged with sublethal dose of *R. australia*. As shown in FIG. 20. All WT mice became severely ill 5 days post infection and a few WT mice died. On the other hand, none of the EPAC1$^{-/-}$ mice became severely sick. These results suggest that deletion of EPAC1 protects mice from *R. australia* infection.

To test if EPAC inhibitors are capable of protecting mice from lethal-dose infection of *R. australia*. WT C57BL/6 mice were treated with vehicle or ESI-09 (10 mg/kg, IP) daily. Five days after the treatment, mice were challenged with lethal dose of *R. australia* and continued ESI-09 daily treatment. Similar to EPAC1 genetic deletion, pharmacological inhibition of EPAC1 also led to a striking protection of *R. Australia* infection (FIG. 21). 100% control group became severely sick while only 10% of the treatment group showed sign of sickness.

To investigate the mechanism of EPAC1 inhibition-mediated protection of *R. australia* infection, HUVEC cells treated with vehicle or ESI-09 were infected with *R. australia*. As shown in FIG. 22, the number of intracellular *R. australia* was dramatically reduced in ESI-09 treated HUVEC cells. These data demonstrate that inhibition of EPAC by ESI-09 treatment suppresses cellular entry of *R. australia.*

Certain embodiments are directed to methods of suppressing microbe infection comprising administering an EPAC specific inhibitor to a subject having or under the risk of microbe infection. In certain aspects the microbe is a bacteria, virus, or fungi. In other aspects the EPAC specific inhibitor is selected from the EPAC inhibitors described herein.

D. Leptin Modulator

In certain aspects, compounds described herein can be used to enhance leptin sensitivity and reduce adiposity in a subject.

The adipocyte hormone leptin plays a central role in energy homeostasis. It was discovered in obese mice missing a serum factor, which when replaced decreased food intake and body weight (Zhang et al. (1994) *Nature* 372: 425-32). Because of these initial observations, much of the earlier therapeutic attempt using this hormone has been in the treatment of obesity. Serum leptin concentrations in the majority of humans with obesity are high, and a state of leptin resistance is thought to exist (Mantzoros et al. (2000) *J Clin Endocrinol Metab* 85:4000-4002). Thus far, the effect of recombinant human leptin has been limited in causing weight loss in obese individuals except in the state of congenital leptin deficiency (Heymsfield et al. (1999) *Jama* 282:1568-75; Farooqi et al. (1999) *N Engl J Med* 341:879-84).

Activation of EPAC has been shown to impair leptin signaling. Central infusion of an EPAC activator has been shown to blunt the anorexigenic actions of leptin (Fukuda et al. (2011) *Cell Metab* 13:331-339). The present invention provides for the use of EPAC modulators for the treatment of diseases related to abnormalities in the leptin pathway, such as obesity and lipoatrophy and its associated metabolic abnormalities (e.g., hyperglycemia, dyslipidemia, hyperlipidemia, hypercholesterolemia, hypertriglyceridemia, atherosclerosis, vascular restenosis, and insulin resistance).

Epac1 Knockout (KO) Mice Display Blunted Body Weight Gain.

Global Epac1 knockout mice were generated using the Cre-loxP system. Epac1 null mutant mice in general appear healthy without any obvious physical abnormalities. They have similar body weights compared to wild-type mice at birth and up to three weeks of age, when the mice were weaned and started on the high fat diet or standard rodent chow. The body weight gain of Epac1 KO mice on standard chow diet slowed down and became significantly lower than that of the wild-type mice around week 5, eventually reaching approximately 85% of wild-type mice. Similar observations were made for the HFD-fed mice. The body weight of Epac1 KO mice became significantly lower around week 7, and maintained at about 90% of wild-type mice. The average daily food intake of Epac1 KO mice on chow diet was significantly lower than that of the wild-type. On the other hand, while the average daily food intake of Epac1 KO mice on HFD was lower than that of the wild-type mice on HFD, the difference was not statistically significant. Whole body micro-CT scans were performed on HFD-fed mice and body length was measured from C1 to L6 vertebrae to confirm that body weight gain lag in Epac1 KO mice is not the result of overall growth retardation.

Epac1 Deficiency Reduces Adiposity.

To determine why body weight gain is reduced in Epac1 KO mice, the adiposity of the animals was examined. The epididymal fat pads from Epac1 KO mice were visually smaller and weighted significantly less than those from wild-type. When analyzed by Micro-CT imaging, the total fat mass of Epac1 null mice on HFD was significantly less than wild-type. This difference was significant even after fat mass was normalized to body weight. In fact, the difference in total fat mass was larger than the difference in body weight, suggesting that the reduced body weight of Epac1 KO mice is mainly due to a reduction in fat mass. A decrease in adipose tissue mass can be the result of impaired adipocyte differentiation, a reduction of adipocyte size, or both. Histological analysis of epididymal white fat tissue (EWAT) revealed that adipocytes from Epac1 null mice were much smaller than those from the wild-type counterparts. On the other hand, ex vivo adipocyte differentiation analyses using MEF cells isolated from both wild-type and Epac1 KO mice revealed that the Epac1 KO MEFs were as competent as wild-type MEFs to differentiate into adipocytes, suggesting that Epac1 deficiency did not impede normal adipogenesis.

Leptin is secreted by adipose tissue and the plasma levels of leptin are known to correlate with adipose tissue mass while plasma leptin falls in both humans and mice after weight loss (Considine et al. (1996) *N. Engl. J. Med.* 441 334:292-295; Friedman and Halaas (1998) *Nature* 395:763-770; Maffei et al. (1995) *Nat. Med.* 1:1155-1161). To investigate if a reduced fat mass is correlated with reduced plasma leptin in Epac1 null mice, the plasma leptin levels of Epac1 KO and wild-type mice on standard chow and HFD were compared, respectively. For mice on the standard chow diet, the average plasma leptin level of 16-week-old wild-type mice was around 3.97±0.78 ng/ml which is consistent with previous publications (Bates et al. (2003) *Nature* 421:856-859; Kievit et al. (2006) *Cell Metab* 4:123-132). However, the plasma leptin level of the age and gender matched Epac1 KO mice was significantly lower, at about 1.01±0.26 ng/ml. For the mice on HFD at 28-weeks of age (25 weeks on HFD), the average leptin concentration was about 83.16±5.76 ng/ml, whereas the average leptin level of Epac1 KO mice was about 66.15±3.52 ng/ml. These results corroborate the anatomical and morphological observation that Epac1 deficiency reduces white fat tissue adiposity in the standard chow diet as well as HFD fed mouse.

To determine if the apparent decreases in plasma leptin levels are merely the result of decreased adiposity, the leptin levels of 3-week-old mice were measured before significant body weight and adiposity difference can be observed between the wild-type and Epac1 mull mice. Leptin levels in Epac1 KO mice were already reduced significantly compared to those in age and gender match wild-type mice.

Loss of Epac1 Heightens Leptin Signaling Activity and Sensitivity In Vivo.

In light of a recent finding by Fukuda, et al. that activation of Epac-RAP1 with Epac selective agonist, 8-pCPT-2'-O-Me-cAMP (8-(4-chlorophenylthio)-2'-O-methyladenosine-3',5'-cyclic mono-phosphorothioate) blunts leptin signaling in hypothalamus and causes central leptin resistance (Fukuda et al. (2011) *Cell Metab* 13:331-339), the pSTAT3 Y705 localization and immunoactivity in the arcuate nucleus (AN), with or without Epac1, was compared to determine the consequence of reduced plasma leptin levels associated with the loss of Epac1 on leptin sensitivity in vivo. The proopiomelanocortin neurons are direct targets of leptin in the hypothalamus and the leptin-induced STAT3 Y705 phosphorylation and nuclear translocation in the AN is involved in body weight regulation (Bates et al. (2003) *Nature* 421: 856-859; Cheung et al. (1997) *Endocrinology* 138:4489-4492; Hubschle et al. (2001) *J. Neurosci.* 21:2413-2424; Schwartz et al. (1996) *J. Clin. Invest* 98:1101-1106). The Epac1 KO AN tissue displayed a slightly enhanced baseline level (PBS vehicle injection) of pSTAT3 Y705 immunoractivity, and a markedly increased nuclear immunostaining of pSTAT3 Y705 in response to ICV injection of leptin than that of the wild-type. To further compare the total pSTAT3 Y705 in the hypothalamus upon stimulation with leptin, we repeated ICV leptin injections and excised the hypothalami for immunoblotting analysis. Consistent with our immunofluorescence study, the basal and the stimulated levels of pSTAT3 Y705 were both increased in the Epac1 KO hypothalamic tissue, suggesting that loss of Epac1 enhances central leptin signaling and sensitivity while decreases peripheral (plasma) leptin levels in vivo.

To investigate if this increased leptin sensitivity associated with loss of Epac1 translates into decreased food intake and body weight in response to leptin in vivo, leptin was injected intraperitoneally to 20-week-old mice. The mice were individually housed for one week to acclimate them with the environment. Escalation of leptin was utilized to cover a wide range of doses (Heymsfield et al. (1999) *JAMA* 282:1568-1575). Due to the nocturnal activity of mice and the short half-life of leptin (Ahren et al. (2000) *Int. J. Obes. Relat Metab Disord.* 24:1579-1585; Hill et al. (1998) *Int. J. Obes. Relat Metab Disord.* 22:765-770), food intake was measured during the first 4-hours of the dark cycle, food intake during the entire 24-hour period, and body weight at the beginning of each dark cycle. It was found that food intake over the first four hours of the dark cycle decreased in a dose-dependent manner in response to leptin administration. Epac1 KO mice displayed a significant reduction in food intake at the higher doses of leptin versus wild-type mice during the first 4-hour dark cycle. Although the 24-hour food intake also decreased with leptin administration, the magnitude of decrease was not statistically significant. Interestingly, leptin injection induced a transient body weight decrease in the wild-type mice which recovered quickly even with highest dose of leptin. In contrast, leptin induced a persistent and dose-dependent body weight reduction in Epac1 KO mice. These results demonstrate that Epac1 deficiency enhances leptin signaling in hypothalamus and that Epac1 KO mice are more sensitive to leptin treatment in vivo in regard to the reduction of food intake and body weight.

Figures 17A, 17B:
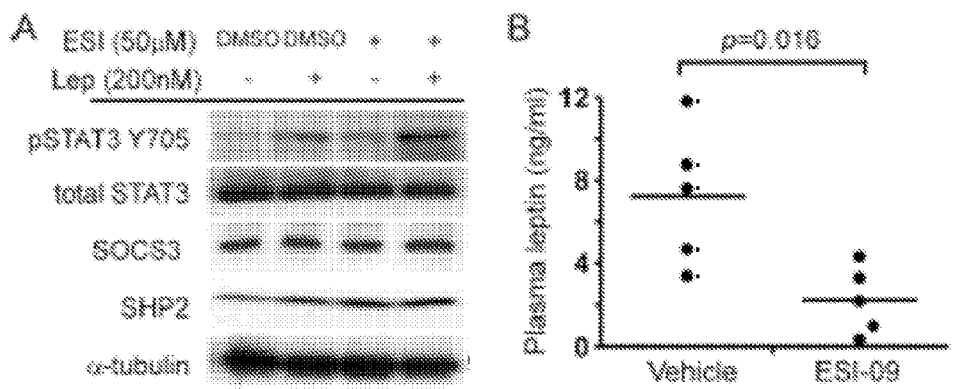
FIGS. 17A-17B. Pharmacological inhibition of EPAC reduces plasma leptin and enhances leptin signaling in hypothalamus (A) Western blotting of pSTAT3 Y705, total STAT3, SOCS3, SHP2 and α-tubulin in organotypic brain slices at hypothalamus level treated with leptin with or without EPAC specific inhibitor. (B) Plasma leptin levels of 8-week-old wild-type mice treated 3 weeks with vehicle or ESI-09 (50 mg/kg).

To explore the feasibility of increasing leptin sensitivity by targeting Epac1 using small molecules, organotypic brain slice cultures were prepared from 11-day old wild-type C57BL/6 mice. After 7 days ex vivo culture, treatment of the brain tissue with the Epac specific antagonist ESI-09 led to an enhanced pSTAT3 Y705 level both at the basal state and in response to leptin stimulation. Moreover, Epac specific inhibitors also increased the cellular level of SHP2 as observed in the Epac1 KO mice (FIG. 17A). These pharmacological data are in agreement with results obtained using Epac1 KO mice and further confirm that inhibition of Epac1 enhances leptin signaling in the hypothalamus. To further investigate the therapeutic potential of this small molecule, wild-type mice were with ESI-09 (50 mg/kg) or vehicle (corn oil) by oral gavage for 3 weeks. Plasma leptin was significantly reduced after ESI-09 relative to vehicle treatment (FIG. 17B).

Epac1 KO Mice are Protected Against HFD Induced Glucose Intolerance.

Figures 18A, 18B, 18C, 18D:
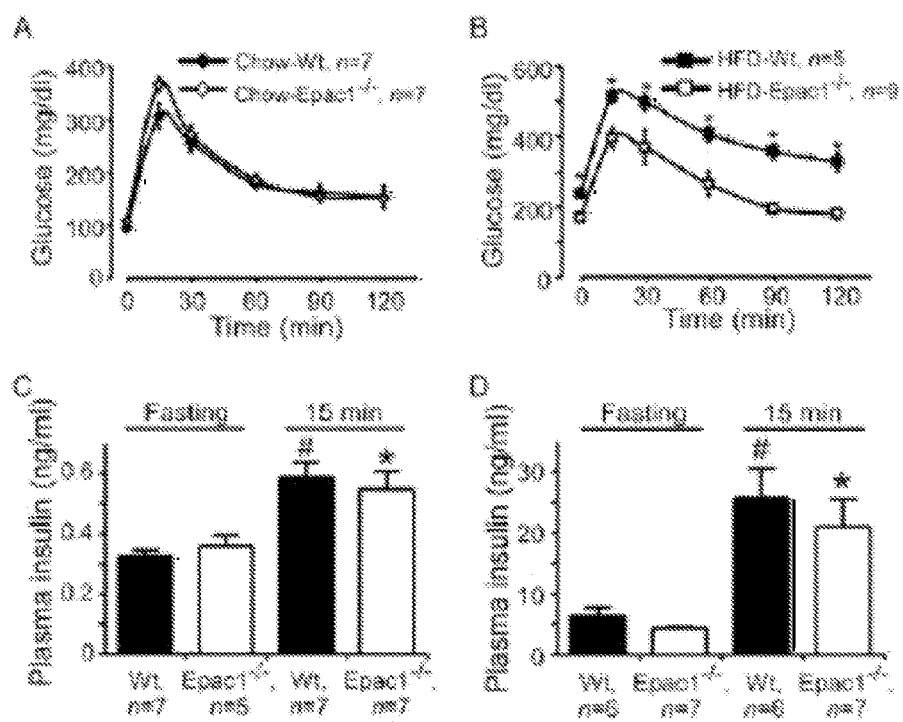
FIGS. 18A-18D. Epac1$^{-/-}$ (KO) mice are protected against HFD-induced glucose intolerance. (A) Oral glucose tolerance test of 18-week-old chow fed mice. (B) Oral glucose tolerance test of 18-week-old HFD fed mice (15 weeks on HFD). (C) Insulin levels after fasting and 15 min after glucose administration (1 g/kg BW) in chow fed 18-week-old mice. (D) Insulin levels after fasting and 15 min after glucose administration (1 g/kg BW) in 18-week-old HFD fed mice. Data are mean 631±SEM. #compare with wild-type fasting, p<0.05, * compare with Epac1$^{-/-}$ fasting, p<0.05.

It has been well documented that enhanced leptin sensitivity confers resistance to HFD-induced obesity and improved glucose tolerance (Berglund et al. (2012) *J. Clin. Invest* 122:1000-1009; Howard et al. (2004) *Nat. Med.* 10:734-738; Kievit et al. (2006) *Cell Metab* 4:123-132; Mori (2004) *Nat. Med.* 522 10:739-743). The glucose handling capability of wild-type and Epac1 KO mice were compared using the oral glucose tolerance test (OGTT). While similar OGTT results were obtained for wild-type and Epac1 KO mice on the standard chow diet (FIG. 18A), the Epac1 KO mice displayed a markedly enhanced glucose handling capability after 15 weeks on HFD. Firstly, the fasting glucose levels of HFD Epac1 KO mice were significantly lower than those of wild-type; secondly, Epac1 KO mice cleared glucose from blood significantly faster than wild-type mice at every time point after glucose administration. The blood glucose levels of Epac1 KO mice dropped back to baseline in 2 hours while the wild-type blood glucose levels remained elevated (FIG. 18B). In parallel, insulin levels were monitored after overnight fasting and 15 min after glucose administration. No significant differences were observed between wild-type and Epac1 KO mice on the standard chow diet: both showed similar low fasting insulin levels that increased to a similar extent in response to glucose challenge (FIG. 18C). On the other hand, while HFD Epac KO mice showed a slightly decreased fasting insulin level, both HFD wild-type and Epac1 KO mice maintained the ability to increasing plasma insulin in response to blood glucose concentration elevation (FIG. 18D). These data suggest that Epac1 KO mice are resistant to HFD-induced insulin insensitivity as in the case of the wild-type mice. These studies show that Epac1 KO mutant mice are largely protected from the HFD-induced glucose intolerance and insulin resistance.

In certain aspects, an EPAC inhibitor is administered to a leptin-resistant subject. The administration of an EPAC inhibitor increases sensitivity of the subject to endogenous leptin. In a further aspect, leptin or leptin analog can be administered in combination with an EPAC inhibitor to overcome leptin resistance or deficiency. In another aspect, an overweight subject is administered an EPAC inhibitor reducing body weight of the subject. In yet another aspect, an EPAC inhibitor is administered to increase systemic insulin sensitivity. Other aspects include administering an EPAC activator to a subject having anorexic or cachexic symptoms or syndromes, or a hypersensitivity to leptin.

IV. Pharmaceutical Formulations and Administration

In certain embodiments, the invention also provides compositions comprising one or more EPAC modulator with one or more of the following: a pharmaceutically acceptable diluent; a carrier; a solubilizer; an emulsifier; a preservative; and/or an adjuvant. Such compositions may contain an effective amount of at least one EPAC modulator. Thus, the use of one or more EPAC modulators as provided herein for the preparation of a medicament is also included. Such compositions can be used in the treatment of a variety of EPAC associated diseases or conditions such as cancer or leptin associated disease or conditions.

An EPAC modulator may be formulated into therapeutic compositions in a variety of dosage forms such as, but not limited to, liquid solutions or suspensions, tablets, pills, powders, suppositories, polymeric microcapsules or microvesicles, liposomes, and injectable or infusible solutions. The preferred form depends upon the mode of administration and the particular disease targeted. The compositions also preferably include pharmaceutically acceptable vehicles, carriers, or adjuvants, well known in the art.

Acceptable formulation components for pharmaceutical preparations are nontoxic to recipients at the dosages and concentrations employed. In addition to the EPAC modulating agents, compositions may contain components for modifying, maintaining, or preserving, for example, the pH, osmolarity, viscosity, clarity, color, isotonicity, odor, sterility, stability, rate of dissolution or release, adsorption, or penetration of the composition. Suitable materials for formulating pharmaceutical compositions include, but are not limited to, amino acids (such as glycine, glutamine, asparagine, arginine or lysine); antimicrobials; antioxidants (such as ascorbic acid, sodium sulfite or sodium hydrogen-sulfite); buffers (such as acetate, borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counter ions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (see *Remington's Pharmaceutical Sciences,* 18 th Ed., (A. R. Gennaro, ed.), 1990, Mack Publishing Company), hereby incorporated by reference.

Formulation components are present in concentrations that are acceptable to the site of administration. Buffers are advantageously used to maintain the composition at physiological pH or at a slightly lower pH, typically within a pH range of from about 4.0 to about 8.5, or alternatively, between about 5.0 to 8.0. Pharmaceutical compositions can comprise TRIS buffer of about pH 6.5-8.5, or acetate buffer of about pH 4.0-5.5, which may further include sorbitol or a suitable substitute therefor.

The pharmaceutical composition to be used for in vivo administration is typically sterile. Sterilization may be accomplished by filtration through sterile filtration membranes. If the composition is lyophilized, sterilization may be conducted either prior to or following lyophilization and reconstitution. The composition for parenteral administration may be stored in lyophilized form or in a solution. In certain embodiments, parenteral compositions are placed into a container having a sterile access port, for example, an intravenous solution bag or vial having a stopper pierceable by a hypodermic injection needle, or a sterile pre-filled syringe ready to use for injection.

The above compositions can be administered using conventional modes of delivery including, but not limited to, intravenous, intraperitoneal, oral, intralymphatic, subcutaneous administration, intraarterial, intramuscular, intrapleural, intrathecal, and by perfusion through a regional catheter. Local administration to an organ or a tumor is also contemplated by the present invention. When administering the compositions by injection, the administration may be by continuous infusion or by single or multiple boluses. For parenteral administration, the EPAC modulating agents may be administered in a pyrogen-free, parenterally acceptable aqueous solution comprising the desired EPAC modulating agents in a pharmaceutically acceptable vehicle. A particularly suitable vehicle for parenteral injection is sterile distilled water in which one or more EPAC modulating agents are formulated as a sterile, isotonic solution, properly preserved.

Once the pharmaceutical composition of the invention has been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

If desired, stabilizers that are conventionally employed in pharmaceutical compositions, such as sucrose, trehalose, or glycine, may be used. Typically, such stabilizers will be added in minor amounts ranging from, for example, about 0.1% to about 0.5% (w/v). Surfactant stabilizers, such as TWEEN®-20 or TWEEN®-80 (ICI Americas, Inc., Bridgewater, N.J., USA), may also be added in conventional amounts.

Figure 19:
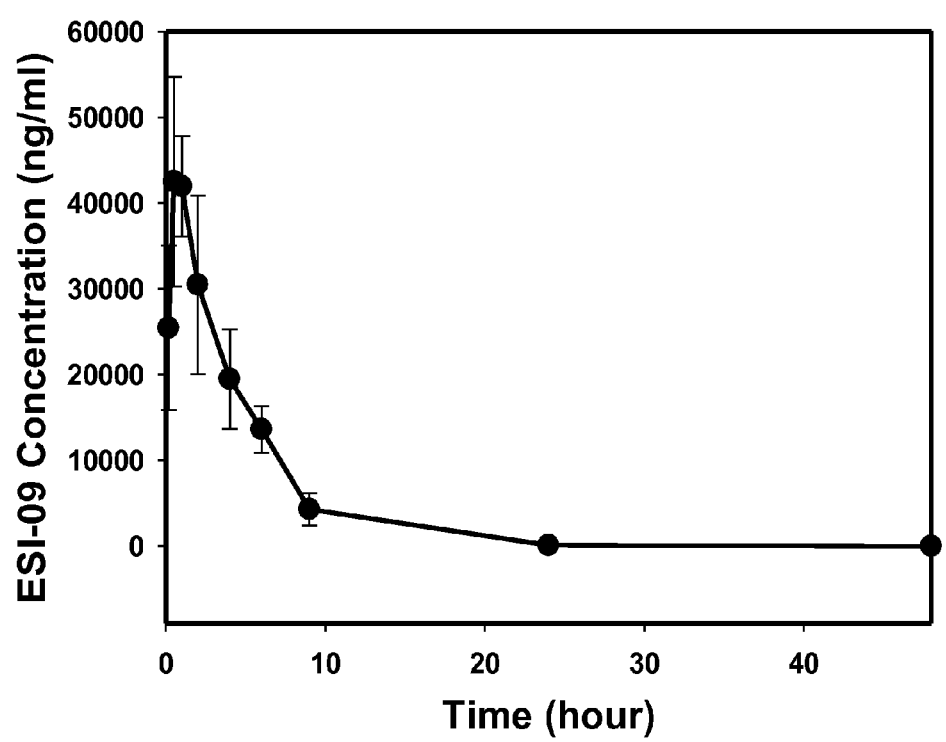
FIG. 19. Mice blood time-concentration curve of ESI-09. Following one single intraperitoneal (IP) injection of the ESI-09 compound (10 mg/kg) in mice (n=5 for each time point), blood levels of ESI-09 were determined to be rapidly elevated reaching maximal values of 42,520 ng/ml (128 µM) at 0.5 hr with a half-life of 3.5 hrs.

To determine the bioavailability of EPAC inhibitors, an IP injection formulation was developed in which the compounds were dissolved in ethanol and then diluted 1:10 with a 10% Tween 80 in normal saline solution. This formulation was determined suitable by passing the simulated in vivo blood dilution assay. In vivo pharmacokinetic studies were performed in four week old female C57BL6/N mice. As shown in FIG. 19, following one single intraperitoneal (IP) injection of the ESI-09 compound (10 mg/kg) in mice (n=5 for each time point), blood levels of ESI-09 were determined to be rapidly elevated reaching maximal values of 42,520 ng/ml (128 µM) at 0.5 hr with a half-life of 3.5 hrs. These results suggest that ESI-09 has an excellent bioactivity in vivo.

For the compounds of the present invention, alone or as part of a pharmaceutical composition, such doses are between about 0.001 mg/kg and 1 mg/kg body weight, preferably between about 1 and 100 µg/kg body weight, most preferably between 1 and 10 µg/kg body weight.

Therapeutically effective doses will be easily determined by one of skill in the art and will depend on the severity and course of the disease, the patient's health and response to treatment, the patient's age, weight, height, sex, previous medical history and the judgment of the treating physician.

In some methods of the invention, an EPAC inhibitor is administered to a cancer cell. The cancer cell may be in a patient and the patient may have a solid tumor. In such cases, embodiments may further involve performing surgery on the patient, such as by resecting all or part of the tumor. Compositions may be administered to the patient before, after, or at the same time as surgery. In additional embodiments, patients may also be administered directly, endoscopically, intratracheally, intratumorally, intravenously, intralesionally, intramuscularly, intraperitoneally, regionally, percutaneously, topically, intrarterially, intravesically, or subcutaneously. Therapeutic compositions may be administered 1, 2, 3, 4, 5, 6, 7, 8, 9, 10, 11, 12, 13, 14, 15, 16, 17, 18, 19, 20 or more times, and they may be administered every 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months.

Methods of treating cancer may further include administering to the patient chemotherapy or radiotherapy, which may be administered more than one time. Chemotherapy includes, but is not limited to, cisplatin (CDDP), carboplatin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, taxotere, taxol, transplatinum, 5-fluorouracil, vincristin, vinblastin, methotrexate, gemcitabine, oxaliplatin, irinotecan, topotecan, or any analog or derivative variant thereof. Radiation therapy includes, but is not limited to, X-ray irradiation, UV-irradiation, γ-irradiation, electron-beam radiation, or microwaves. Moreover, a cell or a patient may be administered a microtubule stabilizing agent, including, but not limited to, taxane, as part of methods of the invention. It is specifically contemplated that any of the compounds or derivatives or analogs, can be used with these combination therapies.

V. Examples

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

4-Cyclohexyl-2-Mercapto-6-Oxo-1,6-Dihydro-Pyrimidine-5-Carbonitrile (HJC-1-61)

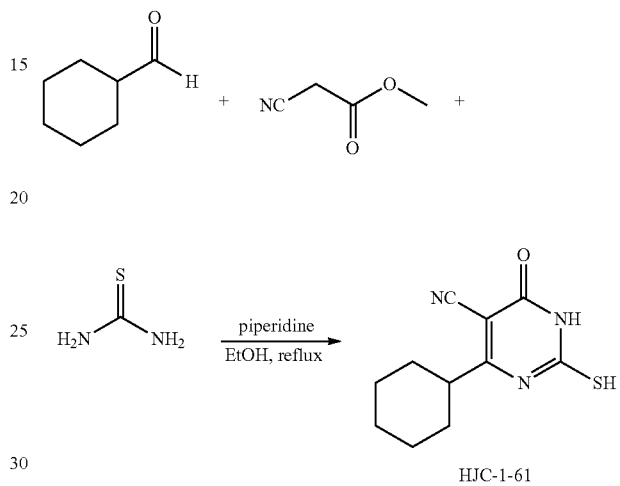

HJC-1-61

To a solution of cyclohexanecarbaldehyde (1.12 g, 10.0 mmol), methyl cyanoacetate (0.99 g, 10 mmol), and thiourea (0.76 g, 10 mmol) in absolute ethanol (50 mL) was added piperidine (1.70 g, 20 mmol). The mixture was heated under reflux for 6 h and then cooled to room temperature. The solution was concentrated and then the residue was extracted with ethyl acetate (100 mL) and 2N HCl (aq.) (20 mL). The organic layer was isolated, washed with brine, and dried over anhydrous $Na_2SO_4$. The solvent was evaporated under reduced pressure, and the product was washed with EtOAc (30 mL) to obtain the pure product as a white solid (1.2 g, 51%). $^1$H NMR (600 MHz, DMSO-$d_6$) δ 13.04 (s, 1H), 12.73 (s, 1H), 2.73-2.71 (m, 1H), 1.86-1.79 (m, 4H), 1.73-1.71 (m, 2H), 1.66-1.63 (m, 1H), 1.29-1.20 (m, 3H).

Example 2

2-Mercapto-4-(1-Methyl-Piperidin-4-Yl)-6-Oxo-1,6-Dihydro-Pyrimidine-5-Carbonitrile (HJC-1-83)

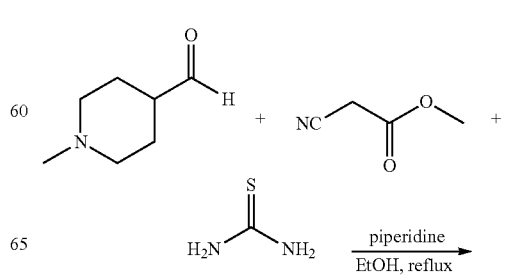

-continued

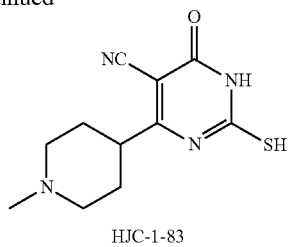

HJC-1-83

To a solution of 1-methylpiperidine-4-carbaldehyde (600 mg, 4.72 mmol), methyl cyanoacetate (468 mg, 4.72 mmol), and thiourea (359 mg, 4.72 mmol) in absolute ethanol (25 mL) was added piperidine (803 mg, 9.44 mmol). The mixture was heated under reflux for 6 h and then cooled to room temperature. The precipitate was collected by filtration and washed with DCM (10 mL) and EtOAc (10 mL). The desired product was obtained as a pale yellow solid (820 mg, 69%) and used directly for the next step without further characterization.

Example 3

4-(5-Cyano-2-Mercapto-6-Oxo-1,6-Dihydro-Pyrimidin-4-Yl)-Piperidine-1-Carboxylic Acid Tert-Butyl Ester (HJC-1-89)

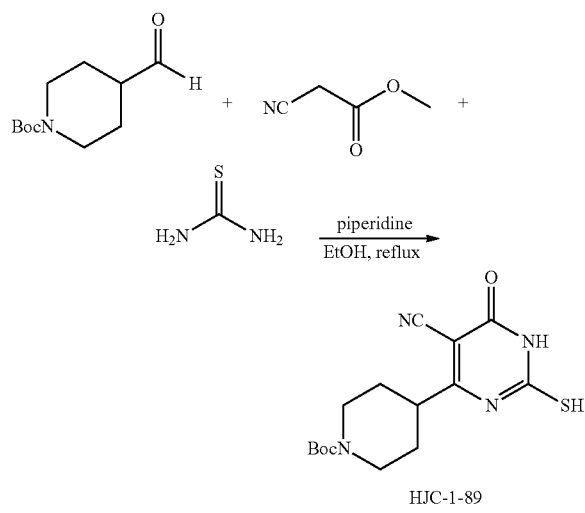

HJC-1-89

To a solution of 4-formyl-piperidine-1-carboxylic acid tert-butyl ester (600 mg, 2.82 mmol), methyl cyanoacetate (280 mg, 2.82 mmol), and thiourea (215 mg, 2.82 mmol) in absolute ethanol (25 mL) was added piperidine (480 mg, 5.63 mmol). The mixture was heated under reflux for 6 h and then cooled to room temperature. The solution was concentrated and then the residue was extracted with ethyl acetate (100 mL) and 2N HCl (aq.) (20 mL). The organic layer was isolated, washed with brine, and dried over anhydrous $Na_2SO_4$. The solvent was evaporated under reduced pressure, and the product was washed with EtOAc (5 mL) to obtain the pure product as a white solid (560 mg, 59%). $^1$H NMR (600 MHz, DMSO-d6) δ 13.01 (s, 1H), 12.70 (s, 1H), 4.03-3.94 (m, 2H), 2.87-2.84 (m, 1H), 2.71-2.63 (m, 2H), 1.88-1.85 (m, 4H), 1.67-1.60 (m, 2H), 1.37 (s, 9H).

Example 4

4-Isopropyl-2-Mercapto-6-Oxo-1,6-Dihydro-Pyrimidine-5-Carbonitrile (HJC-1-90)

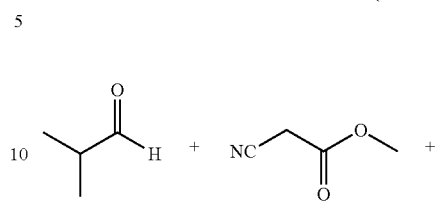

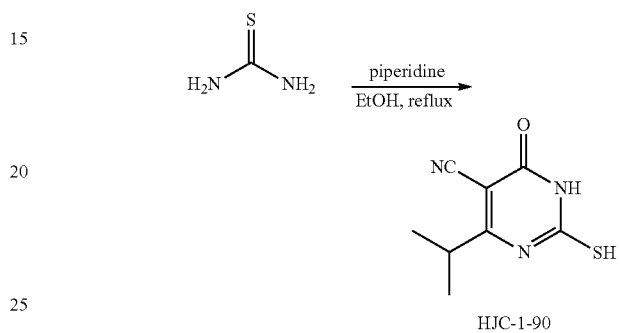

HJC-1-90

To a solution of 2-methyl-propionaldehyde (1.0 g, 13.9 mmol), methyl cyanoacetate (1.37 g, 13.9 mmol), and thiourea (1.06 g, 13.9 mmol) in absolute ethanol (45 mL) was added piperidine (2.37 g, 27.8 mmol). The mixture was heated under reflux for 6 h and then cooled to room temperature. The solution was concentrated and then the residue was extracted with ethyl acetate (100 mL) and 2N HCl (aq., 20 mL). The organic layer was isolated, washed with brine, and dried over anhydrous $Na_2SO_4$. The solvent was evaporated under reduced pressure, and the product was washed with EtOAc (20 mL) to obtain the pure product as a pale yellow solid (1.5 g, 55%). $^1$H NMR (600 MHz, DMSO-d6) δ 13.07 (s, 1H), 12.78 (s, 1H), 3.05-3.01 (m, 1H), 1.30 (d, 6H, J=7.2 Hz).

Example 5

4-Cyclopentyl-2-Mercapto-6-Oxo-1,6-Dihydro-Pyrimidine-5-Carbonitrile (HJC-1-91)

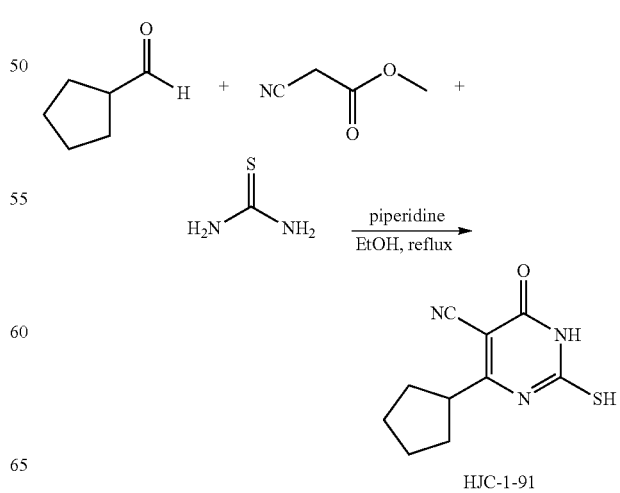

HJC-1-91

To a solution of cyclopentanecarbaldehyde (500 mg, 5.1 mmol), methyl cyanoacetate (504 mg, 5.1 mmol), and thiourea (388 mg, 5.1 mmol) in absolute ethanol (20 mL) was added piperidine (868 mg, 10.2 mmol). The mixture was heated under reflux for 6 h and then cooled to room temperature. The solution was concentrated and then the residue was extracted with ethyl acetate (100 mL) and 2N HCl (aq., 20 mL). The organic layer was isolated, washed with brine, and dried over anhydrous $Na_2SO_4$. The solvent was evaporated under reduced pressure, and the product was washed with EtOAc (10 mL) to obtain the pure product as a pale yellow solid (700 mg, 62%). $^1$H NMR (600 MHz, DMSO-d6) δ 13.05 (s, 1H), 12.86 (s, 1H), 3.09-3.06 (m, 1H), 1.99-1.96 (m, 2H), 1.89-1.82 (m, 4H), 1.65-1.62 (m, 2H).

Example 6

4-Cyclopropyl-2-Mercapto-6-Oxo-1,6-Dihydro-Pyrimidine-5-Carbonitrile (HJC-1-92)

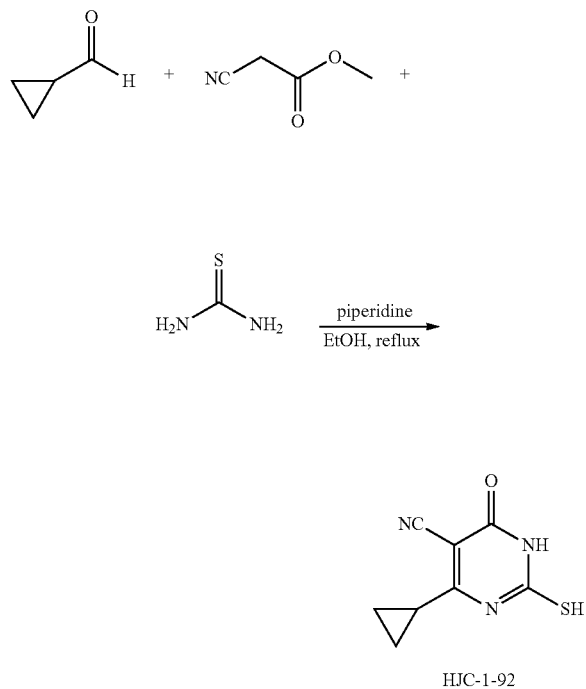

HJC-1-92

To a solution of cyclopropanecarbaldehyde (500 mg, 7.13 mmol), methyl cyanoacetate (706 mg, 7.13 mmol), and thiourea (543 mg, 7.13 mmol) in absolute ethanol (15 mL) was added piperidine (1.21 g, 14.27 mmol). The mixture was heated under reflux for 6 h and then cooled to room temperature. The solution was concentrated and then the residue was extracted with ethyl acetate (100 mL) and 2N HCl (aq., 20 mL). The organic layer was isolated, washed with brine, and dried over anhydrous $Na_2SO_4$. The solvent was evaporated under reduced pressure, and the product was washed with EtOAc (5 mL) to obtain the pure product as a yellow solid (250 mg, 18%). $^1$H NMR (600 MHz, DMSO-d6) δ 12.84 (s, 1H), 12.50 (bs, 1H), 2.01-1.99 (m, 1H), 1.32-1.30 (m, 2H), 1.17-1.16 (m, 2H).

Example 7

4-Cyclohexyl-2-(2,5-Dimethyl-Benzylsulfanyl)-6-Oxo-1,6-Dihydro-Pyrimidine-5-Carbonitrile (HJC-1-65)

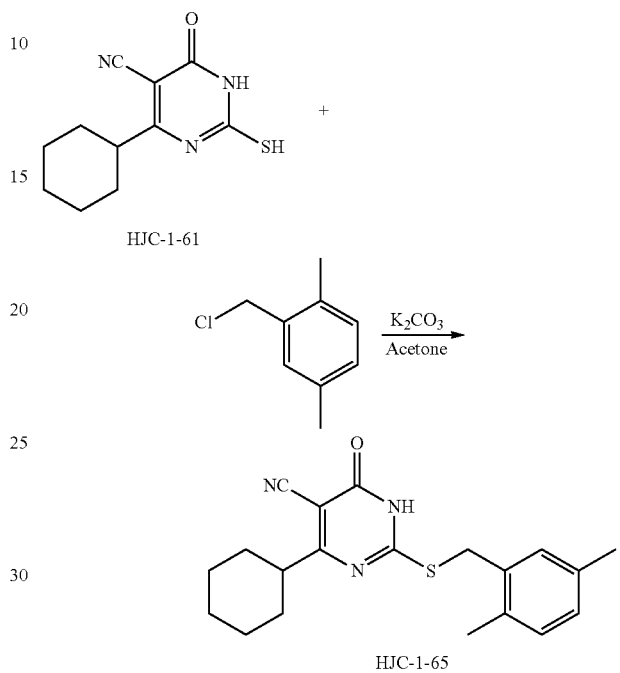

HJC-1-65

To a solution of HJC-1-61 (100 mg, 0.425 mmol) and $K_2CO_3$ (88 mg, 0.637 mmol) in acetone (10 mL) was added 2-chloromethyl-1,4-dimethylbenzene (66 mg, 0.425 mmol) at 0° C. The mixture was stirred at r.t. for 48 h. The solution was diluted with EtOAc (100 mL), washed with 1 N HCl (aq.) (10 mL) and brine (10 mL). The organic layer was dried over anhydrous $Na_2SO_4$, and concentrated under reduced pressure, and the residue was washed with EtOAc (3 mL) to obtain the desired product as a white solid (120 mg, 80%). $^1$H NMR (600 MHz, CDCl$_3$) δ 7.19 (s, 1H), 7.08 (d, 1H, J=7.2 Hz), 7.03 (d, 1H, J=8.4 Hz), 4.49 (s, 2H), 3.02-2.98 (m, 1H), 2.34 (s, 3H), 2.30 (s, 3H), 1.88-1.77 (m, 5H), 1.71-1.63 (m, 2H), 1.45-1.39 (m, 2H), 1.31-1.26 (m, 1H).

Example 8

4-Cyclohexyl-2-(4-Methyl-Benzylsulfanyl)-6-Oxo-1,6-Dihydro-Pyrimidine-5-Carbonitrile (HJC-1-67)

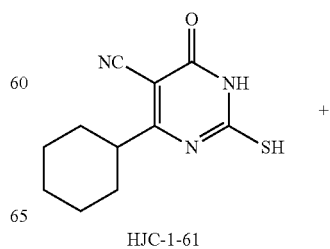

HJC-1-61

-continued

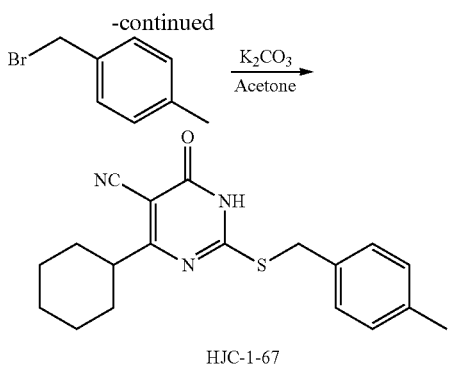

HJC-1-67

To a solution of HJC-1-61 (150 mg, 0.64 mmol) and K$_2$CO$_3$ (132 mg, 0.96 mmol) in acetone (10 mL) was added 1-bromomethyl-4-methylbenzene (124 mg, 0.67 mmol) at 0° C. The mixture was stirred at 0° C. for 1 h. The solution was diluted with EtOAc (100 mL), washed with 1 N HCl (aq.) (10 mL) and brine (10 mL). The organic layer was dried over anhydrous Na$_2$SO$_4$, and then concentrated under reduced pressure. The residue was purified by silica gel column chromatography (hexane/EtOAc=1/1 to 1/3) to give the desired product as a white solid (200 mg, 93%). $^1$H NMR (600 MHz, CDCl$_3$/CD$_3$OD 2:1) δ 7.19 (d, 2H, J=7.8 Hz), 6.99 (d, 2H, J=7.8 Hz), 4.24 (s, 2H), 2.69-2.65 (m, 1H), 2.22 (s, 3H), 1.74-1.72 (m, 2H), 1.67-1.63 (m, 3H), 1.59-1.53 (m, 2H), 1.30-1.24 (m, 2H), 1.20-1.16 (m, 1H). $^{13}$C NMR (150 MHz, CDCl$_3$/CD$_3$OD 2:1) δ 177.5, 173.4, 173.1, 136.6, 135.2, 129.0 (2C), 128.8 (2C), 119.4, 90.0, 44.9, 34.8, 30.9 (2C), 26.0 (2C), 25.8, 20.9.

Example 9

4-Cyclohexyl-2-(3,5-Dimethyl-Benzylsulfanyl)-6-Oxo-1,6-Dihydro-Pyrimidine-5-Carbonitrile (HJC-1-72)

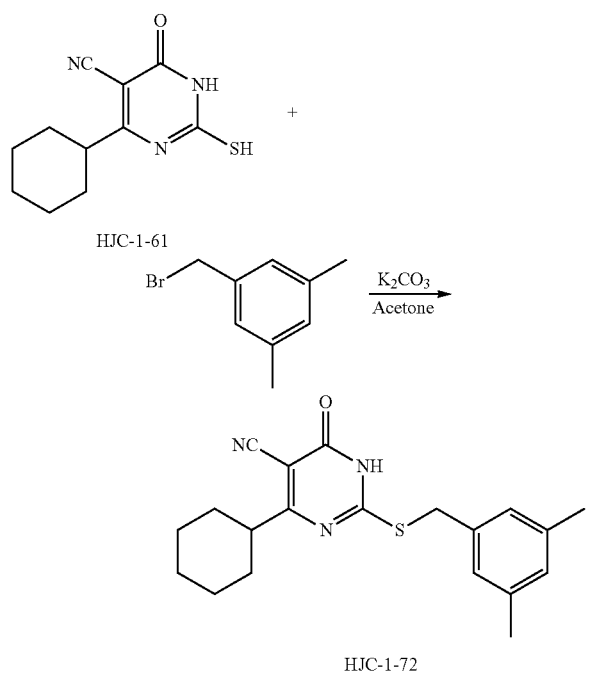

HJC-1-72

To a solution of HJC-1-61 (100 mg, 0.43 mmol) and K$_2$CO$_3$ (88 mg, 0.64 mmol) in acetone (10 mL) was added 1-bromomethyl-3,5-dimethylbenzene (85 mg, 0.43 mmol) at 0° C. The mixture was stirred at 0° C. for 1 h. The solution was diluted with EtOAc (100 mL), washed with 1 N HCl (aq.) (10 mL) and brine (10 mL). The organic layer was dried over anhydrous Na$_2$SO$_4$, and then concentrated under reduced pressure. The residue was purified by silica gel column chromatography (hexane/EtOAc=1/1 to 1/3) to give the desired product as a white solid (130 mg, 87%). $^1$H NMR (600 MHz, CDCl$_3$) δ 7.02 (s, 2H), 6.92 (s, 1H), 4.40 (s, 2H), 3.01-2.97 (m, 1H), 2.30 (s, 6H), 1.88-1.86 (m, 2H), 1.81-1.79 (m, 3H), 1.70-1.64 (m, 2H), 1.46-1.39 (m, 2H), 1.32-1.26 (m, 1H). $^{13}$C NMR (150 MHz, CDCl$_3$) δ 179.9, 165.8, 162.9, 138.5 (2C), 135.4, 129.7, 127.0 (2C), 114.0, 94.8, 45.4, 35.4, 30.8 (2C), 25.8, 25.7 (2C), 21.3 (2C).

Example 10

4-Cyclohexyl-2-(2,4-Dimethyl-Benzylsulfanyl)-6-Oxo-1,6-Dihydro-Pyrimidine-5-Carbonitrile (HJC-1-74)

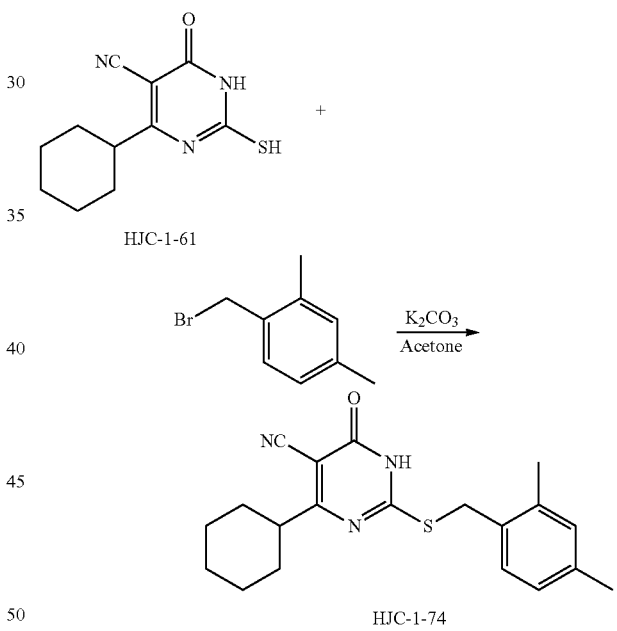

HJC-1-74

To a solution of HJC-1-61 (100 mg, 0.43 mmol) and K$_2$CO$_3$ (88 mg, 0.64 mmol) in acetone (10 mL) was added 1-bromomethyl-2,4-dimethylbenzene (85 mg, 0.43 mmol) at 0° C. The mixture was stirred at 0° C. for 1 h. The solution was diluted with EtOAc (100 mL), washed with 1 N HCl (aq.) (10 mL) and brine (10 mL). The organic layer was dried over anhydrous Na$_2$SO$_4$, and then concentrated under reduced pressure. The residue was purified by silica gel column chromatography (hexane/EtOAc=1/1 to 1/3) to give the desired product as a white solid (136 mg, 91%). $^1$H NMR (600 MHz, CDCl$_3$/CD$_3$OD 1:2) δ 7.21 (d, 1H, J=7.2 Hz), 6.99 (s, 1H), 6.93 (d, 1H, J=7.2 Hz), 4.46 (s, 2H), 2.92-2.88 (m, 1H), 2.33 (s, 3H), 2.27 (s, 3H), 1.86-1.84 (m, 2H), 1.80-1.74 (m, 3H), 1.70-1.63 (m, 2H), 1.42-1.36 (m, 2H), 1.29-1.23 (m, 1H). $^{13}$C NMR (150 MHz, CDCl$_3$/CD$_3$OD 1:2) δ 179.5, 167.3, 162.7, 138.6, 138.2, 137.3, 131.9, 130.5, 127.4, 115.2, 94.6, 45.8, 33.8, 31.2, 31.1, 26.2, 26.1, 21.2, 21.1, 19.5.

Example 11

2-Benzylsulfanyl-4-Cyclohexyl-6-Oxo-1,6-Dihydro-Pyrimidine-5-Carbonitrile (HJC-1-76)

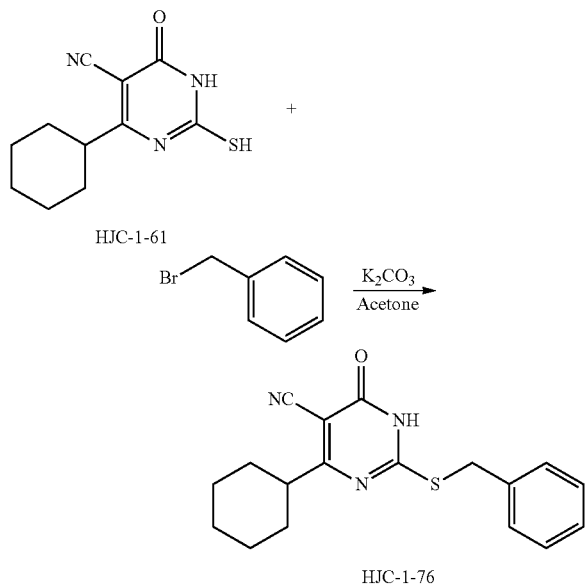

To a solution of HJC-1-61 (100 mg, 0.43 mmol) and K$_2$CO$_3$ (88 mg, 0.64 mmol) in acetone (10 mL) was added bromomethylbenzene (73 mg, 0.43 mmol) at 0° C. The mixture was stirred at 0° C. for 1 h. The solution was diluted with EtOAc (100 mL), washed with 1 N HCl (aq.) (10 mL) and brine (10 mL). The organic layer was dried over anhydrous Na$_2$SO$_4$, and then concentrated under reduced pressure. The residue was purified by silica gel column chromatography (hexane/EtOAc=1/1 to 1/3) to give the desired product as a white solid (130 mg, 94%). $^1$H NMR (600 MHz, CDCl$_3$) δ 7.33-7.32 (m, 3H), 7.25-7.22 (m, 2H), 4.39 (s, 2H), 2.88-2.86 (m, 1H), 1.80-1.78 (m, 2H), 1.76-1.69 (m, 3H), 1.60-1.56 (m, 2H), 1.36-1.33 (m, 2H), 1.22-1.20 (m, 1H). $^{13}$C NMR (150 MHz, CDCl$_3$) δ 179.2, 167.5, 165.2, 136.3, 129.3, 129.2, 129.1, 128.8, 127.8, 115.3, 93.9, 45.2, 35.3, 30.8 (2C), 25.8 (2C), 25.8.

Example 12

4-Cyclohexyl-6-Oxo-2-(2,4,6-Trimethyl-Benzyl Sulfanyl)-1,6-Dihydro-Pyrimidine-5-Carbonitrile (HJC-1-87)

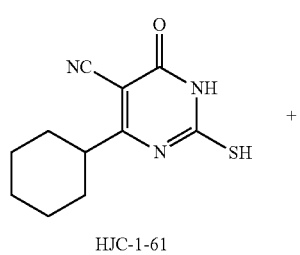

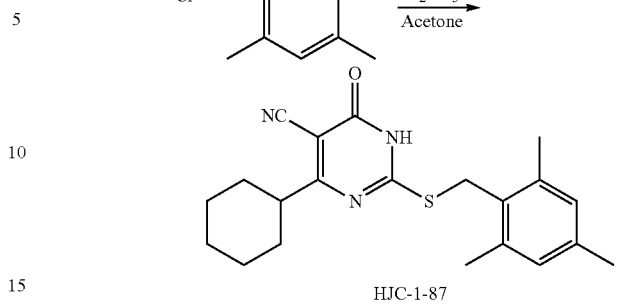

To a solution of HJC-1-61 (100 mg, 0.43 mmol) and K$_2$CO$_3$ (88 mg, 0.64 mmol) in acetone (10 mL) was added 2-chloromethyl-1,3,5-trimethylbenzene (72 mg, 0.43 mmol) at 0° C. The mixture was stirred at r.t. for 36 h. The solution was diluted with EtOAc (100 mL), washed with 1 N HCl (aq.) (10 mL) and brine (10 mL). The organic layer was dried over anhydrous Na$_2$SO$_4$, and then concentrated under reduced pressure. The residue was purified by silica gel column chromatography (hexane/EtOAc=1/1 to 1/3) to give the desired product as a white solid (150 mg, 95%). $^1$H NMR (600 MHz, CDCl$_3$) δ 6.84 (s, 2H), 4.50 (s, 2H), 2.93-2.90 (m, 1H), 2.32 (s, 6H), 2.26 (s, 3H), 1.84-1.73 (m, 5H), 1.66-1.61 (m, 2H), 1.42-1.35 (m, 2H), 1.27-1.21 (m, 1H). $^{13}$C NMR (150 MHz, CDCl$_3$/CD$_3$OD 1:1) δ 178.9, 167.1, 162.4, 137.7, 137.5 (2C), 129.2 (2C), 127.1, 114.6, 94.0, 45.1, 30.6, 30.6 (2C), 25.6 (2C), 25.5, 20.7, 19.4 (2C).

Example 13

2-(2,5-Dimethyl-Benzylsulfanyl)-4-(1-Methyl-Piperidin-4-Yl)-6-Oxo-1,6-Dihydro-Pyrimidine-5-Carbonitrile (HJC-1-88)

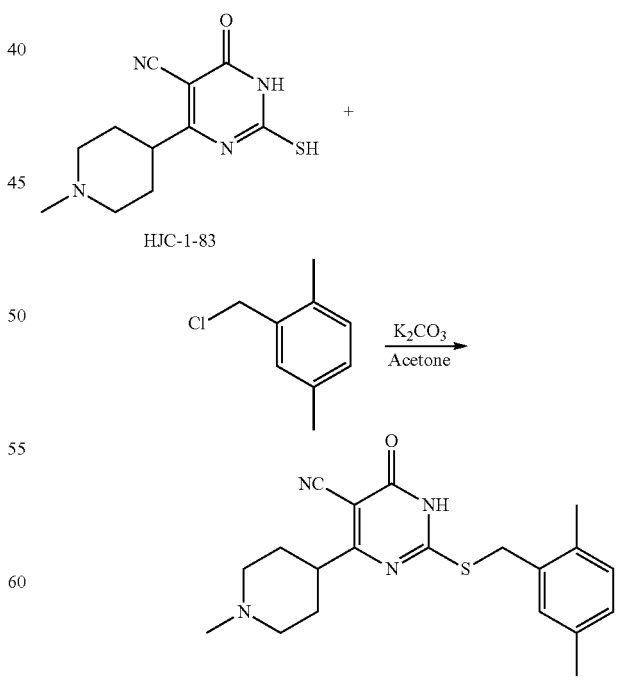

To a solution of HJC-1-83 (125 mg, 0.50 mmol) and K$_2$CO$_3$ (104 mg, 0.75 mmol) in acetone (10 mL) was added 2-chloromethyl-1,4-dimethylbenzene (77 mg, 0.50 mmol) at 0° C. The mixture was stirred at r.t. for 24 h. The solution was concentrated and the residue was purified by silica gel column chromatography (EtOAc/MeOH/Et₃N=8/1/1) to give the desired product as a white solid (120 mg, 65%). $^1$H NMR (600 MHz, CDCl$_3$/CD$_3$OD 1:1) δ 6.70 (s, 1H), 6.62 (d, 1H, J=7.8 Hz), 6.55 (d, 1H, J=7.8 Hz), 3.92 (s, 2H), 3.15-3.11 (m, 2H), 2.63-2.59 (m, 1H), 2.56-2.53 (m, 2H), 2.39 (s, 3H), 1.91 (s, 3H), 1.86 (s, 3H), 1.85-1.81 (m, 2H), 1.50-1.48 (m, 2H). $^{13}$C NMR (150 MHz, CDCl$_3$/CD$_3$OD 1:1) δ 174.5, 173.3, 172.4, 135.4, 134.8, 133.6, 130.5, 130.2, 128.1, 117.8, 90.4, 54.4 (2C), 44.5, 33.3 (2C), 28.4 (2C), 20.7, 18.6.

Example 14

2-(2,5-Dimethyl-Benzylsulfanyl)-4-Isopropyl-6-Oxo-1,6-Dihydro-Pyrimidine-5-Carbonitrile (HJC-1-95)

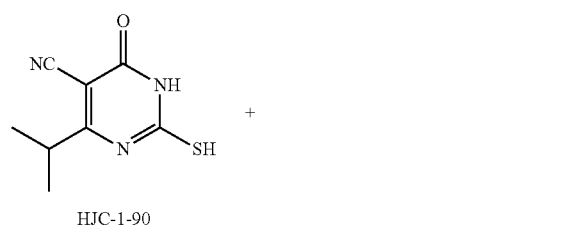

HJC-1-90

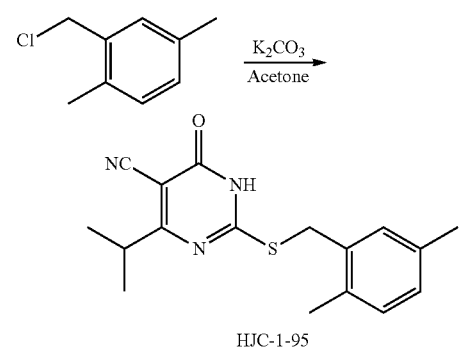

HJC-1-95

To a solution of HJC-1-90 (100 mg, 0.51 mmol) and K$_2$CO$_3$ (106 mg, 0.77 mmol) in acetone (10 mL) was added 2-chloromethyl-1,4-dimethylbenzene (79 mg, 0.51 mmol) at 0° C. The mixture was stirred at 65° C. for 2 h. The solution was diluted with EtOAc (100 mL), washed with 1 N (aq.) HCl (10 mL) and brine (10 mL). The organic layer was dried over anhydrous Na$_2$SO$_4$, and then concentrated under reduced pressure. The residue was purified by silica gel column chromatography (hexane:EtOAc=1/1 to 1/3) to give the desired product as a pale yellow solid (120 mg, 75%). $^1$H NMR (600 MHz, CDCl$_3$/CD$_3$OD 3:1) δ 7.12 (s, 1H), 7.01 (d, 1H, J=7.2 Hz), 6.96 (d, 1H, J=7.2 Hz), 4.43 (d, 2H), 3.28-3.24 (m, 1H), 2.28 (s, 3H), 2.23 (s, 3H), 1.26 (d, 6H, J=6.6 Hz). $^{13}$C NMR (150 MHz, CDCl$_3$/CD$_3$OD 3:1) δ 180.0, 166.0, 161.2, 135.8, 133.7, 132.6, 130.7, 130.6, 129.1, 114.1, 94.6, 35.1, 33.5, 20.7, 20.6 (2C), 18.7.

Example 15

4-Cyclopentyl-2-(2,5-Dimethyl-Benzylsulfanyl)-6-Oxo-1,6-Dihydro-Pyrimidine-5-Carbonitrile (HJC-1-97)

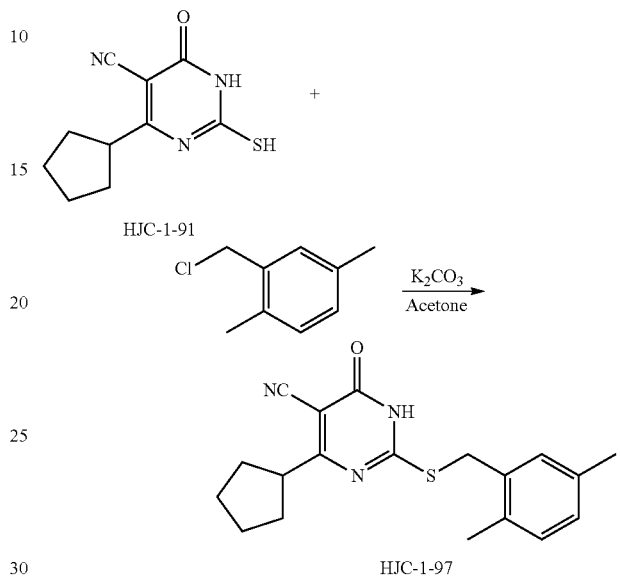

To a solution of HJC-1-91 (120 mg, 0.54 mmol) and K$_2$CO$_3$ (112 mg, 0.81 mmol) in acetone (10 mL) was added 2-chloromethyl-1,4-dimethylbenzene (84 mg, 0.54 mmol) at 0° C. The mixture was stirred at 65° C. for 1 h. The solution was diluted with EtOAc (100 mL), washed with 1 N (aq.) HCl (10 mL) and brine (10 mL). The organic layer was dried over Na$_2$SO$_4$, and then concentrated under reduced pressure. The residue was purified by silica gel column chromatography (hexane/EtOAc=1/1 to 1/3) to give the desired product as a white solid (170 mg, 92%). $^1$H NMR (600 MHz, CDCl$_3$) δ 13.00 (bs, 1H), 7.15 (s, 1H), 7.08 (d, 1H, J=7.8 Hz), 7.30 (d, 1H, J=7.2 Hz), 4.47 (s, 2H), 3.48-3.44 (m, 1H), 2.34 (s, 3H), 2.25 (s, 3H), 2.08-2.05 (m, 2H), 1.92-1.87 (m, 4H), 1.76-1.74 (m, 2H). $^{13}$C NMR (150 MHz, CDCl$_3$) δ 180.0, 165.9, 162.6, 136.0, 133.9, 132.4, 130.8, 130.8, 129.3, 114.2, 95.4, 46.0, 33.8, 32.7 (2C), 26.8 (2C), 20.9, 19.0.

Example 16

4-Cyclopropyl-2-(2,5-Dimethylbenzylsulfanyl)-6-Oxo-1,6-Dihydro-Pyrimidine-5-Carbonitrile (HJC-1-98)

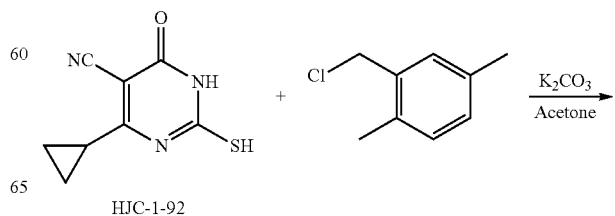

HJC-1-92

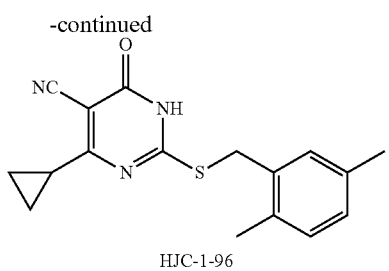

HJC-1-96

To a solution of HJC-1-92 (70 mg, 0.36 mmol) and K$_2$CO$_3$ (75 mg, 0.54 mmol) in acetone (10 mL) was added 2-chloromethyl-1,4-dimethylbenzene (56 mg, 0.36 mmol) at 0° C. The mixture was stirred at r.t. for 16 h. The solution was diluted with EtOAc (100 mL), washed with 1 N HCl (aq.) (10 mL) and brine (10 mL). The organic layer was dried over anhydrous Na$_2$SO$_4$, and then concentrated under reduced pressure. The residue was purified by silica gel column chromatography (hexane/EtOAc=1/1 to 1/3) to give the desired product as a pale yellow solid (90 mg, 80%). $^1$H NMR (600 MHz, CDCl$_3$/CD$_3$OD 1:2) δ 6.89 (s, 1H), 6.86 (d, 1H, J=7.8 Hz), 6.80 (d, 1H, J=7.8 Hz), 4.15 (s, 2H), 2.12-2.08 (m, 1H), 2.11 (s, 3H), 2.10 (s, 3H), 1.14-1.12 (m, 2H), 1.05-1.02 (m, 2H). $^{13}$C NMR (150 MHz, CDCl$_3$/CD$_3$OD 1:3) δ 176.4, 165.6, 160.3, 135.6, 133.5, 132.0, 130.3, 130.3, 128.8, 114.7, 94.1, 33.3, 20.3, 18.3, 16.6, 11.4 (2C).

Example 17

4-Cyclohexyl-6-Oxo-2-Phenylamino-1,6-Dihydro-Pyrimidine-5-Carbonitrile (HJC-1-99)

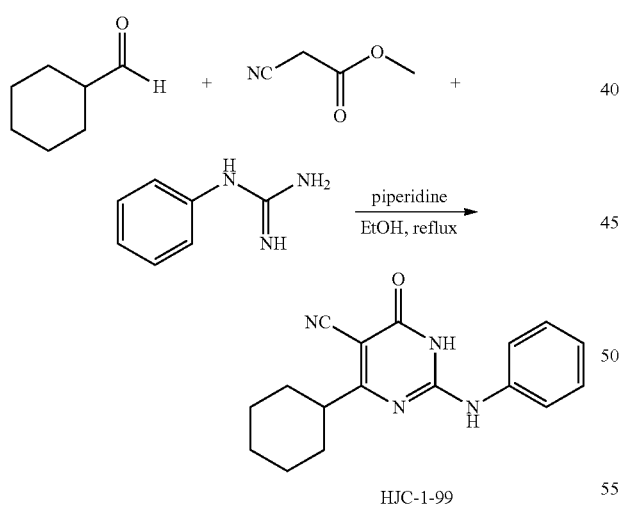

HJC-1-99

To a solution of cyclohexanecarbaldehyde (99 mg, 1.0 mmol), methyl cyanoacetate (112 mg, 10 mmol), and N-phenylguanidine (197 mg, 1.0 mmol) in absolute ethanol (10 mL) was added piperidine (213 mg, 2.5 mmol). The mixture was heated under reflux for 1.5 h and then cooled to room temperature. The solution was concentrated and then the residue was extracted with ethyl acetate (100 mL) and 2N HCl (aq.) (20 mL). The organic layer was isolated, washed with brine, and dried over anhydrous Na$_2$SO$_4$. The solvent was evaporated under reduced pressure. The residue was purified by silica gel column chromatography (DCM/MeOH=10/1) to give the desired product as a white solid (140 mg, 48%). $^1$H NMR (600 MHz, CDCl$_3$/CD$_3$OD 1:2) δ 7.56 (d, 2H, J=7.2 Hz), 7.37 (t, 2H, J=7.8 Hz), 7.17 (t, 1H, J=7.2 Hz), 2.87 (t, 1H, J=10.8 Hz), 1.86-1.80 (m, 4H), 1.75-1.73 (m, 1H), 1.64-1.56 (m, 2H), 1.42-1.36 (m, 2H), 1.29-1.25 (m, 1H).

Example 18

4-[5-Cyano-2-(2,5-Dimethylbenzylsulfanyl)-6-Oxo-1,6-Dihydro-Pyrimidin-4-Yl]-Piperidine-1-Carboxylic Acid Tert-Butyl Ester (HJC-1-93)

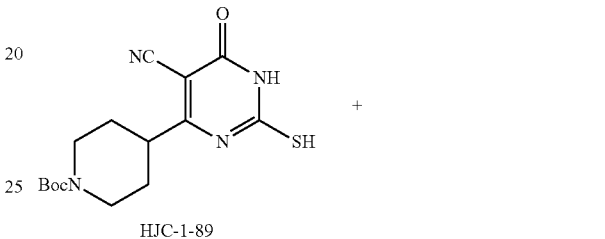

HJC-1-89

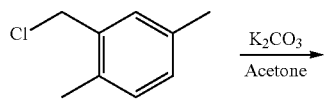

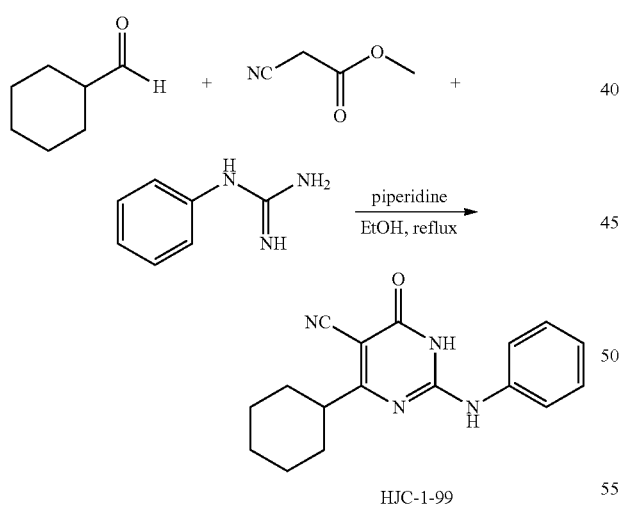

HJC-1-93

To a solution of HJC-1-89 (150 mg, 0.45 mmol) and K$_2$CO$_3$ (92 mg, 0.67 mmol) in acetone (10 mL) was added 2-chloromethyl-1,4-dimethylbenzene (70 mg, 0.45 mmol) at 0° C. The mixture was stirred at 75° C. for 18 h. The solution was diluted with EtOAc (100 mL), washed with 1 N HCl (aq.) (10 mL) and brine (10 mL). The organic layer was dried over anhydrous Na$_2$SO$_4$, and then concentrated under reduced pressure. The residue was purified by silica gel column chromatography (hexane/EtOAc=1/1 to 1/3) to give the desired product as a pale yellow solid (156 mg, 77%). $^1$H NMR (600 MHz, CDCl$_3$) δ 6.97 (s, 1H), 6.88 (d, 1H, J=8.4 Hz), 6.83 (d, 1H, J=7.2 Hz), 4.26 (s, 2H), 4.16-4.14 (m, 2H), 4.06-4.05 (m, 2H), 2.93-2.90 (m, 1H), 2.69-2.64 (m, 2H), 2.14 (s, 3H), 2.09 (s, 3H), 1.71-1.66 (m, 2H), 1.61-1.59 (m, 2H), 1.28 (s, 9H).

Example 19

2-(2,5-Dimethylbenzylsulfanyl)-6-Oxo-4-Piperidin-4-Yl-1,6-Dihydro-Pyrimidine-5-Carbonitrile (HJC-2-1)

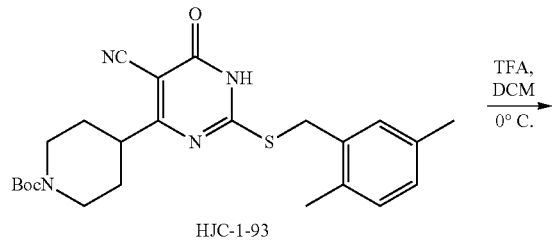

To a solution of HJC-1-93 (70 mg, 0.15 mmol) in DCM (4 mL) was added TFA (1 mL) at 0° C. The mixture was stirred at 0° C. for 2 h. The reaction mixture was concentrated, and the residue was partitioned between EtOAc (10 mL) and 1 N NaHCO₃ (aq.) (10 mL). The pale yellow solid (50 mg, 92%) precipitated and was obtained by the filtration. ¹H NMR (600 MHz, DMSO-d6) δ 8.56 (s, 1H), 8.24 (s, 1H), 7.16 (s, 1H), 7.05 (d, 1H, J=7.2 Hz), 6.96 (d, 1H, J=6.6 Hz), 4.24 (s, 2H), 3.04-3.03 (m, 2H), 2.97-2.95 (m, 2H), 2.27-2.19 (m, 1H), 2.22 (s, 3H), 2.19 (s, 3H), 1.99-1.93 (m, 2H), 1.83-1.81 (m, 2H). ¹³C NMR (150 MHz, DMSO-d6) δ 173.3, 171.7, 170.0, 135.9, 134.7, 133.2, 130.4, 130.0, 127.7, 119.1, 89.3, 43.6 (2C), 32.3 (2C), 27.7 (2C), 20.5, 18.5.

Example 20

2-(4-Chloro-Phenylamino)-4-Cyclohexyl-6-Oxo-1,6-Dihydro-Pyrimidine-5-Carbonitrile (HJC-2-2)

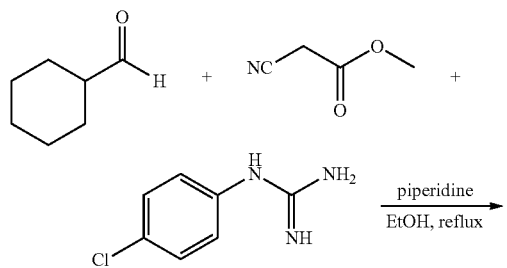

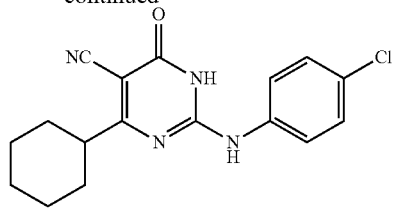

To a solution of cyclohexanecarbaldehyde (99 mg, 1.0 mmol), methyl cyanoacetate (112 mg, 10 mmol), and N-(4-chloro-phenyl)guanidine (232 mg, 1.0 mmol) in absolute ethanol (10 mL) was added piperidine (213 mg, 2.5 mmol). The mixture was heated under reflux for 3 h and then cooled to room temperature. The solution was concentrated and then the residue was extracted with ethyl acetate (75 mL) and 2N HCl (aq.) (20 mL). The organic layer was isolated, washed with brine, and dried over anhydrous Na₂SO₄. The solvent was evaporated under reduced pressure. The residue was purified by silica gel column chromatography (DCM/MeOH=10/1) to give the desired product as a white solid (160 mg, 49%). ¹H NMR (600 MHz, DMSO-d6) δ 11.60 (bs, 1H), 9.61 (s, 1H), 7.62 (d, 2H, J=6.6 Hz), 7.42 (d, 2H, J=7.8 Hz), 2.75-2.72 (m, 1H), 1.79-1.77 (m, 2H), 1.74-1.72 (m, 2H), 1.69-1.67 (m, 1H), 1.53-1.47 (m, 2H), 1.34-1.28 (m, 2H), 1.22-1.16 (m, 1H).

Example 21

(5-Cyano-4-Cyclohexyl-6-Oxo-1,6-Dihydro-Pyrimidin-2-Ylsulfanyl)-Acetic Acid (HJC-2-4)

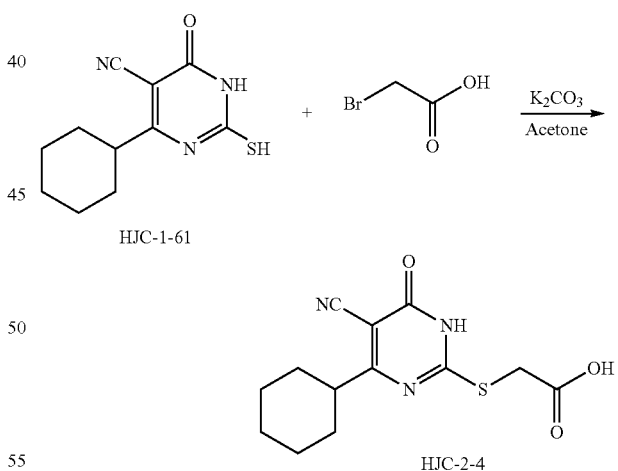

To a solution of HJC-1-61 (235 mg, 1.0 mmol) and K₂CO₃ (207 mg, 1.5 mmol) in acetone (10 mL) was added bromo-acetic acid (139 mg, 1.0 mmol) at 0° C. The mixture was stirred at 0° C. for 3 h. The solution was diluted with EtOAc (100 mL), washed with 1 N HCl (aq.) (10 mL) and brine (10 mL). The organic layer was dried over anhydrous Na₂SO₄, and concentrated under reduced pressure, and the residue was washed with EtOAc (10 mL) and hexane (10 mL) to obtain the desired product as a pale yellow solid (250 mg, 85%). ¹H NMR (600 MHz, CDCl₃/CD₃OD 1:2) δ 3.93

(s, 2H), 2.86 (t, 1H, J=10.8 Hz), 1.82-1.80 (m, 2H), 1.72-1.70 (m, 3H), 1.64-1.58 (m, 2H), 1.39-1.32 (m, 2H), 1.28-1.24 (m, 1H).

Example 22

2-(5-Cyano-4-Cyclohexyl-6-Oxo-1,6-Dihydro-Pyrimidin-2-Ylsulfanyl)-N-Phenyl-Acetamide (HJC-2-6)

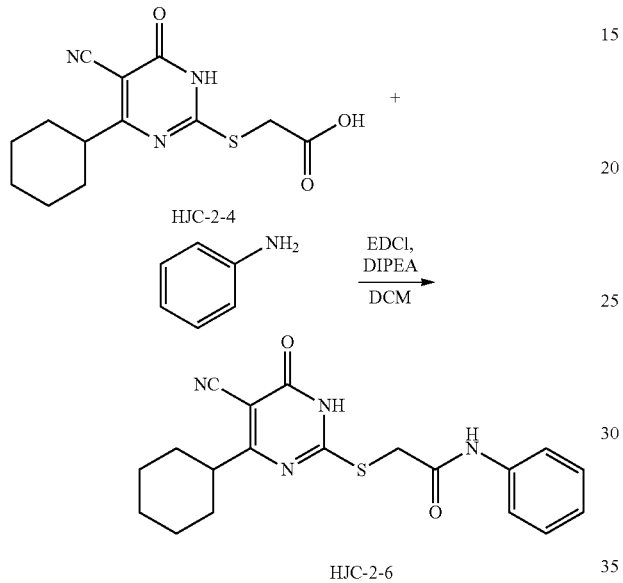

To a solution of HJC-2-4 (80 mg, 0.27 mmol) and phenylamine (31 mg, 0.33 mmol) in 10 mL of DCM was added DIPEA (105 mg, 0.81 mmol). EDCI (51 mg, 0.33 mmol) was added at 0° C. The resulting mixture was stirred at r.t. for 2 h. The solution was diluted with DCM (50 mL), washed with 1 N HCl (aq.) (10 mL) and brine (10 mL). The organic layer was dried over anhydrous $Na_2SO_4$, and then concentrated under reduced pressure. The residue was purified by silica gel column chromatography (EtOAc) to give the desired product as a white solid (90 mg, 91%). $^1H$ NMR (600 MHz, $CDCl_3/CD_3OD$ 1:3) δ 7.56 (d, 2H, J=7.8 Hz), 7.28 (t, 2H, J=7.2 Hz), 7.07 (t, 2H, J=7.2 Hz), 4.04 (s, 2H), 2.79 (t, 1H, J=11.4 Hz), 1.64-1.58 (m, 4H), 1.55-1.53 (m, 3H), 1.27-1.21 (m, 2H), 0.93-0.87 (m, 1H).

Example 23

1,3,5-Trimethyl-2-(4-Pentyl-Benzenesulfonyl)-Benzene (HJC-2-62)

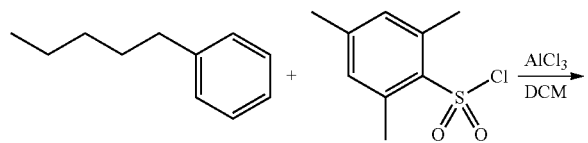

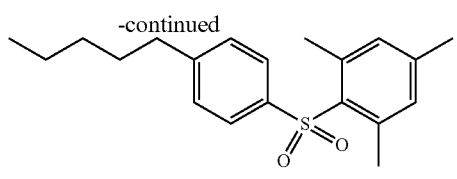

A mixture of mesitylsulfonyl chloride (147 mg, 0.68 mmol), pentyl-benzene (100 mg, 0.68 mmol) and $AlCl_3$ (181 mg, 1.36 mmol) in DCM (3 mL) was stirred for 2 hours at room temperature. The mixture was then poured into 10 mL of 5% HCl (aq.), and extracted by DCM (30 mL). The organic phase was washed by aqueous $KHCO_3$, brine, and dried over anhydrous $Na_2SO_4$. The resulting solution was evaporated, and the residue was purified by silica gel column chromatography (Hexane/EtOAc=10/1) to give the desired product as a pale yellow oil (200 mg, 90%). $^1H$ NMR (600 MHz, $CDCl_3$) δ 7.68 (d, 2H, J=7.2 Hz), 7.25 (d, 2H, J=6.6 Hz), 6.93 (s, 2H), 2.63 (t, 2H, J=7.2 Hz), 2.49 (s, 6H), 2.28 (s, 3H), 1.57-1.62 (m, 2H), 1.28-1.32 (m, 4H), 0.88 (t, 2H, J=6.6 Hz). $^{13}C$ NMR (150 MHz, $CDCl_3$) δ 148.4, 143.3, 140.9, 140.1, 134.3, 132.3, 128.9, 126.4, 35.9, 31.5, 30.8, 22.9, 22.6, 21.1, 14.1.

Example 24

1,3,5-Trimethyl-2-(2,4,5-Trimethyl-Benzenesulfonyl)-Benzene (HJC-2-71)

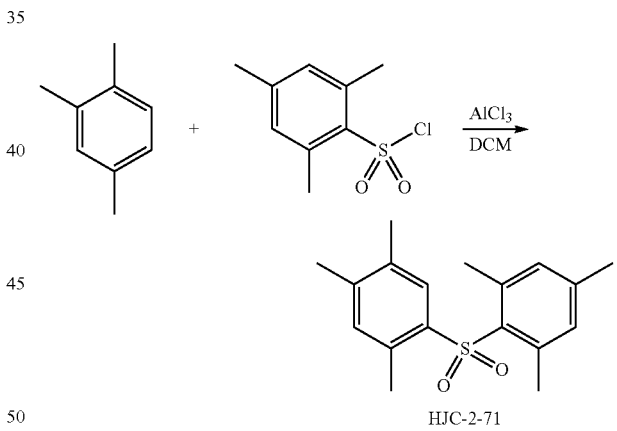

A mixture of mesitylsulfonyl chloride (219 mg, 1.0 mmol), 1,2,4-trimethyl-benzene (125 mg, 1.05 mmol) and $AlCl_3$ (266 mg, 2.0 mmol) in DCM (5 mL) was stirred for 2 hours at room temperature. The mixture was then poured into 10 mL of 5% HCl (aq.), and extracted by DCM (30 mL). The organic phase was washed by aqueous $KHCO_3$, brine, and dried over anhydrous $Na_2SO_4$. The resulting solution was evaporated, and the residue was purified by silica gel column chromatography (Hexane/EtOAc=10/1) to give the desired product as a white solid (290 mg, 96%). $^1H$ NMR (600 MHz, $CDCl_3$) δ 7.81 (s, 1H), 6.95 (s, 1H), 6.90 (s, 2H), 2.48 (s, 6H), 2.28 (s, 6H), 2.25 (s, 3H), 2.17 (s, 3H). $^{13}C$ NMR (150 MHz, $CDCl_3$) δ 142.9, 142.1, 139.5, 139.0, 134.9, 134.3, 134.1, 133.8, 132.1, 129.1, 22.6, 21.1, 19.7, 19.4, 18.6.

Example 25

2-(4-Methoxy-Benzenesulfonyl)-1,3,5-Trimethyl-Benzene (HJC-2-82)

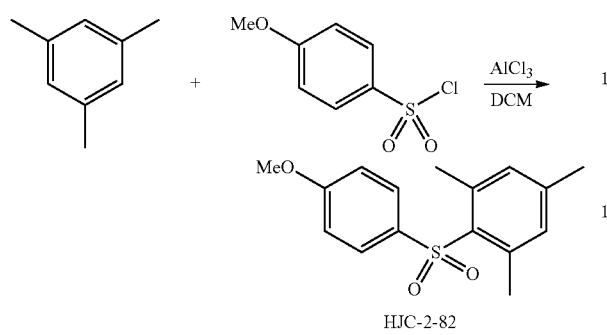

A mixture of 4-methoxy-benzenesulfonyl chloride (206 mg, 1.0 mmol), mesitylene (120 mg, 1.0 mmol) and AlCl$_3$ (200 mg, 1.5 mmol) in DCM (5 mL) was stirred for 2 hours at room temperature. The mixture was then poured into 10 mL of 5% HCl (aq.), and extracted by DCM (30 mL). The organic phase was washed by aqueous KHCO$_3$, brine, and dried over anhydrous Na$_2$SO$_4$. The resulting solution was evaporated, and the residue was purified by silica gel column chromatography (Hexane/EtOAc=10/1) to give the desired product as a white solid (250 mg, 86%). $^1$H NMR (600 MHz, CDCl$_3$) δ 7.74 (s, 2H), 6.94 (s, 4H), 3.85 (s, 3H), 2.61 (s, 6H), 2.29 (s, 3H). $^{13}$C NMR (150 MHz, CDCl$_3$) δ 162.9, 143.1, 139.9, 135.4, 134.7, 132.3, 128.6, 114.1, 55.7, 23.0, 21.1.

Example 26

1,3,5-Trimethyl-2-(Toluene-4-Sulfonyl)-Benzene (HJC-2-85)

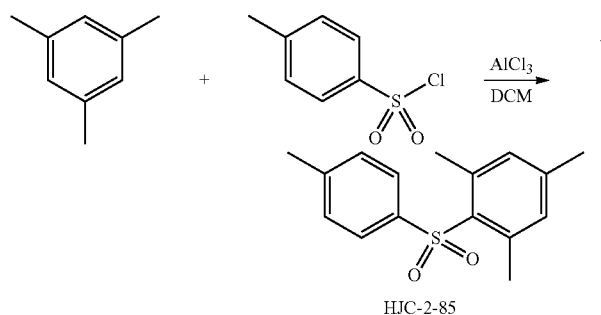

A mixture of 4-methyl-benzenesulfonyl chloride (191 mg, 1.0 mmol), mesitylene (120 mg, 1.0 mmol) and AlCl$_3$ (200 mg, 1.5 mmol) in DCM (10 mL) was stirred for 2 hours at room temperature. The mixture was then poured into 10 mL of 5% HCl (aq.), and extracted by DCM (30 mL). The organic phase was washed by aqueous KHCO$_3$, brine, and dried over anhydrous Na$_2$SO$_4$. The resulting solution was evaporated, and the residue was purified by silica gel column chromatography (Hexane/EtOAc=10/1) to give the desired product as a white solid (220 mg, 80%). $^1$H NMR (600 MHz, CDCl$_3$) δ 7.68 (d, 2H, J=7.8 Hz), 7.27 (d, 2H, J=7.2 Hz), 6.94 (s, 2H), 2.60 (s, 6H), 2.41 (s, 3H), 2.30 (s, 3H).

Example 27

4-(2,4,6-Trimethyl-Benzenesulfonyl)-Phenol (HJC-2-87)

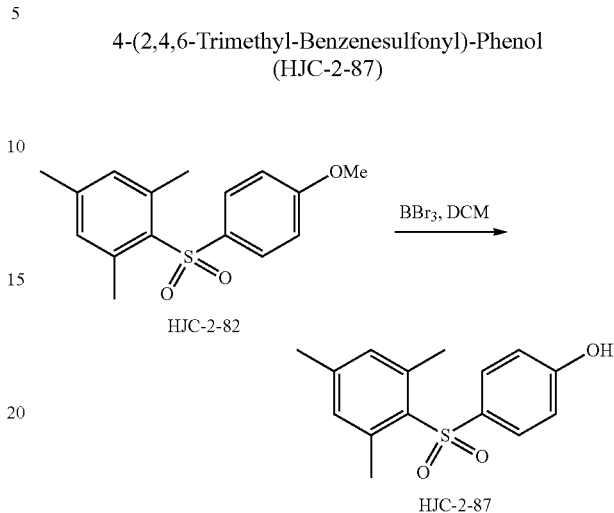

To a solution of HJC-2-82 (350 mg, 1.2 mmol) in 10 mL of DCM was added 1N BBr$_3$/DCM (1.45 mL, 1.45 mmol) at 0° C. The resulting mixture was stirred at r.t. for 16 h. The solution was diluted with EtOAc (50 mL), washed with H$_2$O (10 mL) and brine (10 mL). The organic layer was dried over anhydrous Na$_2$SO$_4$ and then concentrated under reduced pressure. The residue was purified by silica gel column chromatography (Hexane/EtOAc=3/1) to give the desired product as a white solid (306 mg, 92%). $^1$H NMR (600 MHz, CDCl$_3$) δ 7.67 (d, 2H, J=8.4 Hz), 6.93 (s, 2H), 6.86 (d, 2H, J=8.4 Hz), 5.82 (s, 1H), 2.59 (s, 6H), 2.29 (s, 3H).

Example 28

2-(4-Cyclohexyloxy-Benzenesulfonyl)-1,3,5-Trimethyl-Benzene (HJC-2-90)

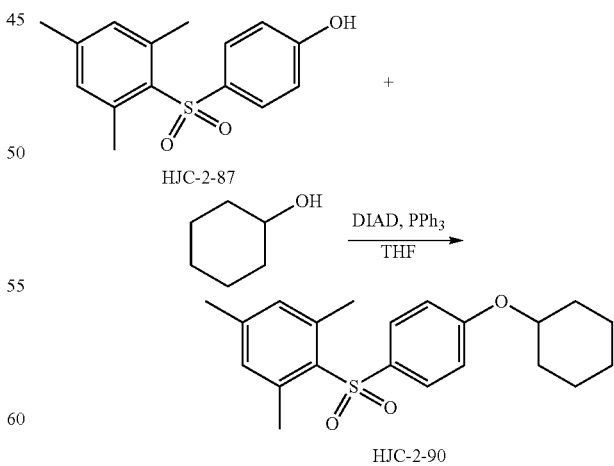

To a solution of HJC-2-87 (50 mg, 0.18 mmol) and PPh$_3$ (58 mg, 0.22 mmol) in THF (5 mL) was added cyclohexanol (36 mg, 0.36 mmol) and DIAD (44 mg, 0.22 mmol). The reaction mixture was stirred at r.t. for 16 h, and then it was partitioned between EtOAc (50 mL) and H$_2$O (20 mL). The organic layer was washed with brine (10 mL), dried with anhydrous Na$_2$SO$_4$, and concentrated to give the crude product. This residue was purified with silica gel column (hexane/EtOAc=7/1) to afford the desired product as a colorless oil (50 mg, 77%). $^1$H NMR (600 MHz, CDCl$_3$) δ 7.69 (d, 2H, J=7.2 Hz), 6.91 (s, 2H), 6.91 (d, 2H, J=6.6 Hz), 4.30 (s, 1H), 2.60 (s, 6H), 2.27 (s, 3H), 1.93-195 (m, 2H), 1.75-1.77 (m, 2H), 1.47-1.57 (m, 3H), 1.29-1.39 (m, 3H). $^{13}$C NMR (150 MHz, CDCl$_3$) δ 161.4, 143.1, 139.9, 134.8, 134.8, 132.3, 128.6, 115.6, 75.8, 31.6, 25.6, 23.7, 23.0, 21.1.

Example 29

4-[4-(2,4,6-Trimethyl-Benzenesulfonyl)-Phenoxy]-Piperidine-1-Carboxylic Acid Tert-Butyl Ester (HJC-2-91)

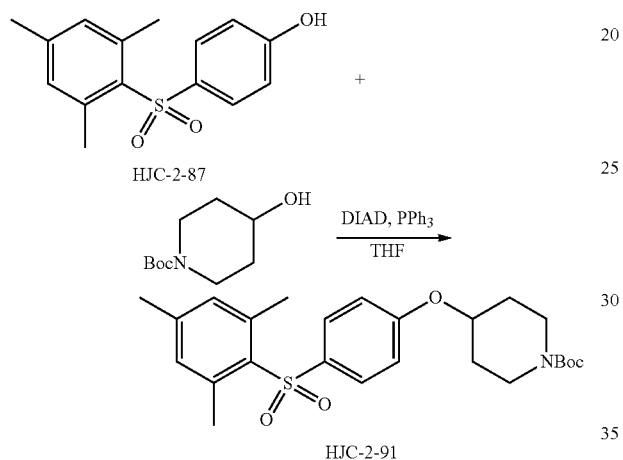

To a solution of HJC-2-87 (138 mg, 0.5 mmol) and PPh$_3$ (262 mg, 1.0 mmol) in THF (5 mL) was added 4-hydroxy-piperidine-1-carboxylic acid tert-butyl ester (201 mg, 1.0 mmol) and DIAD (202 mg, 1.0 mmol). The reaction mixture was stirred at r.t. for 16 h, and then it was partitioned between EtOAc (50 mL) and H$_2$O (20 mL). The organic layer was washed with brine (10 mL), dried with anhydrous Na$_2$SO$_4$, and concentrated to give the crude product. This residue was purified with silica gel column (hexane/EtOAc=2/1) to afford the desired product as a colorless oil (207 mg, 90%). $^1$H NMR (600 MHz, CDCl$_3$) δ 7.71 (d, 2H, J=9.0 Hz), 6.93 (s, 2H), 6.91 (d, 2H, J=8.4 Hz), 4.52-4.54 (m, 1H), 3.65-3.69 (m, 2H), 3.33-3.37 (m, 2H), 2.60 (s, 6H), 2.29 (s, 3H), 1.90-1.93 (m, 2H), 1.73-1.77 (m, 2H), 1.46 (s, 9H).

Example 30

4-[4-(2,4,6-Trimethyl-Benzenesulfonyl)-Phenoxy]-Piperidine (HJC-2-92)

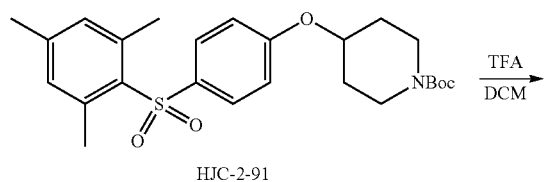

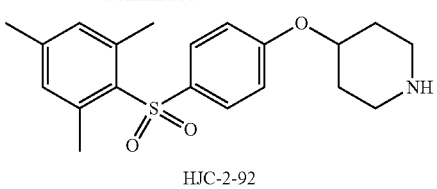

To a solution of HJC-2-91 (128 mg, 0.28 mmol) in DCM (5 mL) was added TFA (1 mL) at 0° C. The mixture was stirred at 0° C. for 1 h. The reaction mixture was concentrated, and the residue was partitioned between EtOAc (50 mL) and 1 N NaHCO$_3$ (10 mL). The organic layer was washed with brine (10 mL), dried with anhydrous Na$_2$SO$_4$, and concentrated to give the crude product. This residue was purified with silica gel column (DCM/MeOH=10/1) to provide HJC-2-92 (100 mg, 99%) as a white solid. $^1$H NMR (600 MHz, CDCl$_3$) δ 8.55 (bs, 1H), 7.70 (d, 2H, J=7.2 Hz), 6.92 (d, 2H, J=9.0 Hz), 6.91 (s, 2H), 4.67 (s, 1H), 3.28 (t, 2H, J=8.4 Hz), 3.12-3.14 (m, 2H), 2.57 (s, 6H), 2.27 (s, 3H), 2.17 (t, 2H, J=7.8 Hz), 2.02-2.04 (m, 2H). $^{13}$C NMR (150 MHz, CDCl$_3$) δ 159.8, 143.4, 139.8, 136.1, 134.2, 132.3, 128.7, 115.6, 68.9, 40.2, 27.2, 22.9, 21.0.

Example 31

2-(4-Iodo-Benzenesulfonyl)-1,3,5-Trimethyl-Benzene (HJC-2-93)

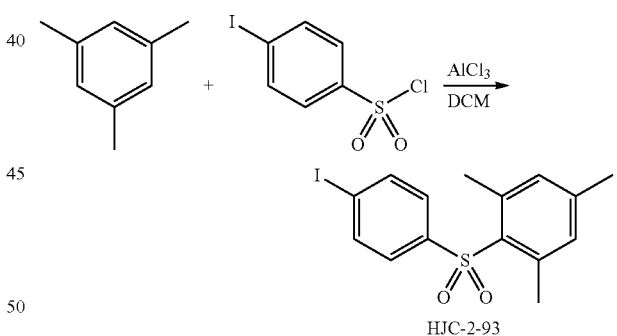

A mixture of 4-Iodo-benzenesulfonyl chloride (302 mg, 1.0 mmol), mesitylene (120 mg, 1.0 mmol) and AlCl$_3$ (150 mg, 1.2 mmol) in DCM (5 mL) was stirred for 2 hours at room temperature. The mixture was then poured into 10 mL of 5% HCl (aq.), and extracted by DCM (30 mL). The organic phase was washed by aqueous KHCO$_3$, brine, and dried over anhydrous Na$_2$SO$_4$. The resulting solution was evaporated, and the residue was purified by silica gel column chromatography (Hexane/EtOAc=10/1) to give the desired product as a white solid (266 mg, 69%). $^1$H NMR (600 MHz, CDCl$_3$) δ 7.82 (d, 2H, J=7.8 Hz), 7.48 (d, 2H, J=7.8 Hz), 6.94 (s, 2H), 2.57 (s, 6H), 2.30 (s, 3H).

Example 32

2-[4-(2,4,6-Trimethyl-Benzenesulfonyl)-Phenoxy]-Ethylamine (HJC-2-96)

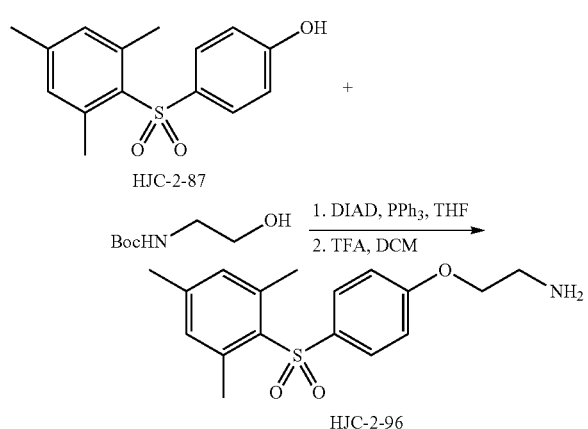

To a solution of HJC-2-87 (100 mg, 0.36 mmol) and PPh₃ (188 mg, 0.72 mmol) in THF (5 mL) was added (2-hydroxyethyl)-carbamic acid tert-butyl ester (117 mg, 0.72 mmol) and DIAD (145 mg, 0.72 mmol). The reaction mixture was stirred at r.t. for 16 h, and then it was partitioned between EtOAc (50 mL) and H₂O (20 mL). The organic layer was washed with brine (10 mL), dried with anhydrous Na₂SO₄, and concentrated to give the crude product. This residue was purified with silica gel column (hexane/EtOAc=2/1) to afford the desired product as a colorless oil (130 mg, 87%). To a solution of the desired product (130 mg, 0.32 mmol) in DCM (4 mL) was added TFA (1 mL) at 0° C. The mixture was stirred at 0° C. for 1 h. The reaction mixture was concentrated, and the residue was partitioned between EtOAc (50 mL) and 1 N NaHCO₃ (10 mL). The organic layer was washed with brine (10 mL), dried with anhydrous Na₂SO₄, and concentrated to give the crude product. This residue was purified with silica gel column (DCM/MeOH=10/1) to provide HJC-2-96 (100 mg, 98%) as a pale red oil. ¹H NMR (600 MHz, CDCl₃) δ7.64 (d, 2H, J=7.2 Hz), 6.89 (s, 2H), 6.88 (d, 2H, J=7.2 Hz), 5.40-5.48 (bs, 2H), 4.02-4.03 (m, 2H), 3.10-3.12 (m, 2H), 2.52 (s, 6H), 2.23 (s, 3H). ¹³C NMR (150 MHz, CDCl₃) δ 161.6, 143.4, 139.8, 135.7, 134.2, 132.3, 128.5, 114.7, 67.1, 40.0, 22.8, 21.1.

Example 33

2-Fluoro-5-[4-(2,4,6-Trimethyl-Benzenesulfonyl)-Phenyl]-Pyridine (HJC-2-97)

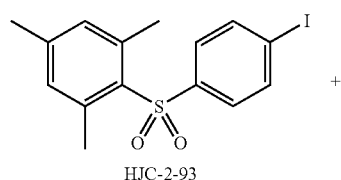

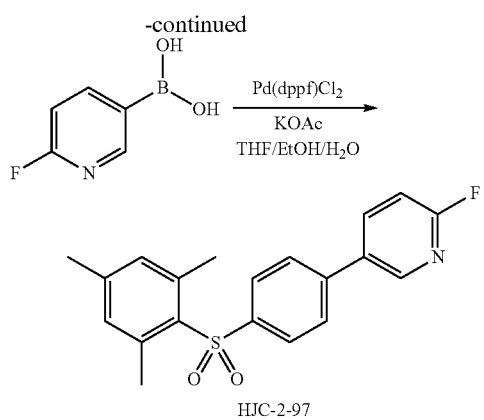

To a solution of HJC-2-93 (77 mg, 0.2 mmol) and 2-Fluoropyridine-5-boronic acid (28 mg, 0.2 mmol) in THF/EtOH/H₂O (1 mL/1 mL/1 mL) was added KOAc (59 mg, 0.6 mmol) and then Pd(dppf)Cl₂ (16 mg, 0.02 mmol). The resulting mixture was deoxygenated via five vacuum/N₂-refill cycles. The mixture was stirred at 80° C. for 18 h, and was then concentrated under vacuum. The residue was partitioned between EtOAc (50 mL) and H₂O (20 mL). The organic layer was separated and washed with brine (10 mL), dried over anhydrous Na₂SO₄, filtrated and concentrated to give an oil residue. This residue was purified with silica gel column (Hexane/EtOAc=3/1) to obtain HJC-2-97 (50 mg, 70%) as a red solid. ¹H NMR (600 MHz, CDCl₃) δ 8.39-8.41 (m, 1H), 7.95-7.98 (m, 1H), 7.88 (d, 2H, J=8.4 Hz), 7.62-7.65 (m, 2H), 7.03 (d, 1H, J=8.4 Hz), 6.96 (s, 2H), 2.61 (s, 6H), 2.30 (s, 3H). ¹³C NMR (150 MHz, CDCl₃) δ 164.5, 162.9, 146.3, 143.8, 143.3, 141.0, 140.2, 140.1, 133.6, 133.2, 132.4, 127.6, 127.2, 110.1, 109.9, 23.0, 21.1.

Example 34

1,2,4-Trimethyl-5-(Toluene-4-Sulfonyl)-Benzene (HJC-2-98)

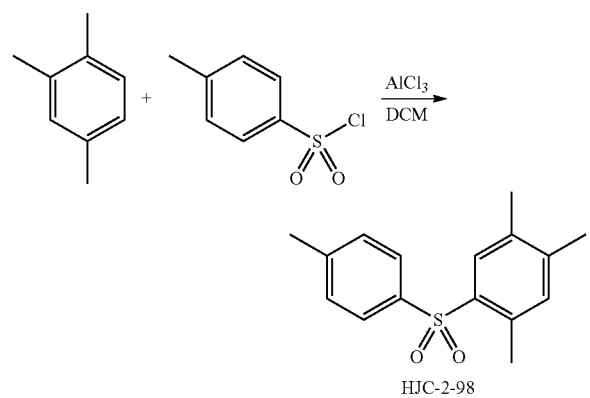

A mixture of 4-methyl-benzenesulfonyl chloride (191 mg, 1.0 mmol), 1,2,4-Trimethyl-benzene (120 mg, 1.0 mmol) and AlCl₃ (200 mg, 1.5 mmol) in DCM (10 mL) was stirred for 2 hours at room temperature. The mixture was then poured into 10 mL of 5% HCl (aq.), and extracted by DCM (30 mL). The organic phase was washed by aqueous KHCO₃, brine, and dried over anhydrous Na₂SO₄. The resulting solution was evaporated, and the residue was purified by silica gel column chromatography (Hexane/EtOAc=10/1) to give the desired product as a white solid (200 mg, 73%). $^1$H NMR (600 MHz, CDCl$_3$) δ 7.96 (s, 1H), 7.73 (d, 2H, J=7.8 Hz), 7.26 (d, 2H, J=7.8 Hz), 6.97 (s, 1H), 2.39 (s, 3H), 2.34 (s, 3H), 2.31 (s, 3H), 2.28 (s, 3H). $^{13}$C NMR (150 MHz, CDCl$_3$) δ 143.7, 143.0, 139.0, 136.2, 135.0, 134.0, 130.3, 129.7, 129.7, 127.6, 21.7, 21.6, 19.7, 19.4.

Example 35

2-(4-Cyclohexyl-Benzenesulfonyl)-1,3,5-Trimethyl-Benzene (HJC-3-1)

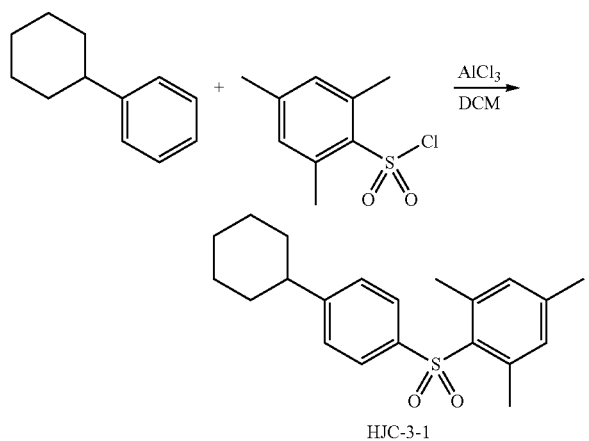

HJC-3-1

A mixture of mesitylsulfonyl chloride (219 mg, 1.0 mmol), cyclohexyl-benzene (160 mg, 1.0 mmol) and AlCl$_3$ (200 mg, 1.5 mmol) in DCM (10 mL) was stirred for 2 hours at room temperature. The mixture was then poured into 10 mL of 5% HCl (aq.), and extracted by DCM (30 mL). The organic phase was washed by aqueous KHCO$_3$, brine, and dried over anhydrous Na$_2$SO$_4$. The resulting solution was evaporated, and the residue was purified by silica gel column chromatography (Hexane/EtOAc=10/1) to give the desired product as a white solid (255 mg, 75%). $^1$H NMR (600 MHz, CDCl$_3$) δ 7.69 (d, 2H, J=8.4 Hz), 7.27 (d, 2H, J=8.4 Hz), 6.93 (s, 2H), 2.60 (s, 6H), 2.52-2.55 (m, 1H), 2.27 (s, 3H), 1.82-1.83 (m, 4H), 1.73-1.75 (m, 1H), 1.34-1.41 (m, 4H), 1.22-1.26 (m, 1H). $^{13}$C NMR (150 MHz, CDCl$_3$) δ 153.3, 143.2, 141.0, 140.0, 134.3, 132.2, 127.4, 126.4, 44.6, 34.2, 26.7, 26.0, 22.9, 21.0.

Example 36

(3,5-Dichloro-Phenyl)-(2,4,6-Trimethyl-Phenyl)-Amine (HJC-2-83)

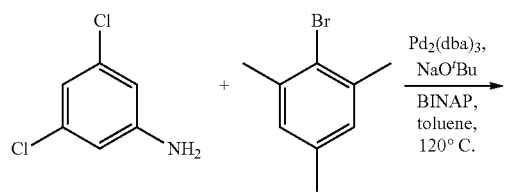

-continued

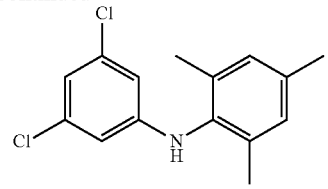

HJC-2-83

NaOtBu (115 mg, 1.2 mmol), Pd$_2$(dba)$_3$ (92 mg, 0.1 mmol) and BINAP (124 mg, 0.2 mmol) were placed into a flask and dissolved into distilled toluene (5 mL). To this solution was added mesityl bromide (995 mg, 5.0 mmol) and 3,5-dichloro-phenylamine (162 mg, 1.0 mmol) dropwise with stirring at room temperature and the mixture was refluxed at 120° C. for 24 h. After the mixture was cooled, 10 mL of 5% HCl (aq.) was added and extracted with EtOAc (50 mL). The combined organic layer was washed with NaHCO$_3$ and dried over anhydrous Na$_2$SO$_4$, filtered and concentrated in vacuo. The residue was purified by silica gel column chromatography (Hexane/EtOAc=10/1) to give the desired product as a pale yellow solid (190 mg, 68%). $^1$H NMR (600 MHz, CDCl$_3$) δ 7.00 (s, 2H), 6.73 (s, 1H), 6.37 (s, 2H), 5.21 (s, 1H), 2.36 (s, 3H), 2.20 (s, 6H). $^{13}$C NMR (150 MHz, CDCl$_3$) δ 148.8, 136.7, 136.4, 135.7, 133.9, 129.6, 117.7, 111.3, 21.0, 18.2.

Example 37

P-Tolyl-(2,4,6-Trimethyl-Phenyl)-Amine (HJC-2-89)

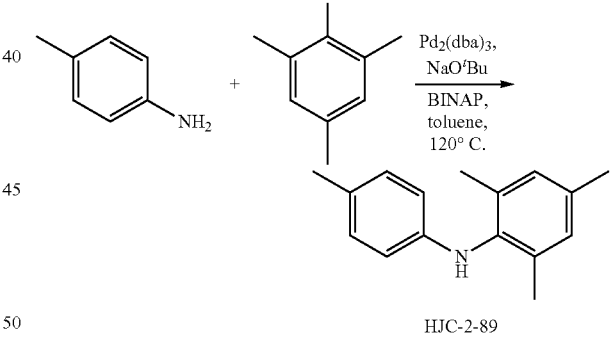

HJC-2-89

NaOtBu (115 mg, 1.2 mmol), Pd$_2$(dba)$_3$ (92 mg, 0.1 mmol) and BINAP (124 mg, 0.2 mmol) were placed into a flask and dissolved into distilled toluene (5 mL). To this solution was added mesityl bromide (995 mg, 5.0 mmol) and p-Tolylamine (107 mg, 1.0 mmol) dropwise with stirring at room temperature and the mixture was refluxed at 120° C. for 24 h. After the mixture was cooled, 10 mL of 5% HCl (aq.) was added and extracted with EtOAc (50 mL). The combined organic layer was washed with NaHCO$_3$ and dried over anhydrous Na$_2$SO$_4$, filtered and concentrated in vacuo. The residue was purified by silica gel column chromatography (Hexane/EtOAc=10/1) to give the desired product as a pale yellow oil (210 mg, 93%). $^1$H NMR (600 MHz, CDCl$_3$) δ 7.11 (d, 2H, J=7.8 Hz), 7.09 (s, 2H), 6.57 (d, 2H, J=7.8 Hz), 5.12 (s, 1H), 2.47 (s, 3H), 2.40 (s, 3H), 2.33 (s, 6H). $^{13}$C NMR (150 MHz, CDCl$_3$) δ 144.4, 136.1, 135.7, 135.1, 129.8, 129.3, 127.1, 113.5, 21.0, 20.5, 18.3.

Example 38

(2,5-Dichloro-Phenyl)-(2,4,6-Trimethyl-Phenyl)-Amine (HJC-3-38)

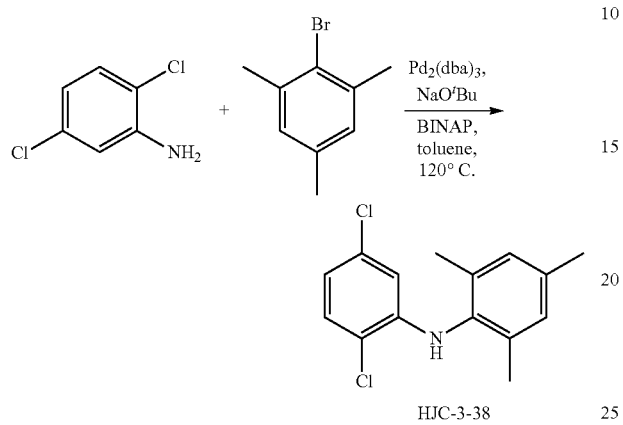

NaOtBu (58 mg, 0.6 mmol), Pd$_2$(dba)$_3$ (46 mg, 0.05 mmol) and BINAP (62 mg, 0.1 mmol) were placed into a flask and dissolved into distilled toluene (5 mL). To this solution was added mesityl bromide (500 mg, 2.5 mmol) and 2,5-Dichloro-phenylamine (81 mg, 0.5 mmol) dropwise with stirring at room temperature and the mixture was refluxed at 120° C. for 24 h. After the mixture was cooled, 10 mL of 5% HCl (aq.) was added and extracted with EtOAc (50 mL). The combined organic layer was washed with NaHCO$_3$ and dried over anhydrous Na$_2$SO$_4$, filtered and concentrated in vacuo. The residue was purified by silica gel column chromatography (Hexane/EtOAc=10/1) to give the desired product as a pale yellow solid (87 mg, 62%). $^1$H NMR (600 MHz, CDCl$_3$) δ 7.22 (d, 1H, J=8.4 Hz), 6.98 (s, 2H), 6.62 (dd, 1H, J$_1$=7.8 Hz, J$_2$=1.8 Hz), 6.14 (d, 1H, J=2.4 Hz), 5.67 (s, 1H), 2.33 (s, 3H), 2.16 (s, 6H). $^{13}$C NMR (150 MHz, CDCl$_3$) δ 143.8, 136.9, 136.5, 133.9, 133.8, 130.1, 129.6, 117.8, 117.2, 112.1, 21.1, 18.1.

Example 39

(4,5-Dimethyl-Thiazol-2-Yl)-(2,4,6-Trimethyl-Phenyl)-Amine (HJC-3-49)

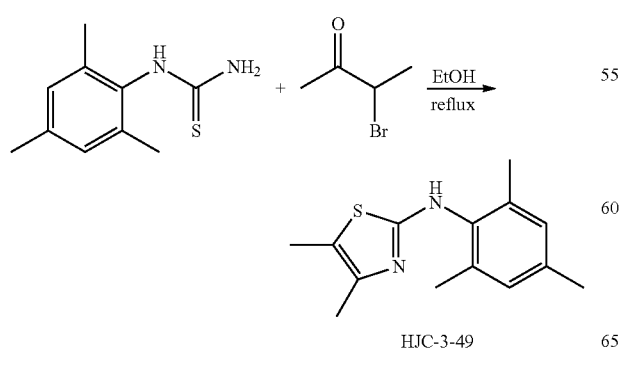

To a solution of (2,4,6-Trimethyl-phenyl)-thiourea (49 mg, 0.25 mmol) in EtOH (5 mL) was added 3-Bromo-butan-2-one (38 mg, 0.25 mmol). The mixture was stirred at 90° C. for 1 h. The solution was diluted with EtOAc (30 mL), washed with H$_2$O (10 mL) and brine (10 mL). The organic layer was dried over Na$_2$SO$_4$, and then concentrated under reduced pressure. The residue was purified by silica gel column chromatography (hexane/EtOAc=3/1) to give the desired product as a pale yellow solid (40 mg, 65%). $^1$H NMR (600 MHz, CDCl$_3$) δ 7.70-8.00 (bs, 1H), 6.94 (s, 2H), 2.30 (s, 3H), 2.27 (s, 6H), 2.09 (s, 3H), 2.02 (s, 3H). $^{13}$C NMR (150 MHz, CDCl$_3$) δ 167.4, 143.1, 137.4, 136.9, 135.5, 129.5, 113.2, 21.1, 18.2, 14.5, 11.1.

Example 40

1-(2,4,6-Trimethyl-Benzenesulfonyl)-1H-Indole (HJC-2-77)

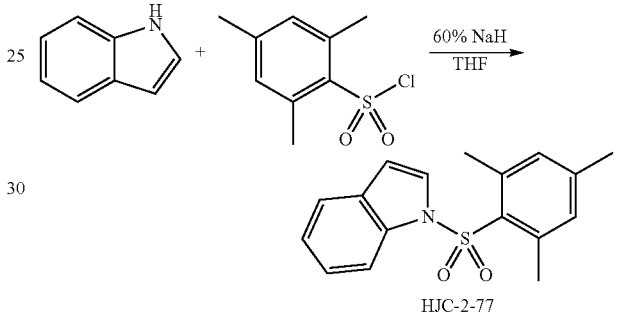

To a solution of 1H-Indole (117 mg, 1.0 mmol) and mesitylsulfonyl chloride (219 mg, 1.0 mmol) in 5 mL of THF was added 60% NaH (50 mg, 1.25 mmol) at 0° C. The resulting mixture was stirred at r.t. for 16 h. The solution was diluted with EtOAc (50 mL), washed with 1 N HCl (aq.) (10 mL) and brine (10 mL). The organic layer was dried over anhydrous Na$_2$SO$_4$ and then concentrated under reduced pressure. The residue was purified by silica gel column chromatography (Hexane/EtOAc=10/1) to give the desired product as a white solid (250 mg, 84%). $^1$H NMR (600 MHz, CDCl$_3$) δ 7.59-7.61 (m, 1H), 7.54-7.55 (m, 1H), 7.34-7.35 (m, 1H), 7.17 (s, 2H), 6.93 (s, 2H), 6.61-6.62 (m, 1H), 2.52 (s, 6H), 2.26 (s, 3H). $^{13}$C NMR (150 MHz, CDCl$_3$) δ 144.1, 140.3, 134.7, 133.1, 132.5, 130.3, 126.8, 124.2, 122.8, 121.5, 112.5, 106.5, 22.7, 21.1.

Example 41

2-Ethyl-1-(2,4,6-Trimethyl-Benzenesulfonyl)-1H-Pyrrole (HJC-2-79)

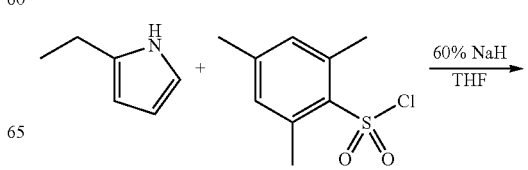

-continued

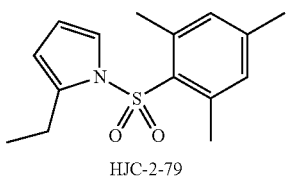

HJC-2-79

To a solution of 2-ethyl-1H-pyrrole (~80% purity) (24 mg, 0.25 mmol) and mesitylsulfonyl chloride (110 mg, 0.5 mmol) in 5 mL of THF was added 60% NaH (24 mg, 0.6 mmol) at 0° C. The resulting mixture was stirred at r.t. for 16 h. The solution was diluted with EtOAc (50 mL), washed with 1 N HCl (aq.) (10 mL) and brine (10 mL). The organic layer was dried over anhydrous $Na_2SO_4$ and then concentrated under reduced pressure. The residue was purified by silica gel column chromatography (Hexane/EtOAc=10/1) to give the desired product as a pale yellow oil (20 mg, 36%). $^1$H NMR (600 MHz, $CDCl_3$) δ 7.29-7.30 (m, 1H), 6.95 (s, 2H), 6.13-6.14 (m, 1H), 5.96-5.98 (m, 1H), 2.46 (s, 6H), 2.34-2.38 (m, 2H), 2.31 (s, 3H), 1.07 (t, 3H, J=7.2 Hz). $^{13}$C NMR (150 MHz, $CDCl_3$) δ 144.0, 140.2, 136.5, 133.5, 132.3, 122.3, 110.0, 109.1, 22.4, 21.2, 19.3, 12.4.

Example 42

(1H-Indol-5-Yl)-Piperidin-1-Yl-Methanone (HJC-1-21)

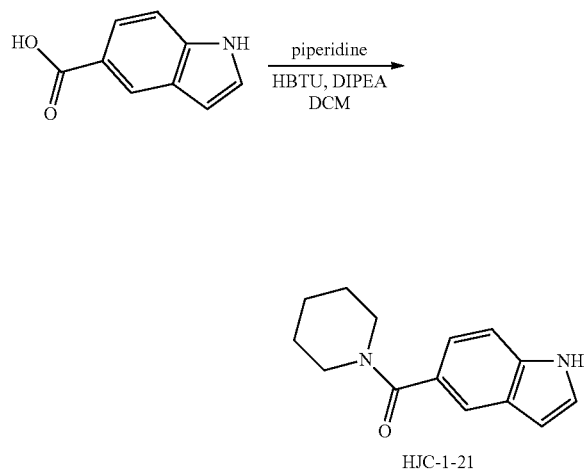

HJC-1-21

To a solution of 1H-Indole-5-carboxylic acid (323 mg, 2.0 mmol) in 10 mL of DCM was added DIPEA (1.29 g, 10.0 mmol) and piperidine (852 mg, 10.0 mmol). HBTU (1.14 g, 3.0 mmol) was added at 0° C. The resulting mixture was stirred at r.t. for 18 h. TLC indicated that the starting material was gone. The mixture was diluted with DCM (100 mL) and washed with water (30 mL). The organic layer was separated and dried over anhydrous $Na_2SO_4$. The solution was concentrated to give a crude product, which was purified with silica gel column (DCM/EtOAc/Hexane=1/1/1) to obtain HJC-1-21 (410 mg, 90%) as a white solid. $^1$H NMR (600 MHz, $CDCl_3$) δ 8.85 (s, 1H), 7.70 (s, 1H), 7.28-7.34 (m, 1H), 7.19-7.24 (m, 2H), 6.54-6.56 (m, 1H), 3.46-3.74 (m, 4H), 1.48-1.77 (m, 6H).

Example 43

Piperidin-1-Yl-[1-(2,4,6-Trimethyl-Benzenesulfonyl)-1H-Indol-5-Yl]-Methanone (HJC-2-80)

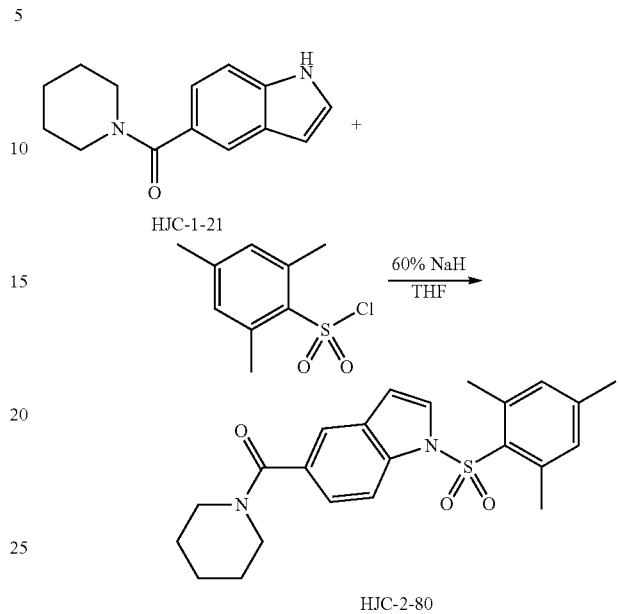

HJC-2-80

To a solution of HJC-1-21 (42 mg, 0.18 mmol) and mesitylsulfonyl chloride (40 mg, 0.18 mmol) in 5 mL of THF was added 60% NaH (9 mg, 0.22 mmol) at 0° C. The resulting mixture was stirred at r.t. for 16 h. The solution was diluted with EtOAc (50 mL), washed with 1 N HCl (aq.) (10 mL) and brine (10 mL). The organic layer was dried over anhydrous $Na_2SO_4$ and then concentrated under reduced pressure. The residue was purified by silica gel column chromatography (Hexane/EtOAc=1/1) to give the desired product as a white solid (70 mg, 93%). $^1$H NMR (600 MHz, $CDCl_3$) δ 7.63-7.64 (m, 1H), 7.61-7.62 (m, 1H), 7.32-7.34 (m, 1H), 7.20-7.21 (m, 1H), 6.95 (s, 2H), 6.64-6.66 (m, 1H), 3.65-3.70 (m, 2H), 3.30-3.36 (m, 2H), 2.50 (s, 6H), 2.28 (s, 3H), 1.51-1.67 (m, 6H). $^{13}$C NMR (150 MHz, $CDCl_3$) δ 170.6, 144.4, 140.3, 134.9, 132.7, 132.6, 131.3, 130.0, 127.7, 123.1, 120.3, 112.4, 106.7, 49.0, 43.3, 26.6, 25.8, 24.7, 22.7, 21.1.

Example 44

1-(2,4,6-Trimethyl-Benzenesulfonyl)-1H-Pyrrolo[2,3-B]Pyridine (HJC-2-81)

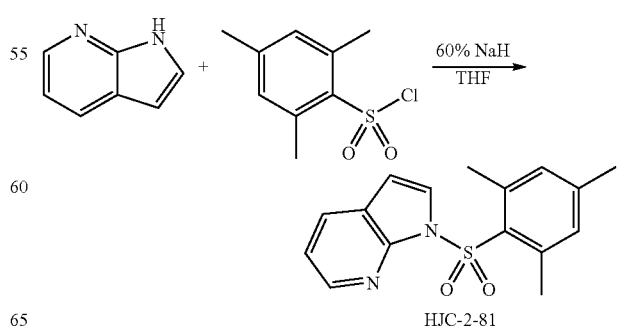

HJC-2-81

To a solution of 1H-Pyrrolo[2,3-b]pyridine (59 mg, 0.5 mmol) and mesitylsulfonyl chloride (110 mg, 0.5 mmol) in 4 mL of THF was added 60% NaH (24 mg, 0.6 mmol) at 0° C. The resulting mixture was stirred at r.t. for 16 h. The solution was diluted with EtOAc (50 mL), washed with 1 N HCl (aq.) (10 mL) and brine (10 mL). The organic layer was dried over anhydrous $Na_2SO_4$ and then concentrated under reduced pressure. The residue was purified by silica gel column chromatography (Hexane/EtOAc=7/1) to give the desired product as a white solid (130 mg, 87%). $^1$H NMR (600 MHz, $CDCl_3$) δ 8.22 (d, 1H, J=4.2 Hz), 7.85 (d, 1H, J=3.0 Hz), 7.83 (d, 1H, J=7.8 Hz), 7.08-7.11 (m, 1H), 6.93 (s, 2H), 6.57 (d, 1H, J=3.0 Hz), 2.71 (s, 6H), 2.27 (s, 3H). $^{13}$C NMR (150 MHz, $CDCl_3$) δ 147.6, 144.7, 144.0, 141.3, 132.8, 132.1, 129.3, 126.9, 122.4, 118.6, 103.8, 23.0, 21.2.

Example 45

1-(2,4,6-Trimethyl-Benzenesulfonyl)-1H-Pyrrolo[2,3-C]Pyridine (HJC-3-21)

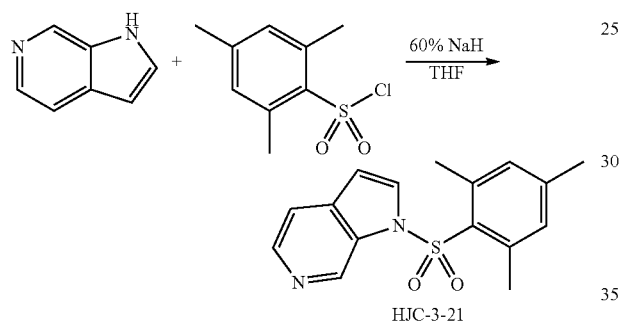

To a solution of 1H-Pyrrolo[2,3-c]pyridine (35 mg, 0.3 mmol) and mesitylsulfonyl chloride (66 mg, 0.3 mmol) in 4 mL of THF was added 60% NaH (16 mg, 0.4 mmol) at 0° C. The resulting mixture was stirred at r.t. for 16 h. The solution was diluted with EtOAc (50 mL), washed with 1 N HCl (aq.) (10 mL) and brine (10 mL). The organic layer was dried over anhydrous $Na_2SO_4$ and then concentrated under reduced pressure. The residue was purified by silica gel column chromatography (Hexane/EtOAc=1/1) to give the desired product as a white solid (78 mg, 87%). $^1$H NMR (600 MHz, $CDCl_3$) δ 8.69 (s, 1H), 8.35 (d, 1H, J=5.4 Hz), 7.73 (d, 1H, J=3.6 Hz), 7.48 (d, 1H, J=5.4 Hz), 6.96 (s, 2H), 6.63 (d, 1H, J=3.0 Hz), 2.53 (s, 6H), 2.28 (s, 3H). $^{13}$C NMR (150 MHz, $CDCl_3$) δ 144.9, 142.1, 140.6, 135.8, 135.1, 132.8, 132.4, 131.8, 130.0, 115.9, 105.5, 22.7, 21.2.

Example 46

1-(2,4,6-Trimethyl-Benzenesulfonyl)-1H-Pyrrolo[3,2-C]Pyridine (HJC-3-22)

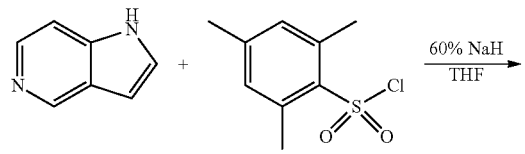

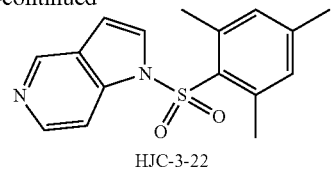

HJC-3-22

To a solution of 1H-Pyrrolo[3,2-c]pyridine (35 mg, 0.3 mmol) and mesitylsulfonyl chloride (66 mg, 0.3 mmol) in 4 mL of THF was added 60% NaH (16 mg, 0.4 mmol) at 0° C. The resulting mixture was stirred at r.t. for 16 h. The solution was diluted with EtOAc (50 mL), washed with 1 N HCl (aq.) (10 mL) and brine (10 mL). The organic layer was dried over anhydrous $Na_2SO_4$ and then concentrated under reduced pressure. The residue was purified by silica gel column chromatography (Hexane/EtOAc=1/1) to give the desired product as a white solid (76 mg, 84%). $^1$H NMR (600 MHz, $CDCl_3$) δ 8.88 (s, 1H), 8.33 (d, 1H, J=6.0 Hz), 7.54 (d, 1H, J=3.6 Hz), 7.29 (d, 1H, J=5.4 Hz), 6.95 (s, 2H), 6.68 (d, 1H, J=3.6 Hz), 2.50 (s, 6H), 2.26 (s, 3H). $^{13}$C NMR (150 MHz, $CDCl_3$) δ 144.8, 144.3, 143.6, 140.4, 139.0, 132.6, 132.3, 127.2, 126.4, 107.6, 105.1, 22.6, 21.1.

Example 47

1-(2,4,6-Trimethyl-Benzenesulfonyl)-1H-Pyrrolo[3,2-B]Pyridine (HJC-3-23)

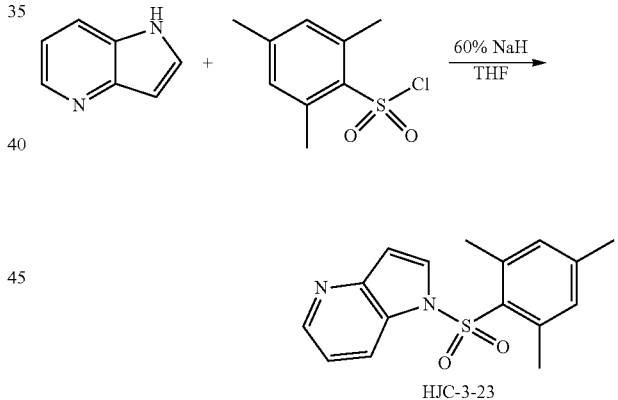

To a solution of 1H-Pyrrolo[3,2-b]pyridine (35 mg, 0.3 mmol) and mesitylsulfonyl chloride (88 mg, 0.4 mmol) in 4 mL of THF was added 60% NaH (16 mg, 0.4 mmol) at 0° C. The resulting mixture was stirred at r.t. for 16 h. The solution was diluted with EtOAc (50 mL), washed with 1 N HCl (aq.) (10 mL) and brine (10 mL). The organic layer was dried over anhydrous $Na_2SO_4$ and then concentrated under reduced pressure. The residue was purified by silica gel column chromatography (Hexane/EtOAc=1/1) to give the desired product as a white solid (86 mg, 96%). $^1$H NMR (600 MHz, $CDCl_3$) δ 8.48 (d, 1H, J=3.6 Hz), 7.74-7.75 (m, 1H), 7.71 (d, 1H, J=8.4 Hz), 7.09-7.11 (m, 1H), 6.94 (s, 2H), 6.81 (d, 1H, J=3.0 Hz), 2.50 (s, 6H), 2.25 (s, 3H). $^{13}$C NMR (150 MHz, $CDCl_3$) δ 148.1, 145.8, 144.7, 140.4, 132.6, 132.5, 129.6, 128.3, 119.8, 118.7, 107.8, 22.7, 21.1.

Example 48

1-(2,4,6-Trimethyl-Benzenesulfonyl)-1H-Indole-5-Carboxylic Acid Methyl Ester (HJC-3-24)

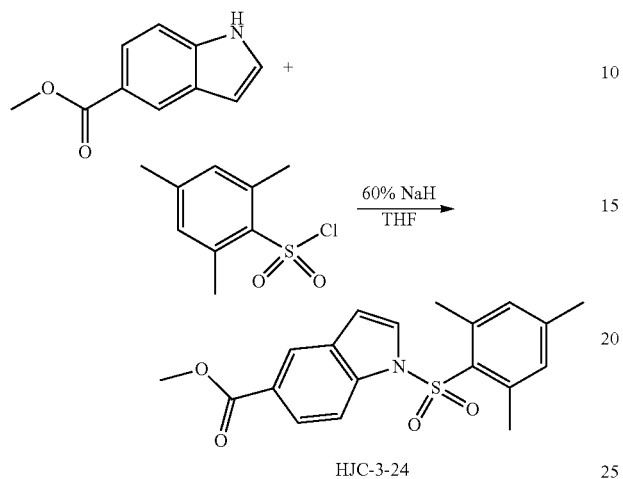

To a solution of 1H-Indole-5-carboxylic acid methyl ester (88 mg, 0.5 mmol) and mesitylsulfonyl chloride (131 mg, 0.6 mmol) in 5 mL of THF was added 60% NaH (24 mg, 0.6 mmol) at 0° C. The resulting mixture was stirred at r.t. for 16 h. The solution was diluted with EtOAc (50 mL), washed with 1 N HCl (aq.) (10 mL) and brine (10 mL). The organic layer was dried over anhydrous $Na_2SO_4$ and then concentrated under reduced pressure. The residue was purified by silica gel column chromatography (Hexane/EtOAc=3/1) to give the desired product as a white solid (150 mg, 84%). $^1$H NMR (600 MHz, $CDCl_3$) δ 8.30 (s, 1H), 7.88 (d, 1H, J=9.0 Hz), 7.64 (d, 1H, J=3.6 Hz), 7.40 (d, 1H, J=8.4 Hz), 6.95 (s, 2H), 6.70 (d, 1H, J=3.6 Hz), 3.90 (s, 3H), 2.51 (s, 6H), 2.28 (s, 3H). $^{13}$C NMR (150 MHz, $CDCl_3$) δ 167.3, 144.6, 140.4, 137.3, 132.8, 132.6, 130.0, 128.0, 125.6, 125.1, 123.9, 112.3, 107.1, 52.2, 22.7, 21.2.

Example 49

2-Ethyl-1-(Toluene-4-Sulfonyl)-1H-Pyrrole (HJC-3-26)

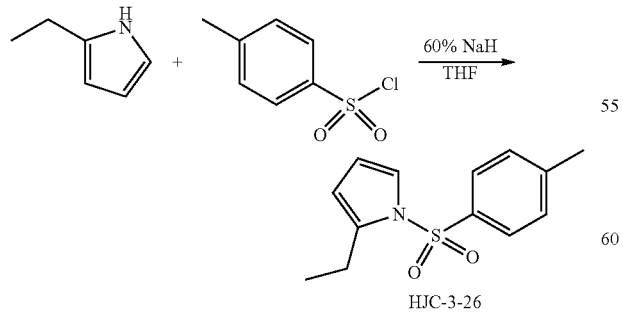

To a solution of 2-ethyl-1H-pyrrole (~80% purity) (24 mg, 0.25 mmol) and 4-methyl-benzenesulfonyl chloride (95 mg, 0.5 mmol) in 5 mL of THF was added 60% NaH (24 mg, 0.6 mmol) at 0° C. The resulting mixture was stirred at r.t. for 16 h. The solution was diluted with EtOAc (50 mL), washed with 1 N HCl (aq.) (10 mL) and brine (10 mL). The organic layer was dried over anhydrous $Na_2SO_4$ and then concentrated under reduced pressure. The residue was purified by silica gel column chromatography (Hexane/EtOAc=10/1) to give the desired product as a colorless oil (15 mg, 30%). $^1$H NMR (600 MHz, $CDCl_3$) δ 7.64 (d, 2H, J=8.4 Hz), 7.28 (d, 2H, J=8.4 Hz), 7.27 (d, 1H, J=8.4 Hz), 6.20 (t, 1H, J=3.0 Hz), 5.99 (d, 1H, J=3.0 Hz), 2.68 (q, 2H, J=7.2 Hz), 2.40 (s, 3H), 1.16 (t, 3H, J=7.2 Hz). $^{13}$C NMR (150 MHz, $CDCl_3$) δ 144.8, 137.5, 136.7, 130.1, 126.9, 122.4, 111.3, 111.1, 21.7, 20.6, 12.8.

Example 50

2-Ethyl-1-(4-Methoxy-Benzenesulfonyl)-1H-Pyrrole (HJC-3-44)

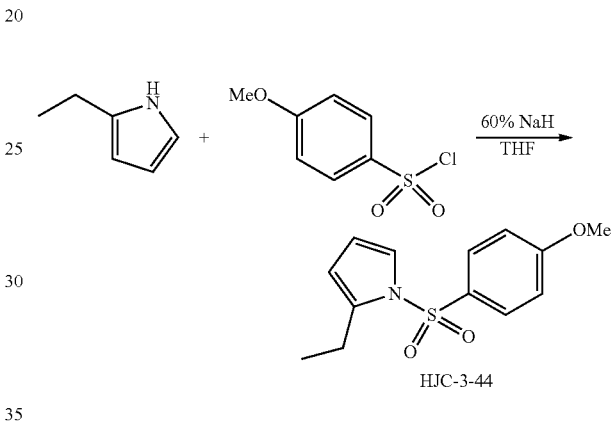

To a solution of 2-ethyl-1H-pyrrole (~80% purity) (24 mg, 0.25 mmol) and 4-methoxy-benzenesulfonyl chloride (153 mg, 0.75 mmol) in 5 mL of THF was added 60% NaH (32 mg, 0.8 mmol) at 0° C. The resulting mixture was stirred at r.t. for 16 h. The solution was diluted with EtOAc (50 mL), washed with 1 N HCl (aq.) (10 mL) and brine (10 mL). The organic layer was dried over anhydrous $Na_2SO_4$ and then concentrated under reduced pressure. The residue was purified by silica gel column chromatography (Hexane/EtOAc=10/1) to give the desired product as a pale red solid (20 mg, 38%). $^1$H NMR (600 MHz, $CDCl_3$) δ 7.72 (d, 2H, J=10.2 Hz), 7.28 (t, 1H, J=1.2 Hz), 6.95 (d, 2H, J=11.4 Hz), 6.19 (t, 1H, J=3.0 Hz), 5.99 (d, 1H, J=1.8 Hz), 3.85 (s, 3H), 2.69 (q, 2H, J=7.8 Hz), 1.16 (t, 3H, J=7.2 Hz). $^{13}$C NMR (150 MHz, $CDCl_3$) δ 163.7, 137.4, 131.1, 129.2, 122.2, 114.7, 111.2, 111.0, 55.8, 20.6, 12.8.

Example 51

1-(4-Chloro-Benzenesulfonyl)-2-Ethyl-1H-Pyrrole (HJC-3-45)

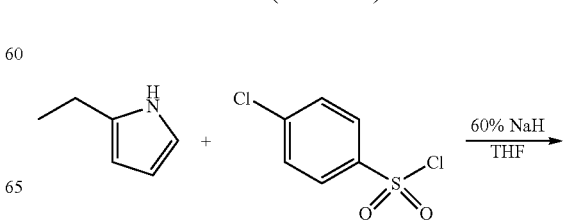

-continued

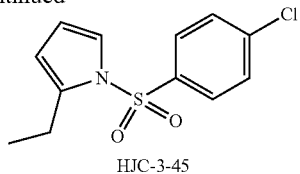

HJC-3-45

To a solution of 2-ethyl-1H-pyrrole (=80% purity) (24 mg, 0.25 mmol) and 4-chloro-benzenesulfonyl chloride (211 mg, 1.0 mmol) in 5 mL of THF was added 60% NaH (40 mg, 1.0 mmol) at 0° C. The resulting mixture was stirred at r.t. for 16 h. The solution was diluted with EtOAc (50 mL), washed with 1 N HCl (aq.) (10 mL) and brine (10 mL). The organic layer was dried over anhydrous $Na_2SO_4$ and then concentrated under reduced pressure. The residue was purified by silica gel column chromatography (Hexane/EtOAc=10/1) to give the desired product as a pale red solid (41 mg, 76%). $^1$H NMR (600 MHz, $CDCl_3$) δ 7.68 (d, 2H, J=7.2 Hz), 7.47 (d, 2H, J=7.2 Hz), 7.27 (d, 1H, J=3.6 Hz), 6.23 (t, 1H, J=3.6 Hz), 6.02 (d, 1H, J=3.6 Hz), 2.68 (q, 2H, J=7.2 Hz), 1.18 (t, 3H, J=7.2 Hz). $^{13}$C NMR (150 MHz, $CDCl_3$) δ 140.4, 138.1, 137.6, 129.8, 128.3, 122.4, 111.9, 111.6, 20.7, 12.8.

Example 52

2-Ethyl-1-(4-Trifluoromethyl-Benzenesulfonyl)-1H-Pyrrole (HJC-3-47)

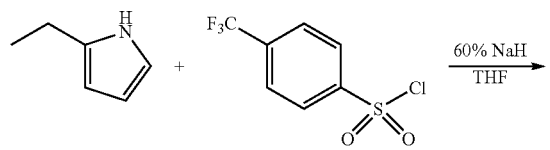

HJC-3-47

To a solution of 2-ethyl-1H-pyrrole (~80% purity) (24 mg, 0.25 mmol) and 4-Trifluoromethyl-benzenesulfonyl chloride (245 mg, 1.0 mmol) in 5 mL of THF was added 60% NaH (40 mg, 1.0 mmol) at 0° C. The resulting mixture was stirred at r.t. for 16 h. The solution was diluted with EtOAc (50 mL), washed with 1 N HCl (aq.) (10 mL) and brine (10 mL). The organic layer was dried over anhydrous $Na_2SO_4$ and then concentrated under reduced pressure. The residue was purified by silica gel column chromatography (Hexane/EtOAc=10/1) to give the desired product as a pale red solid (35 mg, 58%). $^1$H NMR (600 MHz, $CDCl_3$) δ 7.86 (d, 2H, J=7.8 Hz), 7.76 (d, 2H, J=7.8 Hz), 7.28-2.30 (m, 1H), 6.25 (d, 1H, J=1.8 Hz), 6.03-6.05 (m, 1H), 2.68 (q, 2H, J=7.2 Hz), 1.18 (t, 3H, J=7.8 Hz).

Example 53

2,4-Dimethyl-1-(2,4,6-Trimethyl-Benzenesulfonyl)-1H-Pyrrole (HJC-3-50)

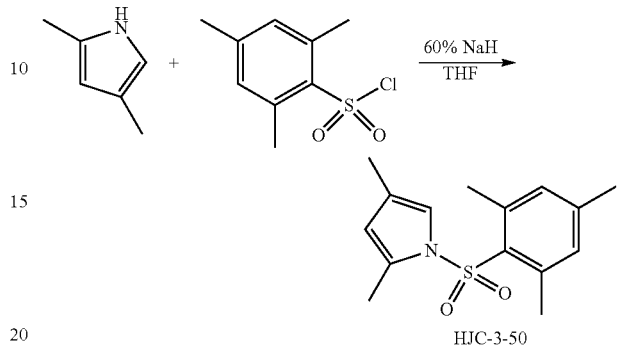

HJC-3-50

To a solution of 2,4-dimethyl-1H-pyrrole (24 mg, 0.25 mmol) and mesitylsulfonyl chloride (218 mg, 1.0 mmol) in 5 mL of THF was added 60% NaH (40 mg, 1.0 mmol) at 0° C. The resulting mixture was stirred at r.t. for 16 h. The solution was diluted with EtOAc (50 mL), washed with 1 N HCl (aq.) (10 mL) and brine (10 mL). The organic layer was dried over anhydrous $Na_2SO_4$ and then concentrated under reduced pressure. The residue was purified by silica gel column chromatography (Hexane/EtOAc=10/1) to give the desired product as a pale red solid (40 mg, 58%). $^1$H NMR (600 MHz, $CDCl_3$) δ 7.01 (s, 1H), 6.95 (s, 2H), 5.77 (s, 1H), 2.49 (s, 6H), 2.31 (s, 3H), 2.00 (s, 3H), 1.99 (s, 3H). $^{13}$C NMR (150 MHz, $CDCl_3$) δ 143.8, 140.2, 133.8, 132.2, 130.2, 119.7, 119.2, 114.5, 23.4, 21.1, 12.6, 11.8.

Example 54

2-Ethyl-1-(Toluene-2-Sulfonyl)-1H-Pyrrole (HJC-3-53)

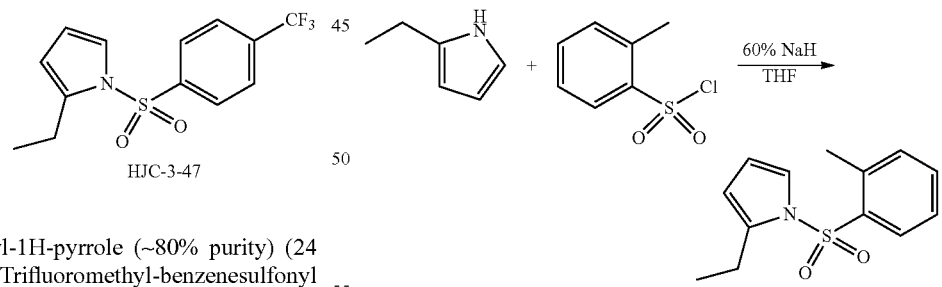

HJC-3-53

To a solution of 2-ethyl-1H-pyrrole (~80% purity) (48 mg, 0.5 mmol) and 2-methyl-benzenesulfonyl chloride (191 mg, 1.0 mmol) in 5 mL of THF was added 60% NaH (40 mg, 1.0 mmol) at 0° C. The resulting mixture was stirred at r.t. for 16 h. The solution was diluted with EtOAc (50 mL), washed with 1 N HCl (aq.) (10 mL) and brine (10 mL). The organic layer was dried over anhydrous $Na_2SO_4$ and then concentrated under reduced pressure. The residue was purified by silica gel column chromatography (Hexane/EtOAc=10/1) to give the desired product as a pale red solid (73 mg, 73%). $^1$H NMR (600 MHz, CDCl$_3$) δ 7.50 (d, 2H, J=7.2 Hz), 7.31-7.36 (m, 3H), 6.24-6.26 (m, 1H), 6.07-6.09 (m, 1H), 2.55 (q, 2H, J=7.2 Hz), 2.54 (s, 3H), 1.13 (t, 3H, J=7.2 Hz). $^{13}$C NMR (150 MHz, CDCl$_3$) δ 138.6, 138.0, 137.6, 133.7, 132.9, 128.3, 126.5, 123.0, 110.7, 110.3, 20.3, 20.0, 12.6.

Example 55

1-(3,5-Dimethyl-Benzenesulfonyl)-2-Ethyl-1H-Pyrrole (HJC-3-54)

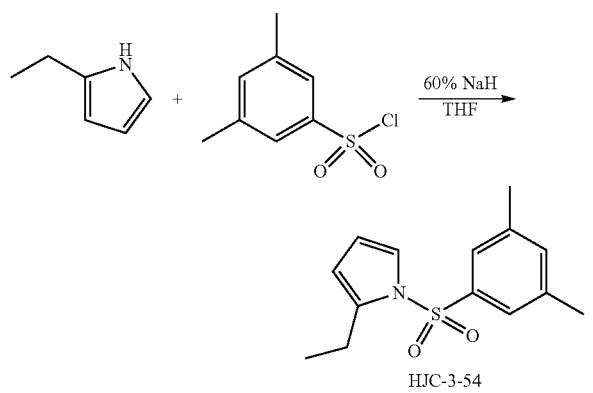

To a solution of 2-ethyl-1H-pyrrole (~80% purity) (48 mg, 0.5 mmol) and 3,5-dimethylbenzenesulfonyl chloride (150 mg, 0.75 mmol) in 5 mL of THF was added 60% NaH (40 mg, 1.0 mmol) at 0° C. The resulting mixture was stirred at r.t. for 16 h. The solution was diluted with EtOAc (50 mL), washed with 1 N HCl (aq.) (10 mL) and brine (10 mL). The organic layer was dried over anhydrous Na$_2$SO$_4$ and then concentrated under reduced pressure. The residue was purified by silica gel column chromatography (Hexane/EtOAc=10/1) to give the desired product as a pale red solid (70 mg, 67%). $^1$H NMR (600 MHz, CDCl$_3$) δ 7.36 (s, 2H), 7.29 (s, 1H), 7.19 (s, 1H), 6.21 (t, 1H, J=3.0 Hz), 6.00 (s, 1H), 2.70 (q, 2H, J=7.2 Hz), 2.35 (s, 6H), 1.17 (t, 3H, J=7.2 Hz). $^{13}$C NMR (150 MHz, CDCl$_3$) δ 139.6, 139.4, 137.5, 135.5, 124.3, 122.4, 111.2, 111.0, 21.4, 20.6, 12.9.

Example 56

1-(2,4-Dimethyl-Benzenesulfonyl)-2-Ethyl-1H-Pyrrole (HJC-3-55)

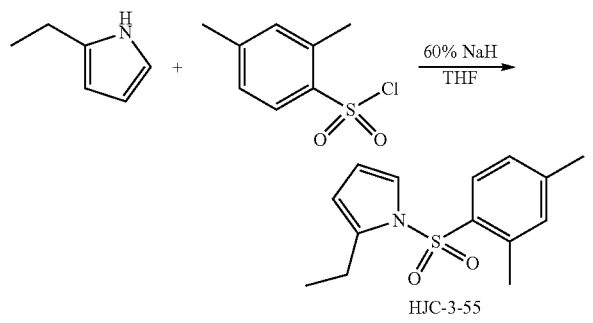

To a solution of 2-ethyl-1H-pyrrole (~80% purity) (48 mg, 0.5 mmol) and 2,4-dimethylbenzenesulfonyl chloride (150 mg, 0.75 mmol) in 5 mL of THF was added 60% NaH (40 mg, 1.0 mmol) at 0° C. The resulting mixture was stirred at r.t. for 16 h. The solution was diluted with EtOAc (50 mL), washed with 1 N HCl (aq.) (10 mL) and brine (10 mL). The organic layer was dried over anhydrous Na$_2$SO$_4$ and then concentrated under reduced pressure. The residue was purified by silica gel column chromatography (Hexane/EtOAc=10/1) to give the desired product as a white solid (80 mg, 76%). $^1$H NMR (600 MHz, CDCl$_3$) δ 7.46 (d, 1H, J=7.2 Hz), 7.33-7.35 (m, 1H), 7.10-7.12 (m, 2H), 6.22-6.24 (m, 1H), 6.04-6.06 (m, 1H), 2.55 (q, 2H, J=7.2 Hz), 2.47 (s, 3H), 2.39 (s, 3H), 1.13 (t, 3H, J=7.2 Hz). $^{13}$C NMR (150 MHz, CDCl$_3$) δ 144.7, 137.9, 137.4, 135.5, 133.6, 128.7, 127.1, 122.9, 110.6, 110.1, 21.4, 20.3, 19.8, 12.6.

Example 57

1-(2,4,6-Trimethyl-Benzenesulfonyl)-1H-Indole-5-Carboxylic Acid (HJC-3-62)

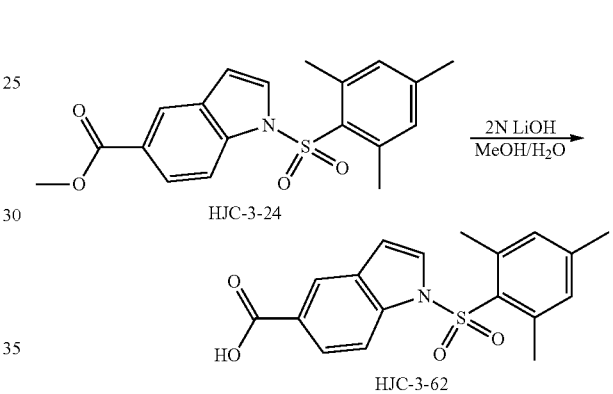

To a solution of HJC-3-24 (72 mg, 0.2 mmol) in MeOH/H$_2$O (4 mL/1 mL) was added 2N LiOH (0.4 mL, 0.8 mmol). The mixture was stirred at r.t. for 16 h. The solution was diluted with EtOAc (30 mL), washed with 1 N HCl (aq.) (10 mL) and brine (10 mL). The organic layer was dried over Na$_2$SO$_4$, and then concentrated under reduced pressure. The residue was purified by silica gel column chromatography (hexane/EtOAc=1/1) to give the desired product as a pale yellow solid (45 mg, 66%). $^1$H NMR (600 MHz, DMSO-d6) δ 12.80 (bs, 1H), 8.27-8.29 (m, 1H), 7.85-7.86 (m, 2H), 7.40-7.42 (m, 1H), 7.15-7.17 (m, 2H), 6.93-6.95 (m, 1H), 2.45 (s, 6H), 2.28 (s, 3H).

Example 58

1-P-Tolyl-4-(2,4,6-Trimethyl-Benzenesulfonyl)-Piperazine (HJC-3-42)

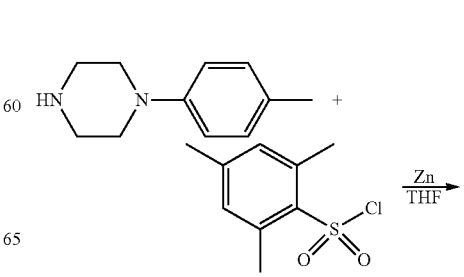

-continued

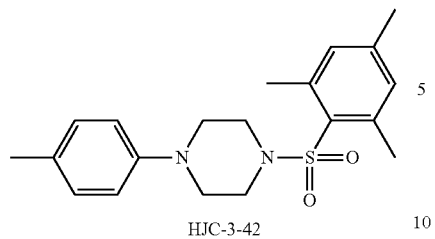

HJC-3-42

To a solution of 1-p-Tolyl-piperazine (44 mg, 0.25 mmol) and mesitylsulfonyl chloride (55 mg, 0.25 mmol) in 5 mL of THF was added Zn (32 mg, 0.5 mmol) at 0° C. The resulting mixture was stirred at r.t. for 16 h and then was concentrated under reduced pressure. The residue was purified by silica gel column chromatography (Hexane/EtOAc=3/1) to give the desired product as a pale red solid (80 mg, 89%). $^1$H NMR (600 MHz, CDCl$_3$) δ 7.08 (d, 2H, J=8.4 Hz), 6.98 (s, 2H), 6.82 (d, 2H, J=7.8 Hz), 3.32 (t, 4H, J=4.8 Hz), 3.13 (t, 4H, J=4.8 Hz), 2.66 (s, 6H), 2.32 (s, 3H), 2.27 (s, 3H). $^{13}$C NMR (150 MHz, CDCl$_3$) δ 148.9, 142.8, 140.7, 132.1, 131.5, 130.3, 129.9, 117.2, 49.8, 44.5, 23.1, 21.1, 20.5.

Example 59

1-Pyridin-2-Yl-4-(2,4,6-Trimethyl-Benzenesulfonyl)-Piperazine (HJC-3-48)

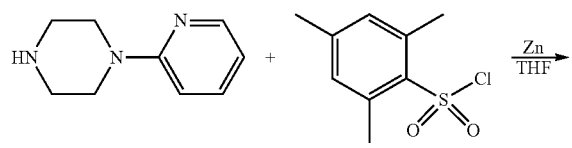

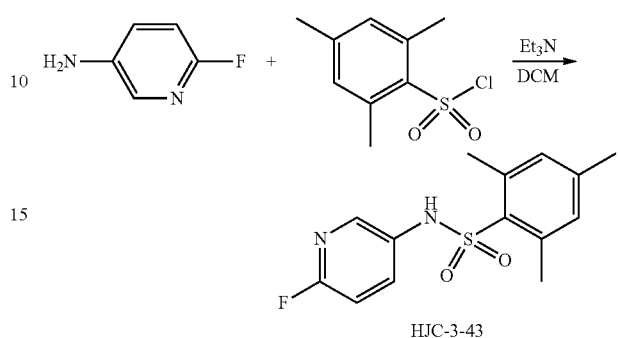

HJC-3-48

To a solution of 1-pyridin-2-yl-piperazine (41 mg, 0.25 mmol) and mesitylsulfonyl chloride (55 mg, 0.25 mmol) in 5 mL of THF was added Zn (33 mg, 0.5 mmol) at 0° C. The resulting mixture was stirred at r.t. for 16 h and then was concentrated under reduced pressure. The residue was purified by silica gel column chromatography (Hexane/EtOAc=3/1) to give the desired product as a pale red solid (85 mg, 99%). $^1$H NMR (600 MHz, CDCl$_3$) δ 8.17-8.18 (m, 1H), 7.46-7.49 (m, 1H), 6.96 (s, 2H), 6.62-6.66 (m, 2H), 3.58 (t, 4H, J=4.8 Hz), 3.27 (t, 4H, J=4.8 Hz), 2.65 (s, 6H), 2.30 (s, 3H). $^{13}$C NMR (150 MHz, CDCl$_3$) δ 150.1, 148.1, 142.9, 140.7, 137.7, 132.1, 131.4, 114.1, 107.4, 45.0, 44.2, 23.0, 21.1.

Example 60

N-(6-Fluoro-Pyridin-3-Yl)-2,4,6-Trimethyl-Benzenesulfonamide (HJC-3-43)

HJC-3-43

To a solution of 6-Fluoro-pyridin-3-ylamine (56 mg, 0.5 mmol) and mesitylsulfonyl chloride (109 mg, 0.5 mmol) in 5 mL of DCM was added Et$_3$N (79 mg, 1.0 mmol) at 0° C. The resulting mixture was stirred at r.t. for 16 h. The solution was diluted with EtOAc (50 mL), washed with 1 N HCl (aq.) (10 mL) and brine (10 mL). The organic layer was dried over anhydrous Na$_2$SO$_4$ and then concentrated under reduced pressure. The residue was purified by silica gel column chromatography (Hexane/EtOAc=3/1) to give the desired product as a white solid (100 mg, 68%). $^1$H NMR (600 MHz, CDCl$_3$) δ 10.35 (s, 1H), 7.79 (s, 1H), 7.53-7.56 (m, 1H), 7.09-7.11 (m, 1H), 7.02 (s, 2H), 2.50 (s, 6H), 2.23 (s, 3H). $^{13}$C NMR (150 MHz, CDCl$_3$) δ 160.3, 158.7, 142.4, 139.1, 139.0, 138.6, 134.3, 134.2, 133.1, 132.4, 132.4, 131.8, 110.1, 109.8, 22.3, 20.3.

Example 61

N-(2,6-Dimethoxy-Pyridin-3-Yl)-2,4,6-Trimethyl-Benzenesulfonamide (HJC-3-46)

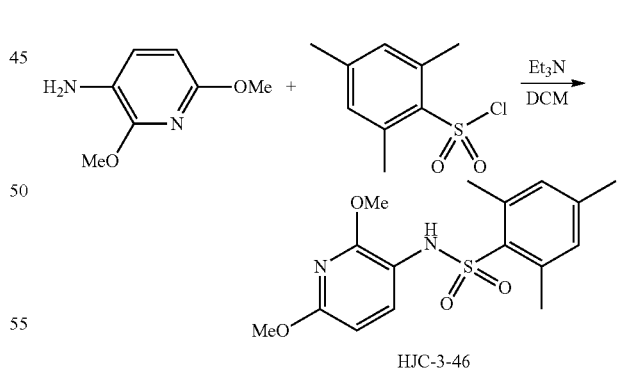

HJC-3-46

To a solution of 2,6-dimethoxy-pyridin-3-ylamine (48 mg, 0.25 mmol) and mesitylsulfonyl chloride (65 mg, 0.3 mmol) in 2 mL of EtOAc and 2 mL of H$_2$O was added Na$_2$CO$_3$ (80 mg, 0.75 mmol) at 0° C. The resulting mixture was stirred at r.t. for 16 h. The solution was diluted with EtOAc (50 mL), washed with 1 N HCl (aq.) (10 mL) and brine (10 mL). The organic layer was dried over anhydrous Na$_2$SO$_4$ and then concentrated under reduced pressure. The residue was purified by silica gel column chromatography (Hexane/EtOAc=3/1) to give the desired product as a pale red solid (83 mg, 99%). $^1$H NMR (600 MHz, CDCl$_3$) δ 7.57 (d, 1H, J=8.4 Hz), 6.86 (s, 2H), 6.57 (s, 1H), 6.22 (d, 1H, J=9.0 Hz), 3.81 (s, 3H), 3.69 (s, 3H), 2.55 (s, 6H), 2.25 (s, 3H). $^{13}$C NMR (150 MHz, CDCl$_3$) δ 160.5, 155.0, 142.4, 139.7, 135.6, 133.7, 131.8, 112.8, 101.0, 53.8, 53.5, 23.1, 21.0.

Example 62

N-(5-Tert-Butyl-Isoxazol-3-Yl)-2-[(3-Chlorophenyl)-Hydrazono]-2-Cyanoacetamide (HJC0683)

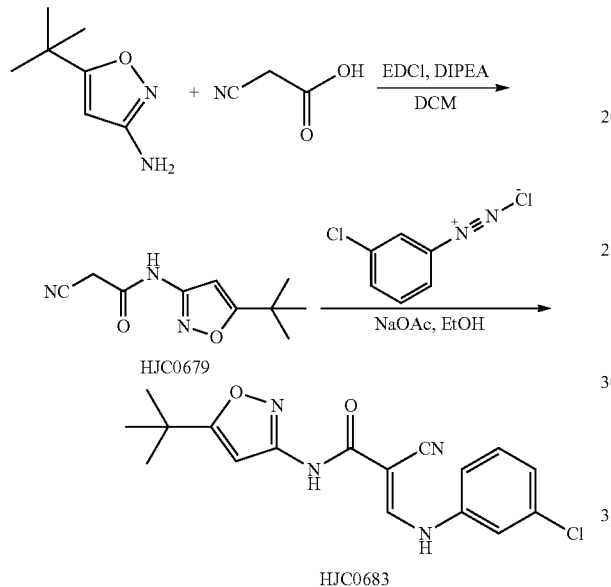

To a solution of 5-tert-butyl-isoxazol-3-ylamine (140 mg, 1.0 mmol) and cyanoacetic acid (85 mg, 1.0 mmol) in 10 mL of DCM was added DIPEA (258 mg, 2.0 mmol). EDCI (191 mg, 1.0 mmol) was added at 0° C. The resulting mixture was stirred at r.t. for 16 h. The solution was diluted with DCM (50 mL), washed with 1 N HCl (aq.) (10 mL) and brine (10 mL). The organic layer was dried over anhydrous Na$_2$SO$_4$, and then concentrated under reduced pressure. The residue was purified by silica gel column chromatography (hexane/EtOAc=1/1) to give the desired product HJC0679 as a white solid (163 mg, 90%). $^1$H NMR (600 MHz, CDCl$_3$) δ 10.59 (s, 1H), 6.70 (s, 1H), 3.65 (s, 2H), 1.36 (s, 9H). $^{13}$C NMR (150 MHz, CDCl$_3$) δ 182.9, 159.8, 157.6, 113.4, 93.7, 33.4, 28.7, 26.9.

To a solution of 3-chloroaniline (25 mg, 0.2 mmol) in H$_2$O (1 mL cooled to −5° C.) was added 0.2 mL of 1 N HCl (aq.). To the resulting acidic aniline solution, 1 mL solution of sodium nitrite (14 mg, 0.2 mmol) in H$_2$O was added dropwise to generate the aryldiazonium salt solution. To the aryldiazonium salt solution was added sodium acetate (33 mg, 0.4 mmol), followed by 1 mL solution of HJC0679 (29 mg, 0.14 mmol) in ethanol. The reaction mixture was stirred at 0° C. for 5 min, and then poured onto H$_2$O (2 mL) and extracted with ethyl acetate (20 mL). The organic layer was dried over Na$_2$SO$_4$, filtered and concentrated under reduced pressure. The residue was purified by short column chromatography on silica gel eluting with hexane/ethyl acetate (2/1) to provide the desired product HJC0683 (32 mg, 66) as a yellow solid. HPLC purity 96.7% ($t_R$=20.97 min). $^1$H NMR (600 MHz, DMSO-d$_6$) δ 12.04 (s, 1H), 11.22 (s, 1H), 7.98 (s, 1H), 7.69 (d, 1H, J=9.0 Hz), 7.40 (t, 1H, J=7.8 Hz), 7.17 (d, 1H, J=7.8 Hz), 6.63 (s, 1H), 1.32 (s, 9H). $^{13}$C NMR (150 MHz, DMSO-d$_6$) δ 180.2, 159.5, 157.2, 143.0, 133.6, 130.4, 123.8, 115.8, 115.0, 110.6, 107.9, 93.6, 32.2, 28.1. HRMS (ESI) calcd for C$_{16}$H$_{17}$ClN$_5$O$_2$ 346.1065 (M+H)$^+$. found 346.1074.

Example 63

2-[(3-Chlorophenyl)-Hydrazono]-2-Cyano-N-(5-Methyl-Isoxazol-3-Yl)Acetamide (HJC0692)

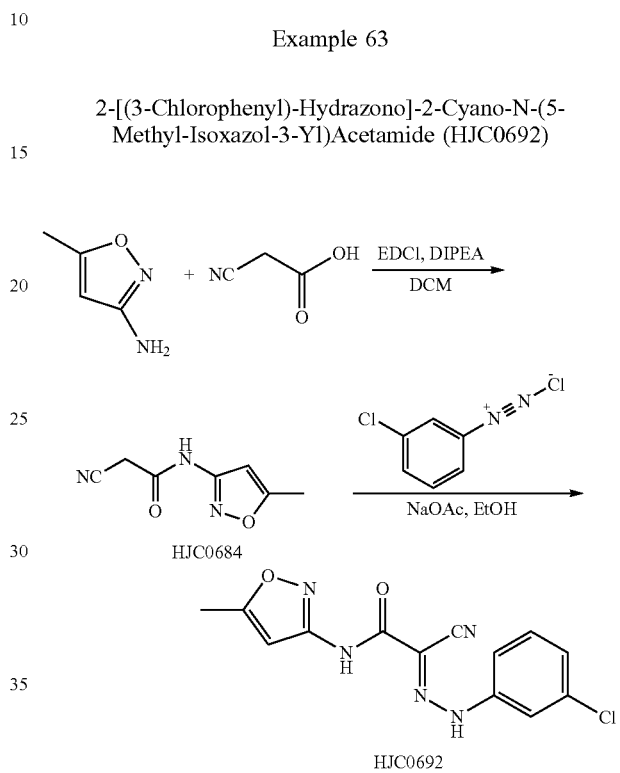

Compound HJC0692 was prepared in 53% yield (two steps) by a procedure similar to that used to prepare compound HJC0683. The title compound was obtained as a yellow solid. HPLC purity 98.5% ($t_R$=18.55 min). $^1$H NMR (600 MHz, DMSO-d$_6$) δ 12.03 (s, 1H), 11.19 (s, 1H), 7.98 (s, 1H), 7.69 (d, 1H, J=8.4 Hz), 7.39 (t, 1H, J=7.8 Hz), 7.18 (d, 1H, J=6.6 Hz), 6.67 (s, 1H), 2.43 (s, 3H). $^{13}$C NMR (150 MHz, DMSO-d$_6$) δ 169.6, 159.8, 157.9, 143.4, 133.9, 130.7, 124.1, 116.1, 115.3, 110.9, 108.3, 97.0, 12.2. HRMS (ESI) calcd for C$_{13}$H$_{11}$ClN$_5$O$_2$ 304.0596 (M+H)$^+$. found 304.0606.

Example 64

3-(5-Tert-Butyl-Isoxazol-3-Yl)-2-[(3-Chlorophenyl)-Hydrazono]-3-Oxo-Propionitrile (HJC0680, ESI-09)

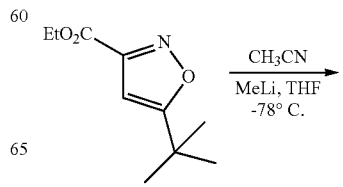

-continued

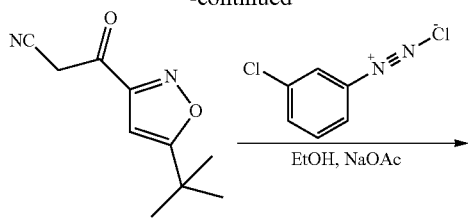

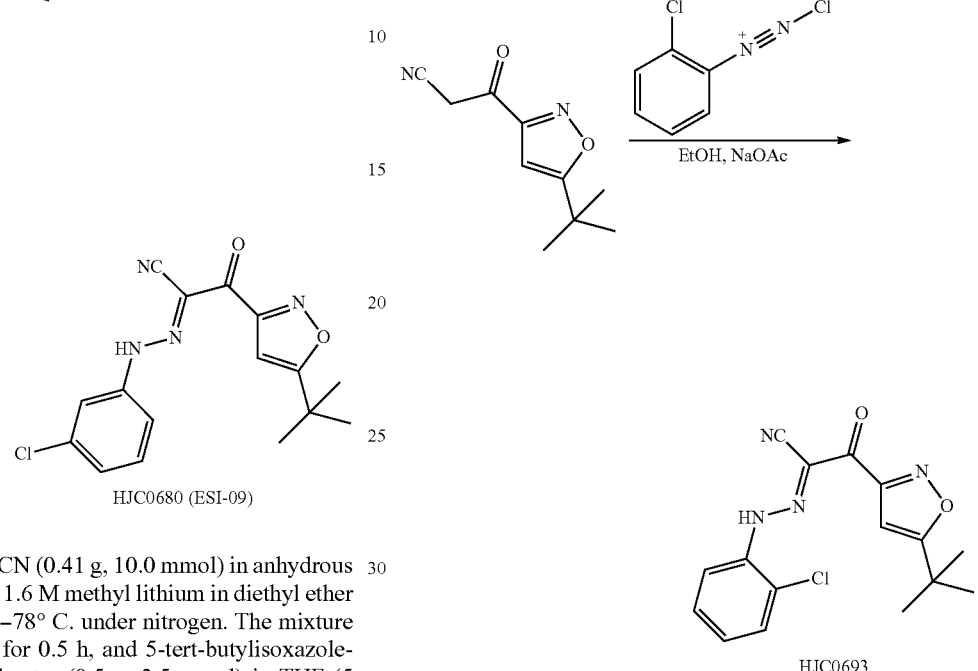

Example 65

3-(5-Tert-Butyl-Isoxazol-3-Yl)-2-[(2-Chlorophenyl)-Hydrazono]-3-Oxo-Propionitrile (HJC0693)

To a solution of CH$_3$CN (0.41 g, 10.0 mmol) in anhydrous THF (5 mL) was added 1.6 M methyl lithium in diethyl ether (3.1 mL, 5.0 mmol) at −78° C. under nitrogen. The mixture was stirred at −78° C. for 0.5 h, and 5-tert-butylisoxazole-3-carboxylic acid ethyl ester (0.5 g, 2.5 mmol) in THF (5 mL) was then added dropwise. The solution was stirred at −78° C. for 1 h and then quenched with acetic acid (0.3 g, 5.0 mmol). The mixture was warmed to 0° C. and poured onto ice/water (10 mL) and extracted with ethyl acetate (50 mL). The organic lay was dried over Na$_2$SO$_4$, filtered and concentrated under reduced pressure. The crude residue (490 mg) was obtained as a yellow oil and directly used for next step without further purification.

To a solution of 3-chloroaniline (30 mg, 0.24 mmol) in H$_2$O (1 mL cooled to −5° C.) was added 0.24 mL of 1 N HCl (aq.). To the resulting acidic aniline solution, 1 mL solution of sodium nitrite (16 mg, 0.24 mmol) in H$_2$O was added dropwise to generate the aryldiazonium salt solution. To the aryldiazonium salt solution was added sodium acetate (33 mg, 0.4 mmol), followed by 1 mL solution of crude 3-(5-tert-butylisoxazol-3-yl)-3-oxo-propionitrile (38 mg, 0.2 mmol) in ethanol. The reaction mixture was stirred at 0° C. for 5 min, and then poured onto H$_2$O (2 mL) and extracted with ethyl acetate (20 mL). The organic layer was dried over Na$_2$SO$_4$, filtered and concentrated under reduced pressure. The residue was purified by short column chromatography on silica gel eluting with hexane/ethyl acetate (2/1) to provide the desired product ESI-09 (40 mg, 61%, two steps from 5-tert-butylisoxazole-3-carboxylic acid ethyl ester) as a yellow solid (mp 146-147° C.). HPLC purity 99.6% ($t_R$=21.72 min). $^1$H NMR (600 MHz, DMSO-d$_6$) δ 12.70 (br s, 1H), 7.44-7.47 (m, 3H), 7.25-7.26 (m, 1H), 6.70 (s, 1H), 1.39 (s, 9H). $^{13}$C NMR (150 MHz, DMSO-d$_6$) δ 181.1, 179.4, 160.1, 143.6, 134.0, 131.2, 125.1, 116.2, 115.8, 113.4, 110.5, 100.4, 32.5, 28.5.

HRMS (ESI) calcd for C$_{16}$H$_{16}$ClN$_4$O$_2$ 331.0956 (M+H)$^+$. found 331.0969.

Compound HJC0693 was prepared in 76% yield (two steps from 5-tert-butylisoxazole-3-carboxylic acid ethyl ester) by a procedure similar to that used to prepare compound HJC0680. The title compound was obtained as a yellow solid. HPLC purity 96.6% ($t_R$=22.77 min). $^1$H NMR (600 MHz, DMSO-d$_6$) δ 7.53-7.60 (m, 1H), 7.47-7.52 (m, 1H), 7.37-7.46 (m, 1H), 7.22-7.36 (m, 1H), 6.66 (s, 1H), 1.34 (s, 9H). $^{13}$C NMR (150 MHz, DMSO-d$_6$) δ 180.8, 178.6, 159.9, 139.3, 129.9, 128.1, 126.9, 123.5, 119.6, 114.4, 110.7, 99.9, 32.3, 28.2. HRMS (ESI) calcd for C$_{16}$H$_{16}$ClN$_4$O$_2$ 331.0956 (M+H)$^+$. found 331.0969.

Example 66

3-(5-Ter T-Butyl-Isoxazol-3-Yl)-2-[(4-Chlorophenyl)-Hydrazono]-3-Oxo-Propionitrile (HJC0694)

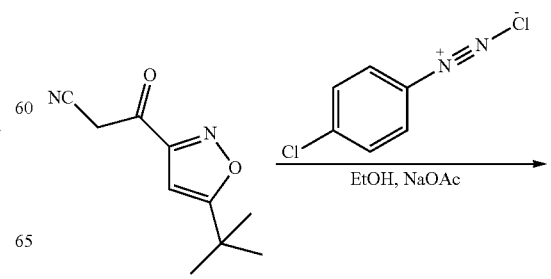

-continued

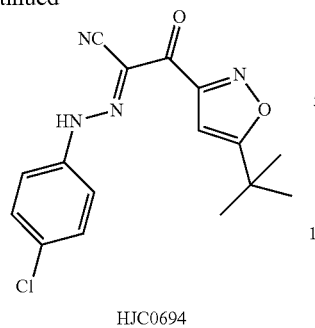

HJC0694

Compound HJC0694 was prepared in 75% yield (two steps from 5-tert-butylisoxazole-3-carboxylic acid ethyl ester) by a procedure similar to that used to prepare compound HJC0680. The title compound was obtained as a yellow solid. HPLC purity 98.1% ($t_R$=21.74 min). $^1$H NMR (600 MHz, DMSO-$d_6$) (7.46-7.60 (m, 4H), 6.64 (s, 1H), 1.36 (s, 9H). $^{13}$C NMR (150 MHz, DMSO-$d_6$) δ 181.5, 179.6, 160.8, 142.5, 130.1, 129.9, 119.2, 113.3, 111.6, 100.8, 33.0, 29.0. HRMS (ESI) calcd for $C_{16}H_{16}ClN_4O_2$ 331.0956 (M+H)$^+$. found 331.0963.

Example 67

3-(5-Tert-Butyl-Isoxazol-3-Yl)-3-Oxo-2-(Phenyl-Hydrazono)-Propionitrile (HJC0695)

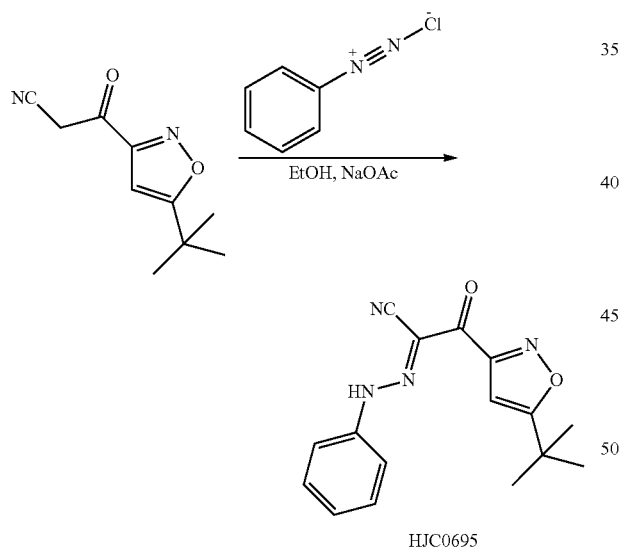

HJC0695

Compound HJC0695 was prepared in 76% yield (two steps from 5-tert-butylisoxazole-3-carboxylic acid ethyl ester) by a procedure similar to that used to prepare compound HJC0680. The title compound was obtained as a yellow solid. HPLC purity 99.4% ($t_R$=20.50 min). $^1$H NMR (600 MHz, DMSO-$d_6$) δ 12.60 (bs, 1H), 7.49 (d, 2H, J=7.8 Hz), 7.42 (d, 2H, J=7.8 Hz), 7.20-7.23 (m, 1H), 6.66 (s, 1H), 1.37 (s, 9H). $^{13}$C NMR (150 MHz, DMSO-$d_6$) δ 180.8, 179.2, 160.0, 142.1, 129.3, 125.6, 116.8, 112.2, 110.7, 100.2, 32.4, 28.3.
HRMS (ESI) calcd for $C_{16}H_{17}N_4O_2$ 297.1346 (M+H)$^+$. found 297.1355.

Example 68

3-(5-Tert-Butyl-Isoxazol-3-Yl)-2-[(2,5-Dichlorophenyl)-Hydrazono]-3-Oxo-Propionitrile (HJC0696)

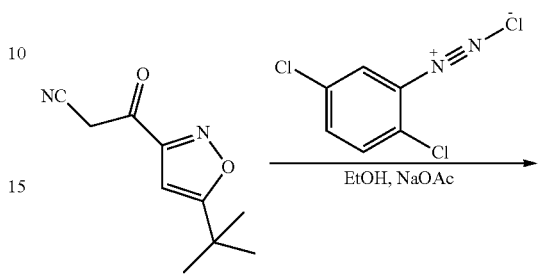

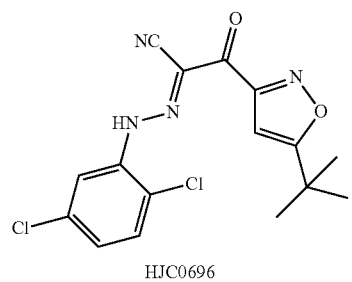

HJC0696

Compound HJC0696 was prepared in 62% yield (two steps from 5-tert-butylisoxazole-3-carboxylic acid ethyl ester) by a procedure similar to that used to prepare compound HJC0680. The title compound was obtained as a yellow solid. HPLC purity 97.1% ($t_R$=23.69 min). $^1$H NMR (600 MHz, DMSO-$d_6$) δ 7.45-7.54 (m, 1H), 7.34 (s, 1H), 7.13-7.22 (m, 1H), 6.56 (s, 1H), 1.37 (s, 9H). $^{13}$C NMR (150 MHz, DMSO-$d_6$) δ 180.4, 179.6, 162.1, 147.3, 132.8, 132.0, 125.7, 125.4, 118.7, 114.4, 113.7, 100.8, 31.2, 29.0. HRMS (ESI) calcd for $C_{16}H_{15}Cl_2N_4O_2$ 365.0567 (M+H)$^+$. found 365.0576.

Example 69

3-(5-Tert-Butyl-Isoxazol-3-Yl)-3-Oxo-2-(M-Tolyl-Hydrazono)Propionitrile (HJC0712)

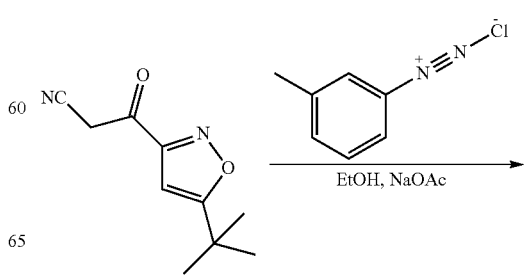

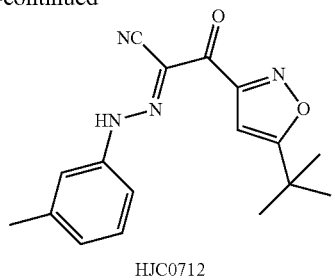

HJC0712

Compound HJC0712 was prepared in 50% yield (two steps from 5-tert-butylisoxazole-3-carboxylic acid ethyl ester) by a procedure similar to that used to prepare compound HJC0680. The title compound was obtained as a yellow solid. HPLC purity 99.0% ($t_R$=21.29 min). $^1$H NMR (600 MHz, DMSO-$d_6$) δ 12.74 (s, 1H), 7.29-7.35 (m, 2H), 7.28 (s, 1H), 7.03-7.05 (m, 1H), 6.68 (s, 1H), 2.30 (s, 3H), 1.37 (s, 9H). $^{13}$C NMR (150 MHz, DMSO-$d_6$) δ 180.9, 179.4, 160.0, 142.0, 138.9, 129.3, 126.5, 117.0, 114.4, 112.3, 110.7, 100.3, 32.4, 28.4, 21.1. HRMS (ESI) calcd for $C_{17}H_{19}N_4O_2$ 311.1503 (M+H)$^+$. found 311.1514.

Example 70

3-(5-Tert-Butyl-Isoxazol-3-Yl)-3-Oxo-2-[(3-Trifluoromethyl-Phenyl)-Hydrazono]Propionitrile (HJC0720)

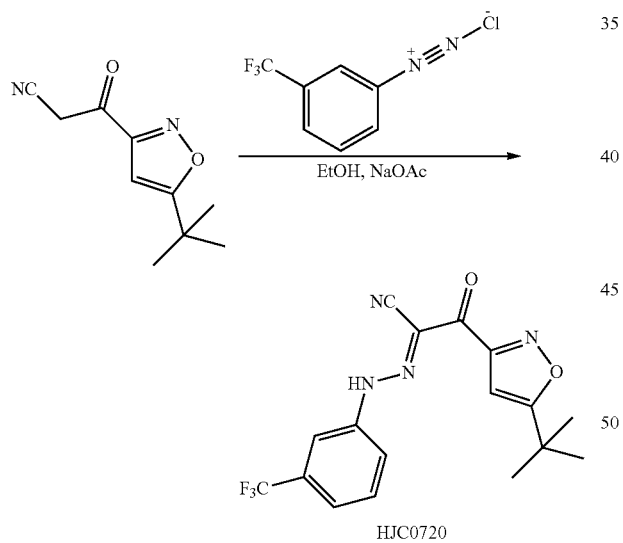

HJC0720

Compound HJC0720 was prepared in 33% yield (two steps from 5-tert-butylisoxazole-3-carboxylic acid ethyl ester) by a procedure similar to that used to prepare compound HJC0680. The title compound was obtained as a yellow solid. HPLC purity 96.0% ($t_R$=21.80 min). $^1$H NMR (600 MHz, DMSO-$d_6$) δ 7.72-7.73 (m, 1H), 7.69 (s, 1H), 7.61-7.64 (m, 1H), 7.49-7.50 (m, 1H), 6.61 (s, 1H), 1.35 (s, 9H). $^{13}$C NMR (150 MHz, DMSO-$d_6$) δ 180.7, 179.3, 160.7, 130.6, 130.2, 130.0, 124.9, 123.1, 122.0, 121.4, 113.3, 111.8, 100.3, 100.2, 32.5, 28.6, 28.5. HRMS (ESI) calcd for $C_{17}H_{16}F_3N_4O_2$ 365.1220 (M+H)$^+$. found 365.1230.

Example 71

3-(5-Tert-Butyl-Isoxazol-3-Yl)-2-[(3-Nitrophenyl)-Hydrazono]-3-Oxo-Propionitrile (HJC0721)

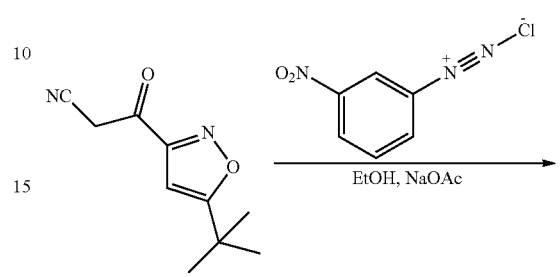

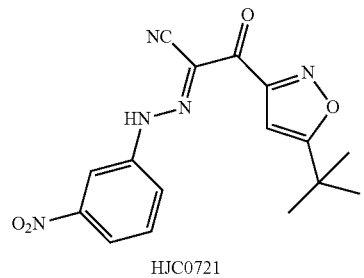

HJC0721

Compound HJC0721 was prepared in 29% yield (two steps from 5-tert-butylisoxazole-3-carboxylic acid ethyl ester) by a procedure similar to that used to prepare compound HJC0680. The title compound was obtained as a yellow solid. HPLC purity 96.4% ($t_R$=20.33 min). $^1$H NMR (600 MHz, DMSO-$d_6$) δ 12.03 (s, 1H), 8.19 (s, 1H), 7.97 (d, 1H, J=8.4 Hz), 7.85 (d, 1H, J=7.8 Hz), 7.67 (t, 1H, J=7.8 Hz), 6.62 (s, 1H), 1.37 (s, 9H). $^{13}$C NMR (150 MHz, DMSO-$d_6$) δ 180.5, 179.0, 171.9, 160.8, 148.5, 130.7, 124.6, 119.1, 113.4, 112.1, 111.2, 100.1, 32.4, 28.4. HRMS (ESI) calcd for $C_{16}H_{16}N_5O_4$ 342.1197 (M+H)$^+$. found 342.1207.

Example 72

3-(5-Tert-Butyl-Isoxazol-3-Yl)-3-Oxo-2-(P-Tolyl-Hydrazono)Propionitrile (HJC0724)

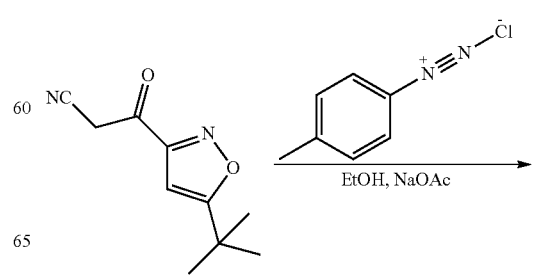

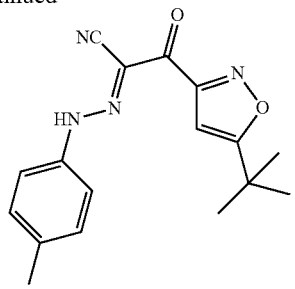

HJC0724

Compound HJC0724 was prepared in 31% yield (two steps from 5-tert-butylisoxazole-3-carboxylic acid ethyl ester) by a procedure similar to that used to prepare compound HJC0680. The title compound was obtained as a yellow solid. HPLC purity 98.6% ($t_R$=21.36 min). $^1$H NMR (600 MHz, DMSO-$d_6$) δ 12.70 (bs, 1H), 7.38 (d, 2H, J=7.8 Hz), 7.22 (d, 2H, J=8.4 Hz), 6.64 (s, 1H), 2.29 (s, 3H), 1.36 (s, 9H). $^{13}$C NMR (150 MHz, DMSO-$d_6$) δ 181.0, 179.5, 160.3, 140.0, 135.5, 130.0, 117.0, 112.0, 111.0, 100.4, 32.6, 28.6, 20.6. HRMS (ESI) calcd for $C_{17}H_{19}N_4O_2$ 311.1503 (M+H)$^+$. found 311.1515.

Example 73

3-(5-Tert-Butyl-Isoxazol-3-Yl)-2-[(3,5-Dichlorophenyl)-Hydrazono]-3-Oxo-Propionitrile (HJC0726)

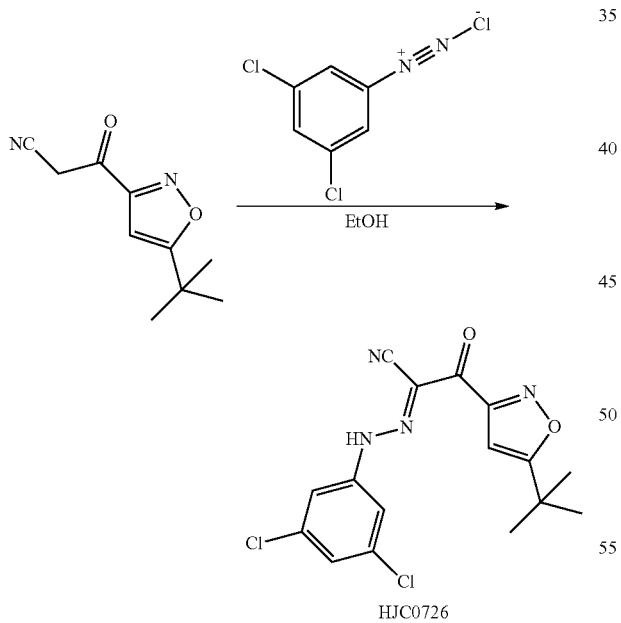

HJC0726

Compound HJC0726 was prepared in 41% yield (two steps from 5-tert-butylisoxazole-3-carboxylic acid ethyl ester) by a procedure similar to that used to prepare compound HJC0680. The title compound was obtained as a yellow solid. HPLC purity 99.0% ($t_R$=23.20 min). $^1$H NMR (600 MHz, DMSO-$d_6$) δ 12.90 (s, 1H), 7.41 (s, 2H), 7.38 (s, 1H), 6.68 (s, 1H), 1.37 (s, 9H). $^{13}$C NMR (150 MHz, DMSO-$d_6$) δ 180.9, 179.2, 160.2, 145.7, 134.8, 124.1, 115.6, 114.0, 110.8, 100.3, 32.4, 28.4. HRMS (ESI) calcd for $C_{16}H_{15}Cl_2N_4O_2$ 365.0567 (M+H)$^+$. found 365.0563.

Example 74

2-[(4-Bromophenyl)-Hydrazono]-3-(5-Tert-Butyl-Isoxazol-3-Yl)-3-Oxo-Propionitrile (HJC0742)

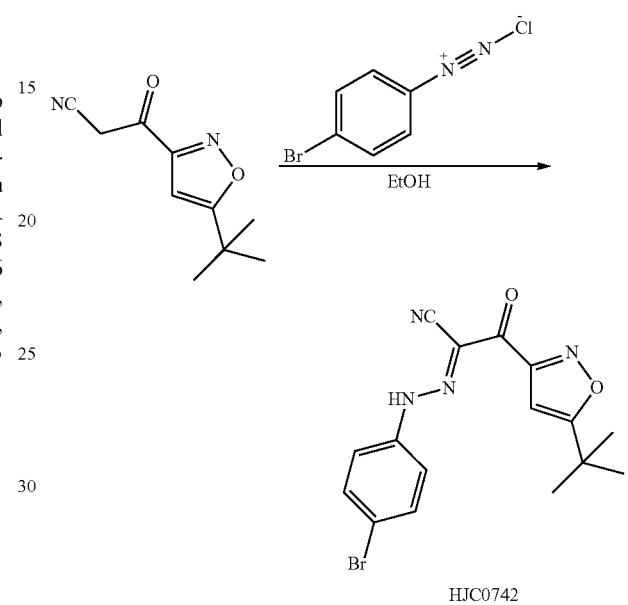

HJC0742

Compound HJC0742 was prepared in 53% yield (two steps from 5-tert-butylisoxazole-3-carboxylic acid ethyl ester) by a procedure similar to that used to prepare compound HJC0680. The title compound was obtained as a yellow solid. HPLC purity 98.9% ($t_R$=22.01 min). $^1$H NMR (600 MHz, DMSO-$d_6$) δ 12.81 (s, 1H), 7.57-7.63 (m, 2H), 7.38-7.44 (m, 2H), 6.63 (s, 1H), 1.36 (s, 9H). $^{13}$C NMR (150 MHz, DMSO-$d_6$) δ 180.8, 178.9, 160.3, 142.7, 132.1, 119.1, 117.7, 112.7, 111.3, 100.2, 32.4, 28.4. HRMS (ESI) calcd for $C_{16}H_{16}BrN_4O_2$ 375.0451 (M+H)$^+$. found 375.0455.

Example 75

2-[(3-Bromophenyl)-Hydrazono]-3-(5-Tert-Butyl-Isoxazol-3-Yl)-3-Oxo-Propionitrile (HJC0743)

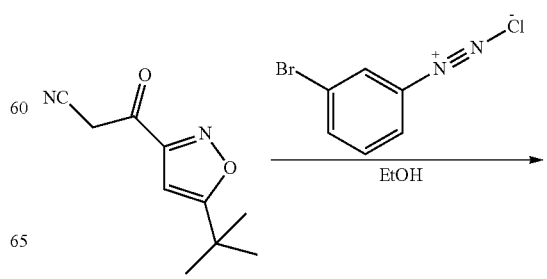

-continued

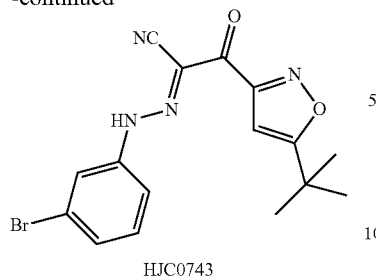

HJC0743

Compound HJC0743 was prepared in 75% yield (two steps from 5-tert-butylisoxazole-3-carboxylic acid ethyl ester) by a procedure similar to that used to prepare compound HJC0680. The title compound was obtained as a yellow solid. HPLC purity 98.3% ($t_R$=21.93 min). $^1$H NMR (600 MHz, DMSO-$d_6$) δ 12.84 (s, 1H), 7.60 (s, 1H), 7.48-7.52 (m, 1H), 7.36-7.40 (m, 2H), 6.69 (s, 1H), 1.38 (s, 9H). $^{13}$C NMR (150 MHz, DMSO-$d_6$) δ 181.0, 179.3, 160.0, 143.8, 131.5, 127.9, 122.4, 119.1, 116.2, 113.4, 110.5, 100.3, 32.5, 28.4.

HRMS (ESI) calcd for $C_{16}H_{16}BrN_4O_2$ 375.0451 (M+H)$^+$. found 375.0456.

Example 76

3-(5-Tert-Butyl-Isoxazol-3-Yl)-2-[(2,5-Dimethylphenyl)-Hydrazono]-3-Oxo-Propionitrile (HJC0744)

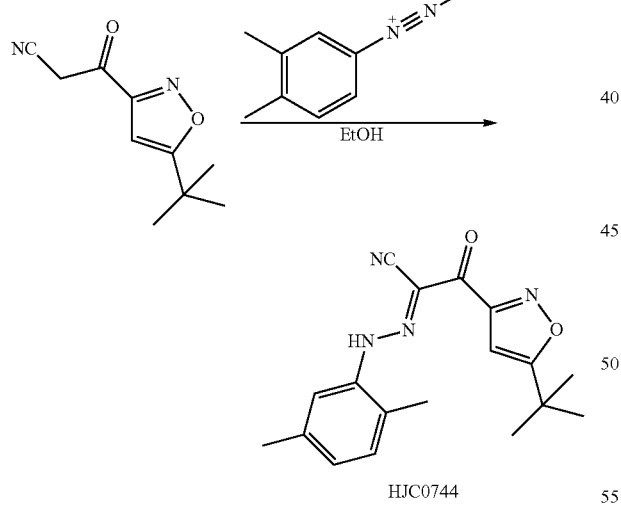

HJC0744

Compound HJC0744 was prepared in 68% yield (two steps from 5-tert-butylisoxazole-3-carboxylic acid ethyl ester) by a procedure similar to that used to prepare compound HJC0680. The title compound was obtained as a yellow solid. HPLC purity 98.6% ($t_R$=23.01 min). $^1$H NMR (600 MHz, DMSO-$d_6$) δ 11.82 (s, 1H), 7.19 (s, 1H), 7.14 (d, 1H, J=7.2 Hz), 6.99 (d, 1H, J=7.2 Hz), 6.68 (s, 1H), 2.30 (s, 3H), 2.26 (s, 3H), 1.35 (s, 9H).

HRMS (ESI) calcd for $C_{18}H_{21}N_4O_2$ 325.1659 (M+H)$^+$. found 325.1664.

Example 77

3-(5-Tert-Butyl-Isoxazol-3-Yl)-3-Oxo-2-(Quinolin-6-Yl-Hydrazono)Propionitrile (HJC0745)

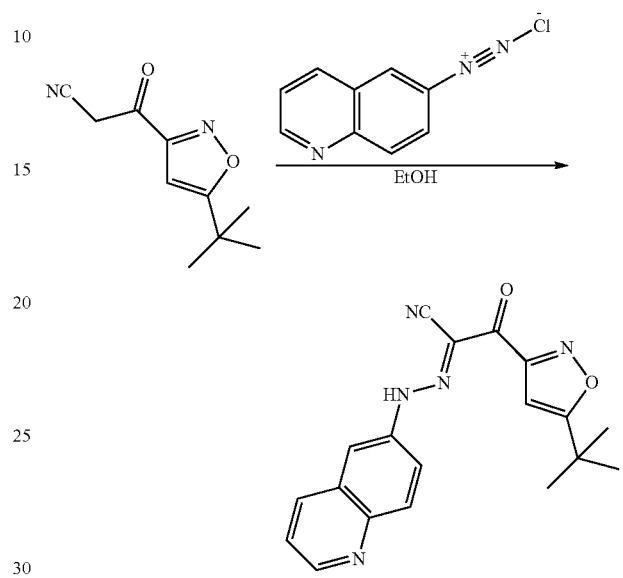

HJC0745

Compound HJC0745 was prepared in 86% yield (two steps from 5-tert-butylisoxazole-3-carboxylic acid ethyl ester) by a procedure similar to that used to prepare compound HJC0680. The title compound was obtained as a yellow solid. HPLC purity 97.8% ($t_R$=16.06 min). $^1$H NMR (600 MHz, DMSO-$d_6$) δ 13.27 (s, 1H), 8.86 (dd, 1H, J=4.2 Hz, J=1.8 Hz), 8.33 (d, 1H, J=8.4 Hz), 8.06 (d, 1H, J=8.4 Hz), 7.94-7.98 (m, 2H), 7.58 (dd, 1H, J=8.4 Hz, J=4.2 Hz), 6.70 (s, 1H), 1.40 (s, 9H). $^{13}$C NMR (150 MHz, DMSO-$d_6$) δ 180.9, 179.1, 160.3, 149.5, 145.1, 141.5, 136.3, 130.0, 128.2, 122.3, 120.3, 114.3, 113.1, 111.2, 100.4, 32.5, 28.5. HRMS (ESI) calcd for $C_{19}H_{18}N_5O_2$ 348.1455 (M+H)$^+$. found 348.1458.

Example 78

3-(5-Tert-Butyl-Isoxazol-3-Yl)-2-[(2,3-Dichlorophenyl)-Hydrazono]-3-Oxo-Propionitrile (HJC0750)

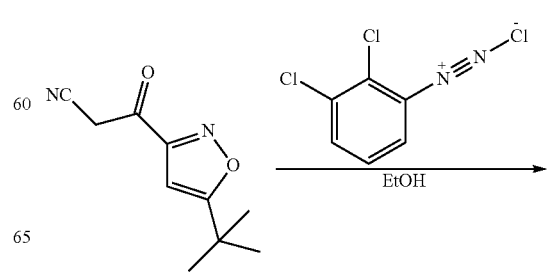

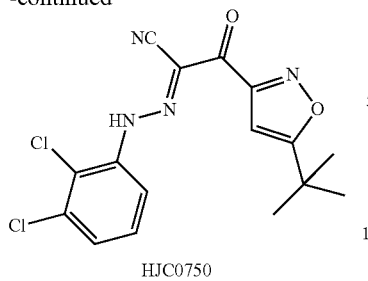

HJC0750

Compound HJC0750 was prepared in 68% yield (two steps from 5-tert-butylisoxazole-3-carboxylic acid ethyl ester) by a procedure similar to that used to prepare compound HJC0680. The title compound was obtained as a yellow solid. HPLC purity 97.5% ($t_R$=23.74 min). $^1$H NMR (600 MHz, DMSO-$d_6$) δ 14.80 (s, 1H), 7.35-7.62 (m, 3H), 6.64 (s, 1H), 1.35 (s, 9H). $^{13}$C NMR (150 MHz, DMSO-$d_6$) δ 181.0, 178.9, 160.5, 142.9, 132.6, 128.8, 127.0, 122.9, 118.2, 115.2, 111.5, 100.3, 32.6, 28.6. HRMS (ESI) calcd for $C_{16}H_{15}Cl_2N_4O_2$ 365.0567 (M+H)$^+$. found 365.0568.

Example 79

3-(5-Tert-Butyl-Isoxazol-3-Yl)-2-[(3-Ethynyl-Phenyl)-Hydrazono]-3-Oxo-Propionitrile (HJC0751)

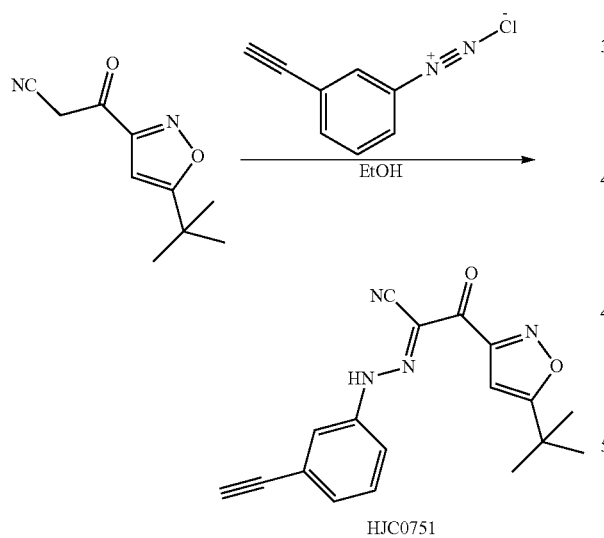

HJC0751

Compound HJC0751 was prepared in 69% yield (two steps from 5-tert-butylisoxazole-3-carboxylic acid ethyl ester) by a procedure similar to that used to prepare compound HJC0680. The title compound was obtained as a yellow solid. HPLC purity 96.2% ($t_R$=20.83 min). $^1$H NMR (600 MHz, DMSO-$d_6$) δ 12.80 (s, 1H), 7.54 (d, 1H, J=8.4 Hz), 7.50 (s, 1H), 7.44 (t, 1H, J=7.8 Hz), 7.30 (d, 1H, J=7.8 Hz), 6.69 (s, 1H), 4.27 (s, 1H), 1.38 (s, 9H). $^{13}$C NMR (150 MHz, DMSO-$d_6$) δ 181.2, 179.7, 160.2, 142.4, 130.1, 128.8, 123.0, 119.5, 117.9, 113.2, 110.7, 100.6, 82.9, 81.6, 32.7, 28.7. HRMS (ESI) calcd for $C_{18}H_{17}N_4O_2$ 321.1346 (M+H)$^+$. found 321.1350.

Example 80

3-{N-[2-(5-Tert-Butyl-Isoxazol-3-Yl)-1-Cyano-2-Oxo-Ethylidene]-Hydrazino}Benzoic Acid Ethyl Ester (HJC0752)

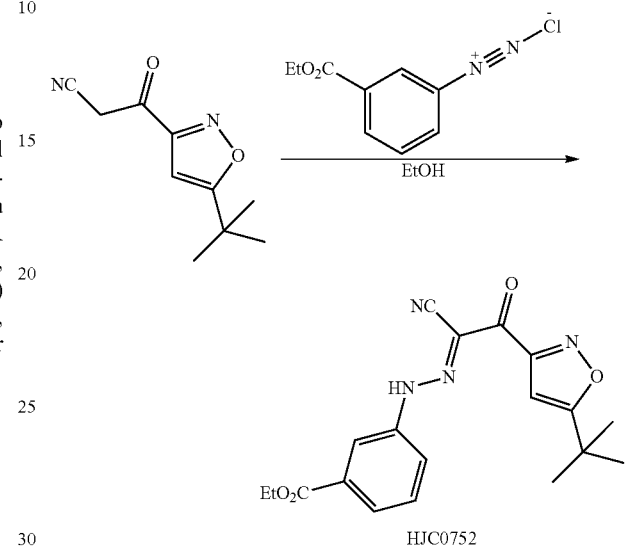

HJC0752

Compound HJC0752 was prepared in 74% yield (two steps from 5-tert-butylisoxazole-3-carboxylic acid ethyl ester) by a procedure similar to that used to prepare compound HJC0680. The title compound was obtained as a yellow solid. HPLC purity 98.8% ($t_R$=21.53 min). $^1$H NMR (600 MHz, DMSO-$d_6$) δ 12.89 (s, 1H), 8.16 (s, 1H), 7.76 (d, 1H, J=7.8 Hz), 7.74 (d, 1H, J=8.4 Hz), 7.57 (t, 1H, J=8.4 Hz), 6.67 (s, 1H), 4.32 (q, 2H, J=7.2 Hz), 1.37 (s, 9H), 1.34 (t, 3H, J=7.2 Hz). $^{13}$C NMR (150 MHz, DMSO-$d_6$) δ 181.1, 179.2, 165.1, 159.9, 142.4, 131.2, 129.8, 125.9, 121.0, 117.3, 113.2, 110.5, 100.1, 61.0, 32.5, 28.4, 14.1. HRMS (ESI) calcd for $C_{19}H_{21}N_4O_4$ 369.1557 (M+H)$^+$. found 369.1558.

Example 81

3-{N-[2-(5-Tert-Butyl-Isoxazol-3-Yl)-1-Cyano-2-Oxo-Ethylidene]-Hydrazino}Benzonitrile (HJC0753)

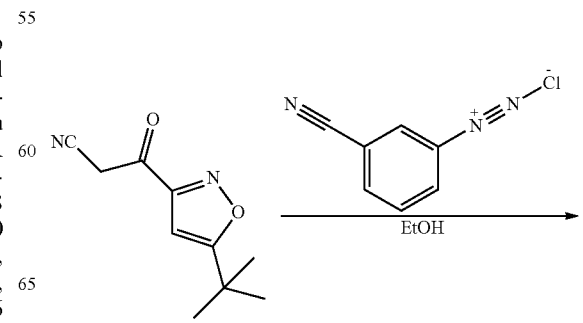

-continued

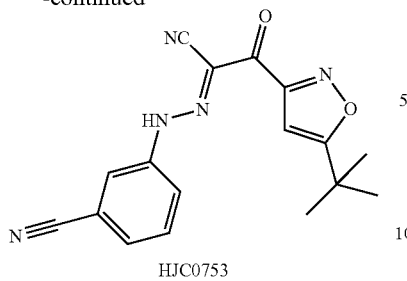

HJC0753

Compound HJC0753 was prepared in 58% yield (two steps from 5-tert-butylisoxazole-3-carboxylic acid ethyl ester) by a procedure similar to that used to prepare compound HJC0680. The title compound was obtained as a yellow solid. HPLC purity 99.3% ($t_R$=19.87 min). $^1$H NMR (600 MHz, DMSO-$d_6$) δ 7.75-7.77 (m, 1H), 7.69 (s, 1H), 7.61-7.63 (m, 2H), 6.69 (s, 1H), 1.36 (s, 9H). $^{13}$C NMR (150 MHz, DMSO-$d_6$) δ 181.3, 179.5, 160.3, 143.8, 131.0, 128.7, 122.0, 119.8, 118.4, 113.9, 112.4, 110.8, 100.5, 32.7, 28.6.
HRMS (ESI) calcd for $C_{17}H_{16}N_5O_2$ 322.1299 (M+H)$^+$. found 322.1303.

Example 82

2-[(3-Acetyl-Phenyl)-Hydrazono]-3-(5-Ter T-Butyl-Isoxazol-3-Yl)-3-Oxo-Propionitrile (HJC0754)

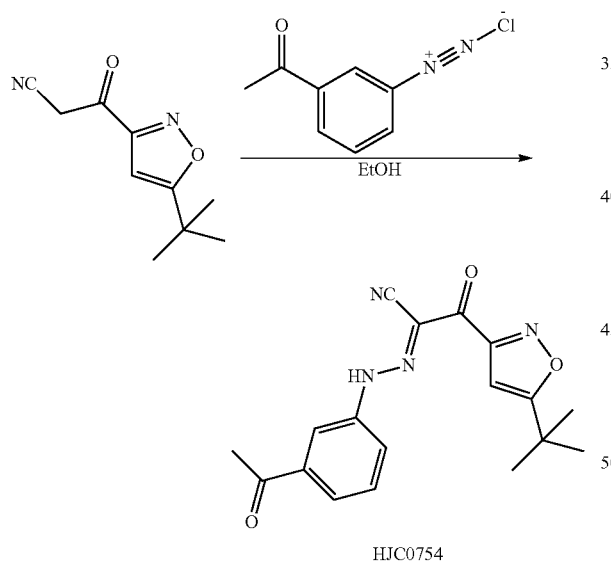

HJC0754

Compound HJC0754 was prepared in 68% yield (two steps from 5-tert-butylisoxazole-3-carboxylic acid ethyl ester) by a procedure similar to that used to prepare compound HJC0680. The title compound was obtained as a yellow solid. HPLC purity 98.2% ($t_R$=19.80 min). $^1$H NMR (600 MHz, DMSO-$d_6$) c 8.05 (s, 1H), 7.79 (d, 1H, J=7.8 Hz), 7.72 (d, 1H, J=8.4 Hz), 7.57 (t, 1H, J=7.8 Hz), 6.66 (s, 1H), 2.57 (s, 3H), 1.37 (s, 9H). $^{13}$C NMR (150 MHz, DMSO-$d_6$) δ 197.4, 181.4, 179.6, 160.2, 142.7, 138.0, 130.1, 125.6, 121.3, 116.0, 113.3, 100.7, 100.3, 32.7, 28.6, 26.8. HRMS (ESI) calcd for $C_{18}H_{19}N_4O_3$ 339.1452 (M+H)$^+$. found 339.1459.

Example 83

3-(5-Tert-Butyl-Isoxazol-3-Yl)-2-[(2,3-Dimethylphenyl)-Hydrazono]-3-Oxo-Propionitrile (HJC0755)

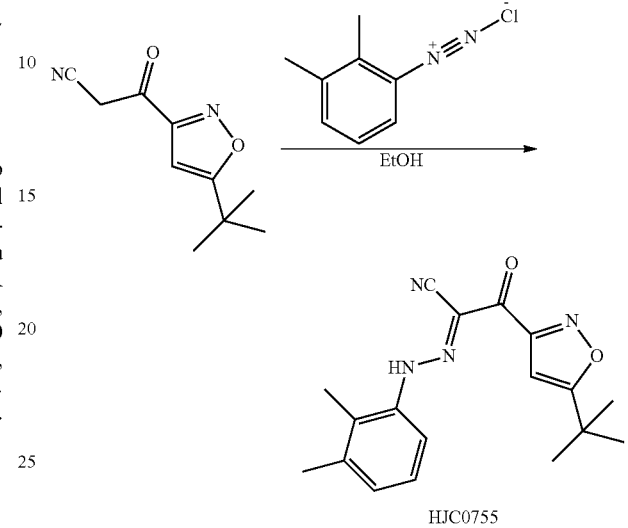

HJC0755

Compound HJC0755 was prepared in 54% yield (two steps from 5-tert-butylisoxazole-3-carboxylic acid ethyl ester) by a procedure similar to that used to prepare compound HJC0680. The title compound was obtained as a yellow solid. HPLC purity 95.7% ($t_R$=22.69 min). $^1$H NMR (600 MHz, DMSO-$d_6$) δ 7.19-7.22 (m, 1H), 7.13-7.16 (m, 1H), 7.12-7.13 (m, 1H), 6.63 (s, 1H), 2.27 (s, 3H), 2.24 (s, 3H), 1.33 (s, 9H). HRMS (ESI) calcd for $C_{18}H_{21}N_4O_2$ 325.1659 (M+H)$^+$. found 325.1666.

Example 84

3-(5-Tert-Butyl-Isoxazol-3-Yl)-2-[(3-Hydroxymethylphenyl)-Hydrazono]-3-Oxo-Propionitrile (HJC0756)

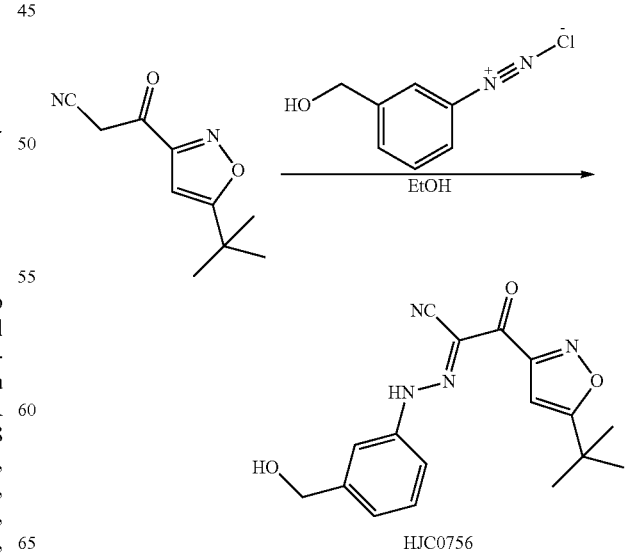

HJC0756

Compound HJC0756 was prepared in 63% yield (two steps from 5-tert-butylisoxazole-3-carboxylic acid ethyl ester) by a procedure similar to that used to prepare compound HJC0680. The title compound was obtained as a yellow solid. HPLC purity 99.6% ($t_R$=17.86 min). $^1$H NMR (600 MHz, DMSO-$d_6$) δ 12.87 (s, 1H), 8.28 (s, 1H), 7.46 (s, 1H), 7.35-7.40 (m, 1H), 7.13-7.18 (m, 1H), 6.65 (s, 1H), 4.49 (s, 2H), 1.36 (s, 9H). $^{13}$C NMR (150 MHz, DMSO-$d_6$) δ 180.9, 179.4, 160.0, 144.2, 142.0, 129.1, 123.6, 115.4, 114.5, 112.4, 110.7, 100.2, 62.5, 32.4, 28.4. HRMS (ESI) calcd for $C_{17}H_{19}N_4O_3$ 327.1452 (M+H)$^+$. found 327.1457.

Example 85

3-(5-Tert-Butyl-Isoxazol-3-Yl)-2-(Indan-5-Yl-Hydrazono)-3-Oxo-Propionitrile (HJC0757)

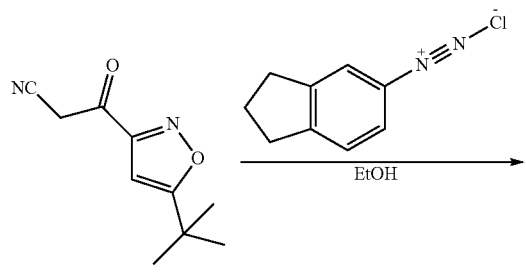

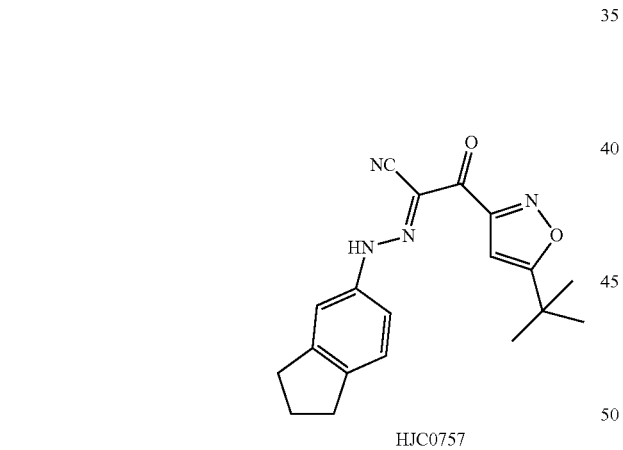

HJC0757

Compound HJC0757 was prepared in 57% yield (two steps from 5-tert-butylisoxazole-3-carboxylic acid ethyl ester) by a procedure similar to that used to prepare compound HJC0680. The title compound was obtained as a yellow solid. HPLC purity 99.6% ($t_R$=22.47 min). $^1$H NMR (600 MHz, DMSO-$d_6$) δ 12.75 (s, 1H), 7.28-7.30 (m, 2H), 7.23-7.25 (m, 1H), 6.65 (s, 1H), 2.82-2.84 (m, 4H), 2.01-2.03 (m, 2H), 1.37 (s, 9H). $^{13}$C NMR (150 MHz, DMSO-$d_6$) δ 181.0, 179.6, 160.3, 145.4, 141.9, 140.8, 125.0, 115.6, 112.7, 111.8, 111.0, 100.6, 32.6, 32.5, 31.9, 28.6, 25.2. HRMS (ESI) calcd for $C_{19}H_{21}N_4O_2$ 337.1659 (M+H)$^+$. found 337.1664.

Example 86

2-[(3,5-Bis-Trifluoromethyl-Phenyl)-Hydrazono]-3-(5-Tert-Butyl-Isoxazol-3-Yl)-3-Oxo-Propionitrile (HJC0758)

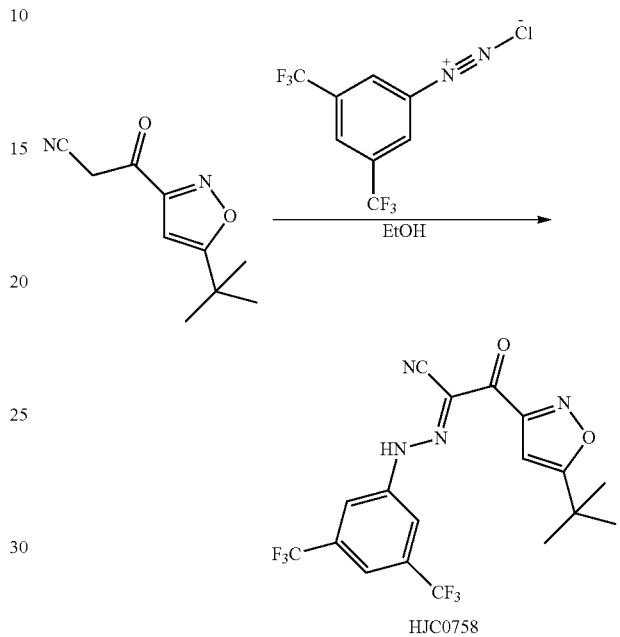

HJC0758

Compound HJC0758 was prepared in 43% yield (two steps from 5-tert-butylisoxazole-3-carboxylic acid ethyl ester) by a procedure similar to that used to prepare compound HJC0680. The title compound was obtained as a yellow solid. HPLC purity 96.4% ($t_R$=22.96 min). $^1$H NMR (600 MHz, DMSO-$d_6$) δ 7.91 (s, 2H), 7.76 (s, 1H), 6.58 (s, 1H), 1.33 (s, 9H). HRMS (ESI) calcd for $C_{18}H_{15}F_6N_4O_2$ 433.1094 (M+H)$^+$. found 433.1098.

Example 87

2-{N'-[2-(5-Tert-Butyl-Isoxazol-3-Yl)-1-Cyano-2-Oxo-Ethylidene]-Hydrazino}-6-Chloro-Benzoic Acid (HJC0759)

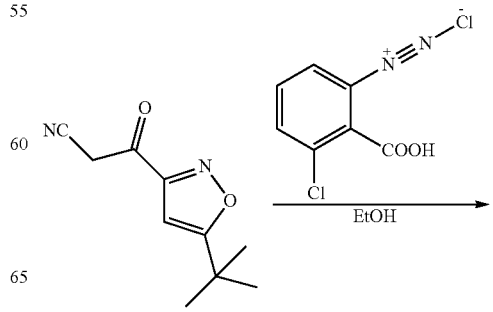

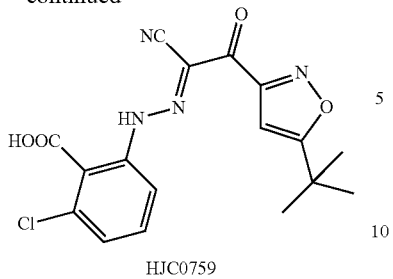

HJC0759

Compound HJC0759 was prepared in 60% yield (two steps from 5-tert-butylisoxazole-3-carboxylic acid ethyl ester) by a procedure similar to that used to prepare compound HJC0680. The title compound was obtained as a yellow solid. HPLC purity 96.5% ($t_R$=20.02 min). $^1$H NMR (600 MHz, DMSO-$d_6$) δ 13.29 (s, 1H), 7.21-7.24 (m, 2H), 7.11-7.12 (m, 1H), 6.37 (s, 1H), 1.34 (s, 9H). $^{13}$C NMR (150 MHz, DMSO-$d_6$) δ 179.1, 178.5, 167.3, 162.9, 152.3, 130.3, 129.8, 129.3, 124.5, 115.7, 114.4, 112.2, 100.3, 32.4, 28.8.

HRMS (ESI) calcd for $C_{17}H_{16}ClN_4O_4$ 375.0855 (M+H)$^+$. found 375.0858.

Example 88

3-(5-Tert-Butyl-Isoxazol-3-Yl)-2-[(3-Chloro-4-Hydroxy-Phenyl)-Hydrazono]-3-Oxo-Propionitrile (HJC0760)

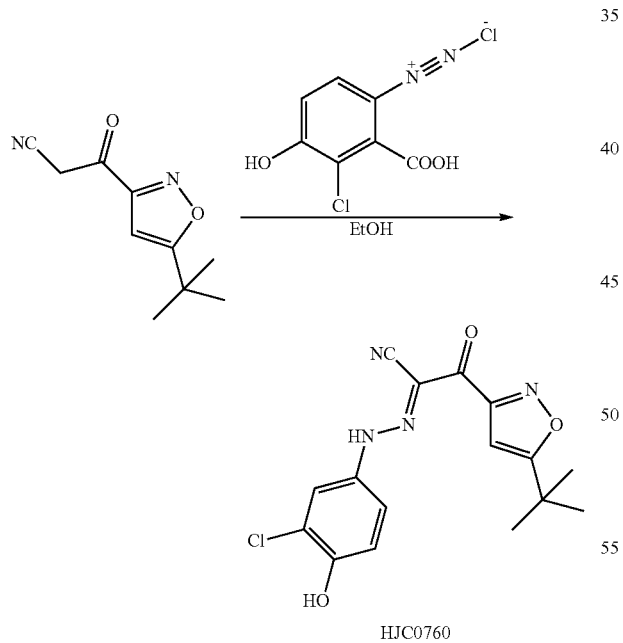

HJC0760

Compound HJC0760 was prepared in 43% yield (two steps from 5-tert-butylisoxazole-3-carboxylic acid ethyl ester) by a procedure similar to that used to prepare compound HJC0680. The title compound was obtained as a yellow solid. HPLC purity 99.0% ($t_R$=18.89 min). $^1$H NMR (600 MHz, DMSO-$d_6$) δ 12.78 (s, 1H), 10.32 (s, 1H), 7.38 (s, 1H), 7.28-7.30 (m, 1H), 6.98-7.01 (m, 1H), 6.60 (s, 1H), 1.37 (s, 9H). HRMS (ESI) calcd for $C_{16}H_{16}ClN_4O_3$ 347.0905 (M+H)$^+$. found 347.0909.

Example 89

2-[(3-Chloro-Phenyl)-Hydrazono]-3-(5-Methyl-Isoxazol-3-Yl)-3-Oxo-Propionitrile (HJC0768)

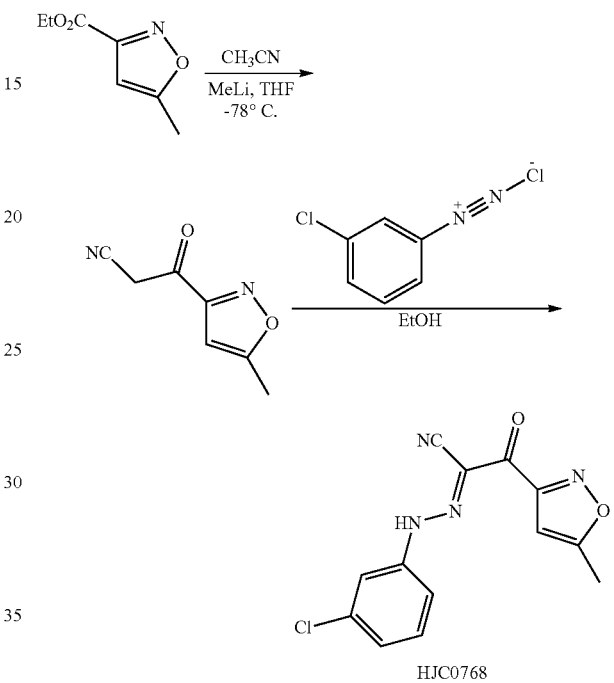

HJC0768

Compound HJC0768 was prepared in 42% yield (two steps from 5-tert-butylisoxazole-3-carboxylic acid ethyl ester) by a procedure similar to that used to prepare compound HJC0680. The title compound was obtained as a yellow solid. HPLC purity 98.4% ($t_R$=19.18 min). $^1$H NMR (600 MHz, DMSO-$d_6$) δ 7.51 (s, 1H), 7.41-7.45 (m, 2H), 7.20-7.25 (m, 1H), 6.63 (s, 1H), 2.51 (s, 3H). $^{13}$C NMR (150 MHz, DMSO-$d_6$) δ 179.3, 170.3, 160.6, 144.4, 134.1, 131.3, 125.2, 116.8, 115.9, 113.3, 111.0, 103.0, 11.8. HRMS (ESI) calcd for $C_{13}H_{10}ClN_4O_2$ 289.0487 (M+H)$^+$. found 289.0492.

Example 90

2-[(3,5-Dichlorophenyl)-Hydrazono]-3-(5-Methyl-Isoxazol-3-Yl)-3-Oxo-Propionitrile (HJC0770)

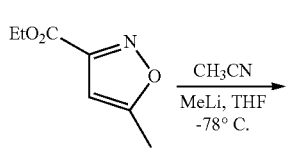

-continued

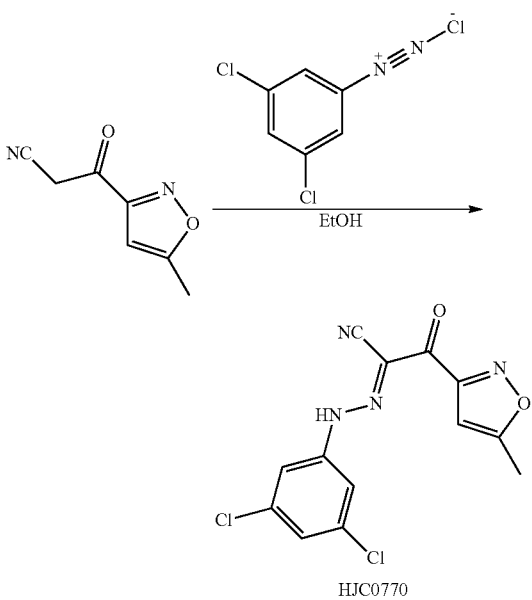

HJC0770

Compound HJC0770 was prepared in 35% yield (two steps from 5-tert-butylisoxazole-3-carboxylic acid ethyl ester) by a procedure similar to that used to prepare compound HJC0680. The title compound was obtained as a yellow solid. HPLC purity 98.4% ($t_R$=20.79 min). $^1$H NMR (600 MHz, DMSO-$d_6$) δ 12.78 (s, 1H), 7.45 (s, 2H), 7.36 (s, 1H), 6.63 (s, 1H), 2.49 (s, 3H). $^{13}$C NMR (150 MHz, DMSO-$d_6$) δ 179.1, 170.2, 160.8, 146.4, 134.9, 124.1, 116.0, 113.9, 111.2, 103.0, 11.8. HRMS (ESI) calcd for $C_{13}H_9Cl_2N_4O_2$ 323.0097 (M+H)$^+$. found 323.0103.

Example 91

Discovery of EPAC Specific Inhibitors

A. Results

Biochemical Characterization of EPAC Antagonists—

Figures 7A, 7B:
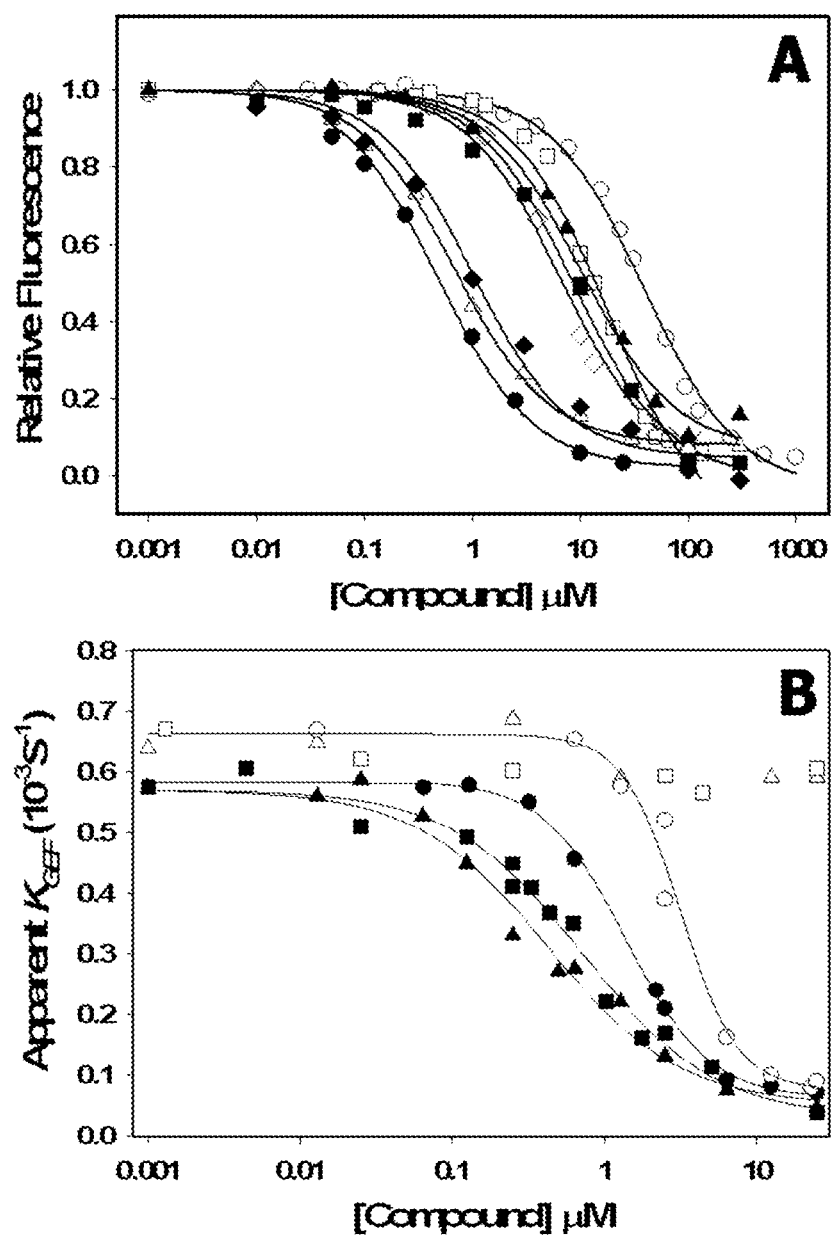
FIGS. 7A-7B. Relative potency of EPAC specific antagonists. (A) Dose-dependent competition of ESIs (open circles) and cAMP (closed squares) with 8-NBD-cAMP in binding to EPAC2. (B) Dose-dependent inhibition of EPAC1 (closed circles) or EPAC2 (open circles) GEF activity by ESI-05, ESI-07 and ESI-09 in the presence of 25 M cAMP.
Figure 8:
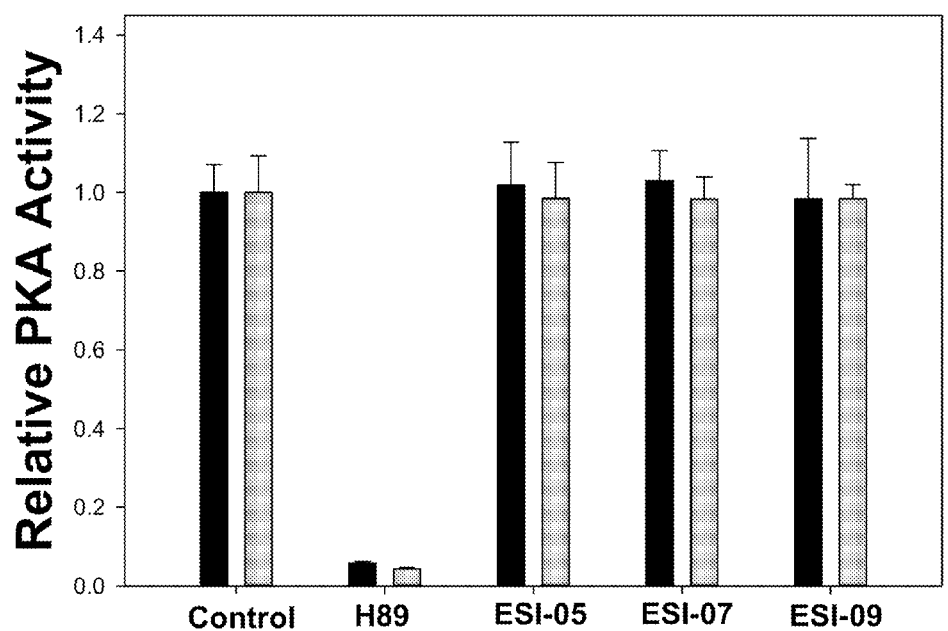
FIG. 8. Effect of ESI-09 on type I and II PKA activity. Relative Type I (filled bars) and II (open bars) PKA holoenzyme activities in the presence of 100 M cAMP plus vehicle control, 25 µM H-89, 25 µM ESI-05, 25 µM ESI-07, or 25 µM ESI-09. Data are presented in the format of means and standard deviations (n=3).

To determine the relative binding affinity of the EPAC antagonist identified in an initial screen (FIG. 1), dose-dependent titrations were performed to test the ability of these compounds to compete with the binding of 8-NBD-cAMP to EPAC2. When various concentrations of cAMP or EPAC2 antagonists were added to reaction mixture with fixed concentrations of EPAC2 and 8-NBD-cAMP, a dose-dependent decrease in 8-NBD-cAMP fluorescence was observed (FIG. 7A). While cAMP competed with 8-NBD-cAMP binding with an apparent $IC_{50}$ of 39 µM, all selected EPAC2 antagonists showed an increased potency with apparent $IC_{50}$ ranging from 0.48 to 18 µM (Table 1). To determine if this apparent high affinity binding of EPAC2 antagonists can be translated to comparative potencies in suppressing the GEF activity of EPAC2, the inventors also determined the inhibition curves of Rap1-GDP exchange activity for three of these EPAC2 antagonists. As shown in FIG. 7B, compounds ESI-05, ESI-07 and ESI-09 inhibited cAMP-mediated EPAC2 GEF activity with apparent $IC_{50}$ of 1.4, 0.43 or 0.7 µM, respectively (Table 2). Since these antagonists were identified using EPAC2 as a target, the inventors tested if these compounds were also effective in suppressing cAMP-mediated EPAC1 GEF activity. While compound ESI-09 inhibited EPAC1-mediated Rap1-GDP exchange activity in a dose-dependent manner similar to that of EPAC2 with an apparent $IC_{50}$ of 3.2 µM, compounds ESI-05 and ESI-07 were completely ineffective in suppressing EPAC1 GEF activity (FIG. 7B). To test the specificity of ESI-05, ESI-07 and ESI-09, counter-screening assays were performed that measure type I and type II PKA holoenzyme activity, respectively. 25 µM of ESI-05, ESI-07 and ESI-09 did not significantly alter cAMP-induced type I and II PKA holoenzymes activation while H89, a selective PKA inhibitor, blocked the type I or II PKA activities completely (FIG. 8).

TABLE 1

Apparent $IC_{50}$ values of ESIs for competing with 8-NBD-cAMP in binding EPAC2.

| Compound | Apparent $IC_{50}$ (µM) | Relative Potency (RA)* |
|---|---|---|
| cAMP | 39 ± 2.0 | 1.0 |
| ESI-04 | 6.7 ± 0.7 | 5.8 |
| ESI-05 | 0.48 ± 0.03 | 81 |
| ESI-06 | 1.0 ± 0.2 | 39 |
| ESI-07 | 0.67 ± 0.03 | 57 |
| ESI-08 | 8.7 ± 1.1 | 4.5 |
| ESI-09 | 10 ± 1.2 | 3.9 |
| ESI-10 | 18 ± 2.0 | 2.2 |

*RA = $IC_{50, cAMP}/IC_{50, compound}$

TABLE 2

Apparent $IC_{50}$ values of ESIs for suppressing EPAC1 and EPAC2 GEF activities.

| Compound | EPAC1 $IC_{50}$ (µM) | EPAC2 $IC_{50}$ (µM) |
|---|---|---|
| ESI-05 | NMA* | 0.43 ± 0.06 |
| ESI-07 | NMA* | 0.72 ± 0.08 |
| ESI-09 | 3.2 ± 0.4 | 1.4 ± 0.1 |

*NMA: no measurable activity

Cellular Characterization of EPAC Antagonists—

To test if the newly identified EPAC antagonists were capable of modulating EPAC activation in living cells, the ability of these compounds in suppressing EPAC-mediated Rap1 cellular activation is monitored. As shown in FIG. 8A, when HEK293 cells that ectopically express full-length EPAC2 proteins were treated with a EPAC selective cAMP analog 8-(4-Chlorophenylthio)-2'-O-methyladenosine-3',5'-cyclic monophosphate, acetoxymethyl ester (007-AM), an increase in the fraction of GTP-bound cellular Rap1 was observed. Pre-treatment of HEK293/EPAC2 cells with 10 µM of compounds ESI-05, ESI-07, and ESI-09 led a significant reduction of 007-AM induced Rap1 activation while ESI-08 was much less effective. On the other hand, when HEK293 cells that ectopically express full-length EPAC1 proteins were used, only compound ESI-09 was effective in blocking 007-AM induced Rap1 activation while compound ESI-05 and ESI-07 was ineffective (FIG. 8B). These results are consistent with the biochemical Rap1 exchange data shown in FIG. 7B and further confirm that compounds ESI-05 and ESI-07 are EPAC2-specific antagonists while compounds ESI-09 is a pan-EPAC antagonist.

Figure 10:
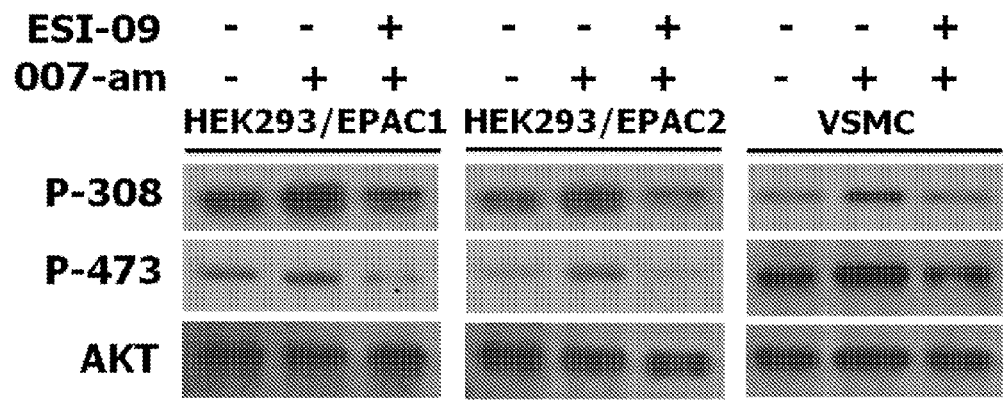
FIG. 10. Effect of ESI-09 on EPAC-mediated PKB phosphorylation in HEK293/EPAC1, HEK293/EPAC2, and human vascular smooth muscle (hVSMC) cells. Serum-starved HEK293/EPAC1, HEK293/EPAC2, and hVSMC cells with or without pretreatment of 10 M ESI-09 were stimulated with 10 µM 007-AM. Cell lysates were subjected to Western blot analysis as described under "Experimental Procedures" using anti-phospho-Ser473-specific (PKB-P473) and anti-phospho-Thr308-specific (PKB-P308) PKB antibodies. Similar results were obtained from three independent experiments.

In addition to mediate cAMP-induced Rap1 activation, EPAC proteins are also known to activate the Akt/PKB signaling pathways while PKA inhibits Akt/PKB activation (Mei et al. (2002) J. Biol. Chem. 277: 11497-11504). To determine if ESI-09 is capable of blocking EPAC1- or EPAC2-mediated Akt activation, the phosphorylation status of T308 and S473 of Akt in HEK293/EPAC1 or HEK293/EPAC2 cells, as well as in vascular smooth muscle cell (VSMC) expressing endogenous levels of EPACs, was followed using anti phospho-Akt antibodies. 007-AM led to an increase in Akt phosphorylation for both T308 and S473 as expected. Pretreatment with 10 µM of ESI-09 for 5 min before the administration of 007-AM completely blocked EPAC1 and EPAC2-mediated Akt phosphorylation. Similar results were obtained using endogenously expressed EPAC1 and EPAC2 in human vascular smooth muscle cells (FIG. 10). These results demonstrate that ESI-09 is capable of suppressing EPAC1 and EPAC2 mediated cellular functions.

ESI-09 Inhibits Pancreatic Cancer Migration—

Figure 11:
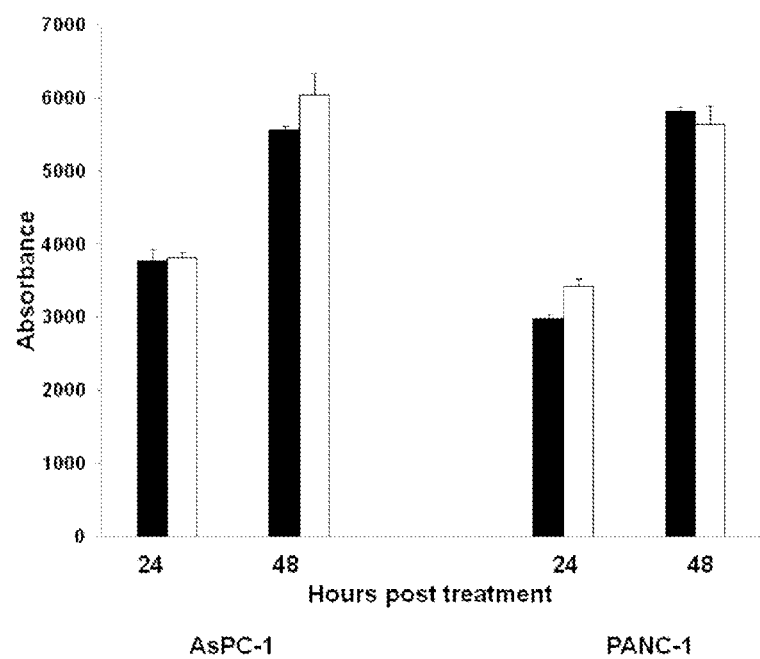
FIG. 11. Effects of ESI-09 treatment on pancreatic cancer cell viability. AsPC-1 and PANC-1 cells were treated with vehicle control (open bars) or with 10 M ESI-09 (filled bars) for 24 hours and 48 hours. Cell viability was measured by a fluorometric alamar blue assay. Bars represent mean±s.d. (n=3).
Figures 12A, 12B, 12C, 12D:
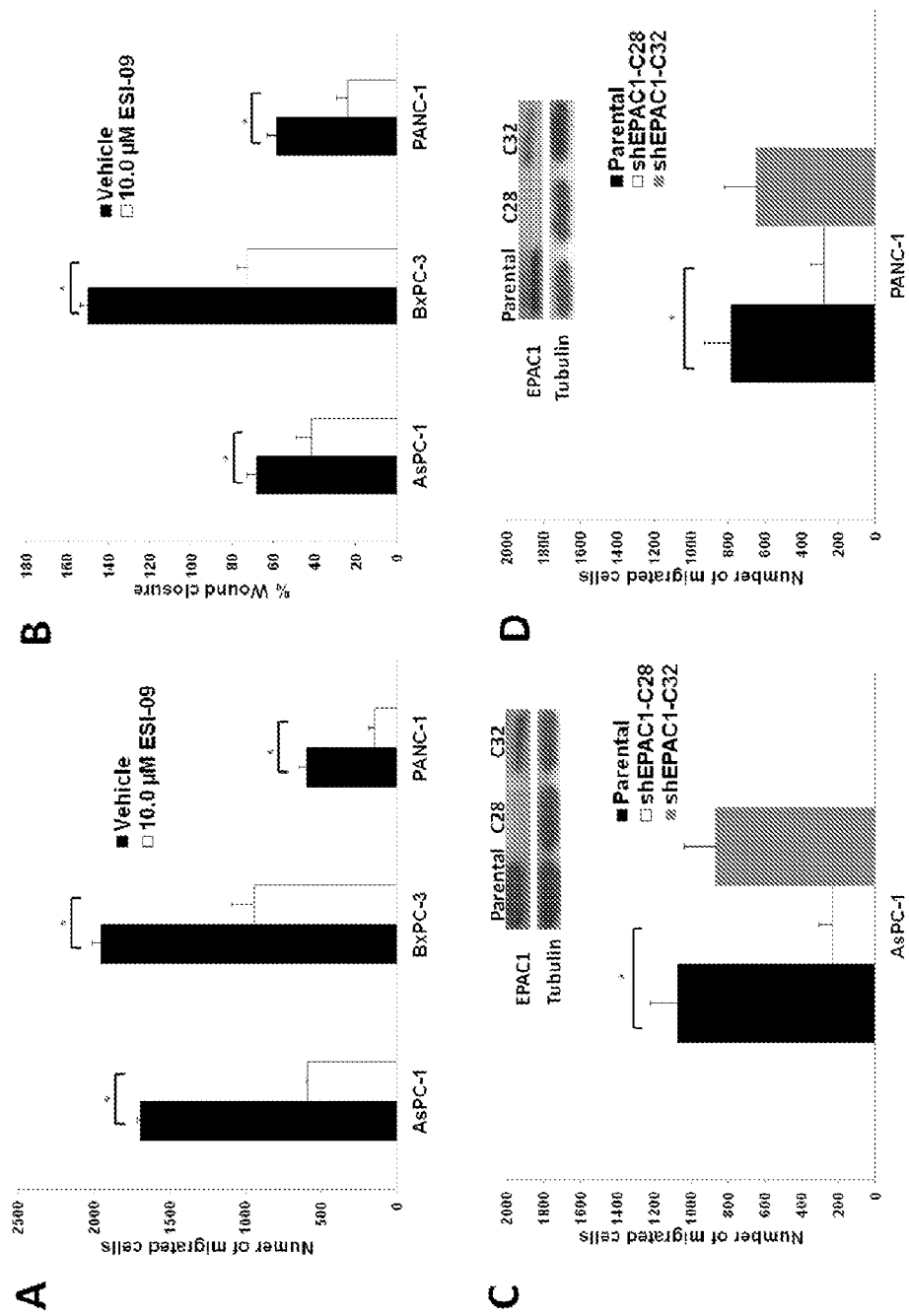
FIGS. 12A-12D. Effects of EPAC inhibition on pancreatic cancer cell migration. Pretreatment of AsPC-1, BxPC-3, and PANC-1 with 10.0 µM ESI-09 for 24 hours significantly (P<0.05) decreased cell migration in trans-well (A) and wound-healing assays (B), respectively. Black bars: vehicle controls; white bars: ESI-09. Suppression of EPAC1 expression by shEPAC1-C28, but not shEPAC1-C32, significantly (P<0.02) reduced migration of AsPC-1 (C) and PANC-1 (D) cells. There was no significant difference in migration between parental and shEPAC1-C32 transected cells in either cell line. Black bars: parental controls; white bars: shEPAC1-C28; gray bars; shEPACC1-C32. Bars represent mean±s.d. (n=3).
Figure 13:
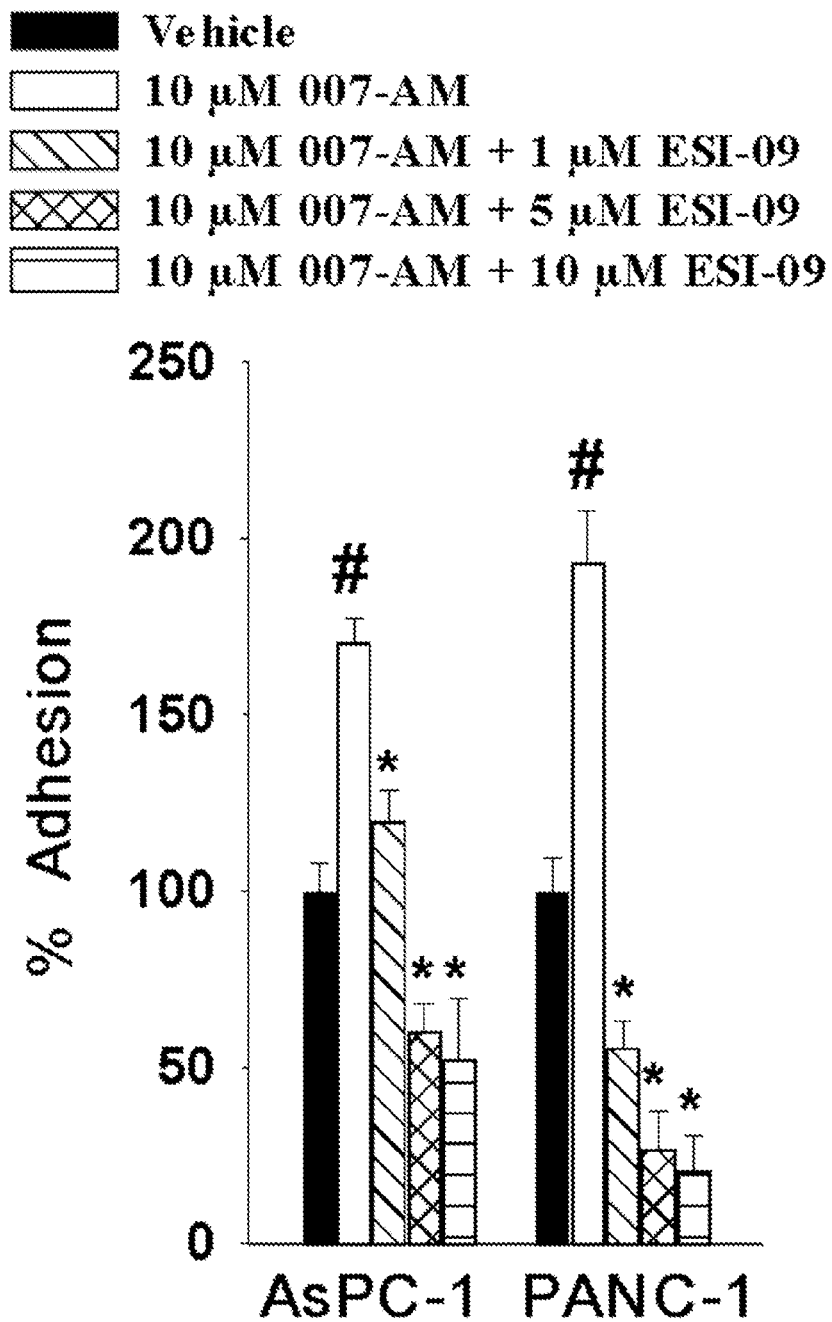
FIG. 13 ESI-09 inhibits EPAC1-mediated adhesion of PDA cells on collagen I. AsPC-1 and PANC-1 cells were stimulated with vehicle or 10 µM 007-AM after treatment with the indicated concentrations of ESI-09 for 5 minutes. Bars represent mean±s.d. (n=3). #Significantly higher than vehicle group (P<0.03). *Significantly lower than 007-AM stimulated group (P<0.02).
Figure 14:
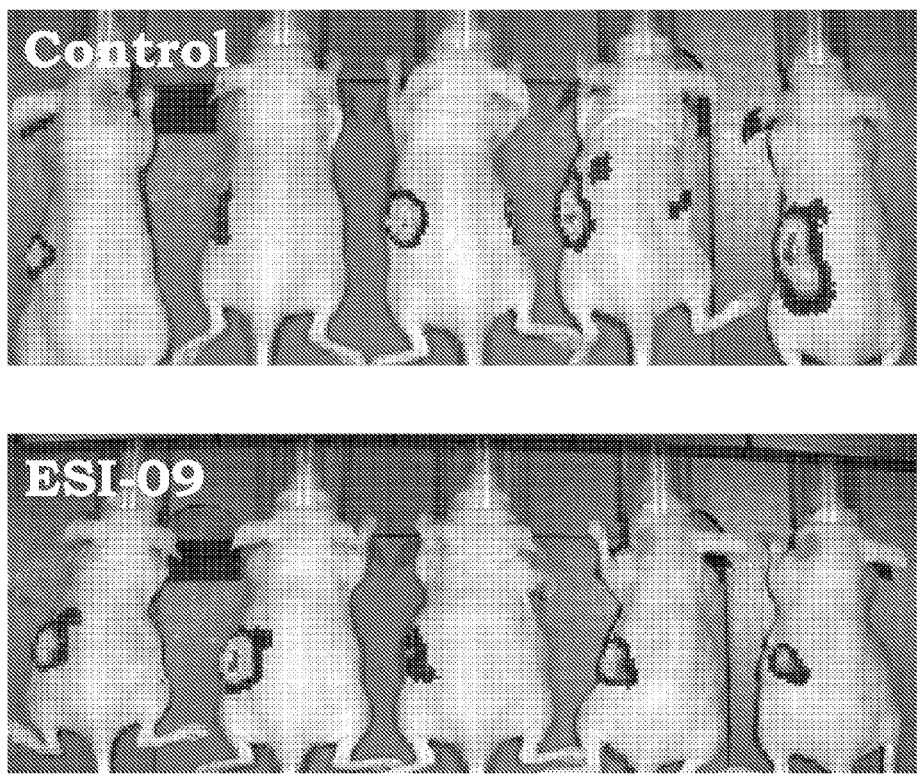
FIG. 14. ESI-09 inhibits PDA metastasis in vivo. MIA PaCa-2 stably expressing luciferase was orthotopically implanted into the pancreas of athymic nude mice. The mice were randomly divided into two groups and treated with vehicle or ESI-09 (50 mg/kg, oral gavage), respectively. The growth and metastasis of the tumors were monitored by weekly bioluminescence imaging using the IVIS bioluminescence imaging system.

The discovery of a novel EPAC specific inhibitor provides a new tool for manipulating cAMP signaling pathways and for studying physiological functions of EPAC proteins. It has been recently reported that EPAC1 is over-expressed in pancreatic adenocarcinoma (Lorenz et al. (2008) Pancreas 37: 102-103). However, the functional role of EPAC1 elevation in this neoplasm is not clear. The inventors sought to employ ESI-09 to determine the role of EPAC1 signaling in pancreatic cancer. Treatment of pancreatic cancer cells with ESI-09 did not significantly affect cell proliferation and viability (FIG. 11). On the other hand, when pretreated with 10.0 µM of ESI-09, a significant decrease in cell migration was observed for three pancreatic cancer cell lines, AsPC-1, BxPC-3, and PANC-1 using both trans-well migration/invasion and wound healing migration assays (FIGS. 12A & 12B). In order to determine if the observed impact on cell migration is EPAC1 specific, the effect of suppressing EPAC1 expression on AsPC-1 and PANC-1 migration using RNAi was examined. As shown in FIGS. 12C & 12D, shEPAC1 clone C28 led to a near complete knockdown of EPAC1 expression and significantly inhibited migration of both cell lines, while slight reduction of EPAC1 expression by shEPAC1 clone C32 had no influence on their migratory capability. These results, combined with the fact that ESI-09 inhibited pancreatic cancer migration, suggest EPAC1 promotes pancreatic cancer cell migration. To further determine how ESI-09 inhibits PDA cell migration and invasion, a cell adhesion assay was performed using a collagen I matrix. As shown in FIG. 13, 007-AM led to an increase in cell adhesion for both AcPC-1 and PANC-1 cells, while pretreatment with ESI-09 decreased 007-AM induced cell adhesion dose-dependently. To determine the in vivo anti-metastatic effect of ESI-09, MIA PaCa-2 stably expressing luciferase were orthotopically implanted into the pancreas of athymic nude mice. The mice were randomly divided into two groups and treated with vehicle or ESI-09 (50 mg/kg per day, oral gavage), respectively. The growth and metastasis of the tumors were monitored by weekly bioluminescence imaging using the IVIS bioluminescence imaging system. As shown in FIG. 14, ESI-09 treatment reduced PDA metastasis.

B. Experimental Procedures

Rap1 Activation Assay—

Cellular activation of Rap1 was determined by pull-down of lysates derived from human vascular smooth muscle cell and HEK293 cells stably expressing EPAC1 or EPAC2 employing Ral-GDS-RBD-GST affinity beads as described earlier (Mei and Cheng (2005) Molecular Biosystems 1: 325-331).

Phosphorylation of Akt—

Cellular proteins from cell lysates treated with various reagents were separated by SDS-PAGE and transferred to polyvinylidene difluoride membrane. The levels of Akt activation were probed by immuno-blotting analyses using anti-phosphate T308 PKB antibodies (1:1000) and anti-phosphate S473 PKB antibodies (1:1000). At least three independent experiments were performed for each Western blot.

Insulin Secretion Assay—

INS-1 cells were plated into 96-well plates pre-coated with poly-lysine at a density of $1 \times 10^5$ cells/well. After overnight incubation, the medium was replaced with Krebs-Ringer buffer (KRB) containing 2.9 mM glucose. After an additional two-hour incubation, the cells were pre-treated with testing compounds or DMSO vehicle as a control in fresh KRB containing 16.7 mM glucose for 10 min, followed by a 30 min stimulation by 10 µM of 007-am. The supernatant was collected and subjected to insulin qualification using an Ultra Sensitive Rat Insulin ELISA kit from Crystal Chem. Inc.

Transwell Migration/Invasion Assay—

The top chamber of 8 micron inserts (Costar Inc) were coated with BD Matrigel™ Basement Membrane Matrix (50 g/mL). Cells ($2 \times 10^5$) pretreated with 10.0 µM of ESI-09 for 24 hours were added to the top chamber of the inserts in serum free RPMI medium containing 0.25% BSA. The bottom chamber was filled with 600.0 µL of RPMI containing 10% FBS and 10.0 µM ESI-09. The cells were then incubated at 37° C. in 5% $CO_2$ for 20 hours. Cells were removed from the top chamber and migrated cells were fixed in methanol and stained with crystal violet. The number of migrated cells were counted from four different fields.

Wound Healing Assay—

Cells were grown to 95-100% confluency before a scratch wound was made. The medium was changed to RPMI 10% FBS containing 10.0 µM ESI-09. The cells were then incubated at 37° C. in 5% $CO_2$. The wound was imaged at 0 hours and 22 hours after changing the medium. Healing rate was determined by calculating the percentage of wound closure normalized to a 1.0 mm wound according to the following equation: % wound closure=(distance between the edges of the wound before treatment with ES-09−distance between the edges of the wound 22 hours post treatment with ES-09)/1.0×100.

The invention claimed is:

1. An Exchange Protein Activated by cAMP (EPAC) specific inhibitor (ESI) having a formula of:

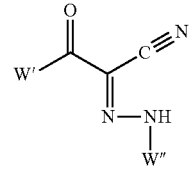

Formula VII where W' is a substituted or unsubstituted isoxazole and W''' is a 3-trifluoromethylphenyl; 3,5-di-trifluoromethylphenyl; 3-chlorophenyl; 2-chlorophenyl; 3,6-dichlorophenyl; 3,5-dichlorophenyl; 4-bromophenyl; 3-bromophenyl; 2,3-dichlorophenyl; or 3-chloro-4-hydroxyphenyl, wherein the compound is not 3-(5-tert-Butyl-isoxazol-3-yl)-2-[(3-chlorophenyl)-hydrazono]-3-oxo-propionitrile (ESI-09).

2. The EPAC specific inhibitor of claim 1, wherein W' is a $C_1$ to $C_{10}$ alkyl substituted isoxazole.

3. The EPAC specific inhibitor of claim 2, wherein the substituted isoxazole is methyl, ethyl, n-propyl, isopropyl, n-butyl, sec-butyl, iso-butyl, tert-butyl, neo-pentyl, n-pentyl, or isopenyl substituted isoxazole.

4. The EPAC specific inhibitor of claim 1, wherein W' is a 5-methyl isoxazole or a 5-tert-butyl isoxazole.

5. The EPAC specific inhibitor of claim 1, wherein the compound is selected from 3-(5-tert-Butyl-isoxazol-3-yl)-3-oxo-2-[(3-trifluoromethyl-phenyl)-hydrazono]propionitrile (HJC0720); 2-[(3,5-Bis-trifluoromethyl-phenyl)-hydrazono]-3-(5-tert-butyl-isoxazol-3-yl)-3-oxo-propionitrile (HJC0758); 3-(5-tert-Butyl-isoxazol-3-yl)-2-[(2-chlorophenyl)-hydrazono]-3-oxo-propionitrile (HJC0693); 3-(5-tert-Butyl-isoxazol-3-yl)-2-[(2,5-dichlorophenyl)-hydrazono]-3-oxo-propionitrile (HJC0696); 3-(5-tert-Butyl-isoxazol-3-yl)-2-[(3,5-dichlorophenyl)-hydrazono]-3-oxo-propionitrile (HJC0726); 2-[(4-Bromophenyl)-hydrazono]-3-(5-tert-butyl-isoxazol-3-yl)-3-oxo-propionitrile (HJC0742); 2-[(3-Bromophenyl)-hydrazono]-3-(5-tert-butyl-isoxazol-3-yl)-3-oxo-propionitrile (HJC0743); 3-(5-tert-Butyl-isoxazol-3-yl)-2-[(2,3-dichlorophenyl)-hydrazono]-3-oxo-propionitrile (HJC0750); or 2-[(3,5-Dichlorophenyl)-hydrazono]-3-(5-methyl-isoxazol-3-yl)-3-oxo-propionitrile (HJC0770).

6. A pharmaceutically acceptable salt of the EPAC specific inhibitor of claim 1.

7. A method for selectively inhibiting an EPAC protein comprising contacting the EPAC protein with 3-(5-tert-Butyl-isoxazol-3-yl)-2-[(3-chlorophenyl)-hydrazono]-3-oxo-propionitrile (ESI-09) or an EPAC specific inhibitor of claim 1, wherein an activity of the EPAC protein is inhibited.

8. A method of treating cancer mediated by EPAC comprising administering an EPAC specific inhibitor to a subject having said cancer, wherein the EPAC specific inhibitor is 3-(5-tert-Butyl-isoxazol-3-yl)-2-[(3-chlorophenyl)-hydrazono]-3-oxo-propionitrile (ESI-09) or an EPAC specific inhibitor of claim 1.

9. The method of claim 8, wherein the EPAC specific inhibitor is selected from the EPAC specific inhibitors of claim 1.

10. A method of enhancing an immune response to an antigen comprising administering an EPAC specific inhibitor to a subject exposed to the antigen, wherein the EPAC specific inhibitor is 3-(5-tert-Butyl-isoxazol-3-yl)-2-[(3-chlorophenyl)-hydrazono]-3-oxo-propionitrile (ESI-09) or an EPAC specific inhibitor of claim 1.

11. The method of claim 10, wherein the EPAC specific inhibitor is selected from the EPAC specific inhibitors of claim 1.

12. A method of enhancing leptin sensitivity comprising administering an EPAC specific inhibitor to a subject having leptin resistance, wherein the EPAC specific inhibitor is 3-(5-tert-Butyl-isoxazol-3-yl)-2-[(3-chlorophenyl)-hydrazono]-3-oxo-propionitrile (ESI-09) or an EPAC specific inhibitor of claim 1.

13. The method of claim 12, wherein the EPAC specific inhibitor is selected form the EPAC specific inhibitors of claim 1.

14. A method of suppressing bacteria, virus, or fungi infection comprising administering an EPAC specific inhibitor to a subject having a bacteria, virus, or fungi infection, wherein the EPAC specific inhibitor is 3-(5-tert-Butyl-isoxazol-3-yl)-2-[(3-chlorophenyl)-hydrazono]-3-oxo-propionitrile (ESI-09) or an EPAC specific inhibitor of claim 1.

15. The method of claim 14, wherein the EPAC specific inhibitor is selected from the EPAC specific inhibitors of claim 1.

16. The EPAC specific inhibitor of claim 1, wherein the EPAC specific inhibitor is 3-(5-tert-Butyl-isoxazol-3-yl)-2-[(3,5-dichlorophenyl)-hydrazono]-3-oxo-propionitrile (HJC0726).

17. The method of claim 7, wherein the EPAC specific inhibitor is 3-(5-tert-Butyl-isoxazol-3-yl)-2-[(3-chlorophenyl)-hydrazono]-3-oxo-propionitrile (ESI-09).

18. The method of claim 8, wherein the EPAC specific inhibitor is 3-(5-tert-Butyl-isoxazol-3-yl)-2-[(3-chlorophenyl)-hydrazono]-3-oxo-propionitrile (ESI-09).

19. The method of claim 9, wherein the EPAC specific inhibitor is 3-(5-tert-Butyl-isoxazol-3-yl)-2-[(3-chlorophenyl)-hydrazono]-3-oxo-propionitrile (ESI-09).

20. The method of claim 12, wherein the EPAC specific inhibitor is 3-(5-tert-Butyl-isoxazol-3-yl)-2-[(3-chlorophenyl)-hydrazono]-3-oxo-propionitrile (ESI-09).

21. The method of claim 14, wherein the EPAC specific inhibitor is 3-(5-tert-Butyl-isoxazol-3-yl)-2-[(3-chlorophenyl)-hydrazono]-3-oxo-propionitrile (ESI-09).

* * * * *